US007785861B2

(12) United States Patent
Devroe et al.

(10) Patent No.: US 7,785,861 B2
(45) Date of Patent: Aug. 31, 2010

(54) HYPERPHOTOSYNTHETIC ORGANISMS

(75) Inventors: Eric James Devroe, Malden, MA (US); Sriram Kosuri, Cambridge, MA (US); David Arthur Berry, Brookline, MA (US); Noubar Boghos Afeyan, Lexington, MA (US); Frank Anthony Skraly, Watertown, MA (US); Dan Eric Robertson, Belmont, MA (US); Brian Green, Watertown, MA (US); Christian Perry Ridley, Acton, MA (US)

(73) Assignee: Joule Unlimited, Inc., Cambridge, MA (US)

( * ) Notice: Subject to any disclaimer, the term of this patent is extended or adjusted under 35 U.S.C. 154(b) by 82 days.

(21) Appl. No.: 12/268,406

(22) Filed: Nov. 10, 2008

(65) Prior Publication Data

US 2009/0203070 A1    Aug. 13, 2009

Related U.S. Application Data

(60) Provisional application No. 60/987,046, filed on Nov. 10, 2007, provisional application No. 61/032,169, filed on Feb. 28, 2008, provisional application No. 61/090,933, filed on Aug. 22, 2008.

(51) Int. Cl.
*C12N 15/31* (2006.01)
*C12N 15/52* (2006.01)
*C12N 15/82* (2006.01)

(52) U.S. Cl. .................................. 435/252.3; 435/471

(58) Field of Classification Search ........................ None
See application file for complete search history.

(56) References Cited

U.S. PATENT DOCUMENTS

| | | | |
|---|---|---|---|
| 5,565,333 A | 10/1996 | Devauchelle et al. | |
| 6,306,639 B1 | 10/2001 | Woods et al. | |
| 6,429,002 B1 | 8/2002 | Ben-Bassat et al. | |
| 6,699,696 B2 | 3/2004 | Woods et al. | |
| 6,806,066 B2 | 10/2004 | Bayer et al. | |
| 7,026,527 B2 * | 4/2006 | Falco et al. | 800/278 |
| 7,045,320 B2 | 5/2006 | Iwatani et al. | |
| 7,235,385 B2 | 6/2007 | Chan et al. | |
| 7,314,974 B2 | 1/2008 | Cao et al. | |
| 2003/0104375 A1 | 6/2003 | Delong et al. | |
| 2005/0196866 A1 | 9/2005 | San et al. | |
| 2005/0255568 A1 | 11/2005 | Bailey et al. | |
| 2008/0148432 A1 | 6/2008 | Abad | |
| 2008/0229451 A1 | 9/2008 | Cao et al. | |

FOREIGN PATENT DOCUMENTS

| | | |
|---|---|---|
| WO | WO 01/07626 | 2/2001 |
| WO | WO 2007/035579 | 3/2007 |
| WO | WO 2007/084477 | 7/2007 |
| WO | WO 2007/135188 | 11/2007 |
| WO | WO 2008/003078 | 1/2008 |
| WO | WO 2008/028019 A | 3/2008 |
| WO | WO 2008/137092 | 11/2008 |

OTHER PUBLICATIONS

PCT International Search Report and Written Opinion, PCT Application No. PCT/US2008/083056, Jul. 30, 2009, seventeen pages.
Nedbal, L., et al., "E-photosynthesis: a comprehensive modeling approach to understand chlorophyll fluorescence transients and other complex dynamic features of photosynthesis in fluctuating light," Photosynth Res. Jul. 2007; 93(1-3), pp. 223-234.
Salvucci, M.E., et al., "Inhibition of photosynthesis by heat stress: the activation state of Rubisco as a limiting factor in photosynthesis," Physiologia Plantarum, Feb. 2004, 120(2), pp. 179-186.
Greene, D.N., et al., "Artificially evolved Synechococcus PCC6301 Rubisco variants exhibit improvements in folding and catalytic efficiency," Biochem J., Jun. 2007, vol. 404(3), pp. 517-524.
Walter JM, et al., "Light-powering *Escherichia coli* with proteorhodopsin," PNAS, 2007, pp. 2408-2412, vol. 104, No. 7.
Hallam, S.J., et al., "Pathways of carbon assimilation and ammonia oxidation suggested by environmental genomic analyses of marine Crenarchaeota," PLoS Biol., Apr. 2006, vol. 4(4), e95, pp. 0520-0536.
Herter, S., et al., "Autotrophic CO(2) fixation by *Chloroflexus aurantiacus*: study of glyoxylate formation and assimilation via the 3-hydroxypropionate cycle," J Bacteriol. Jul. 2001;183(14):4305-16.
Liang, S.T., et al., "Activities of Constitutive Promoters in *Escherichia coli*," J. Mol Biol (1999). vol. 292, No. 1, pp. 19-37.
Alper, H., et al., "Tuning genetic control through promoter engineering." PNAS, Sep. 6, 2005, vol. 102, No. 36, pp. 12678-12783.
Jensen, P.R., et al., "The sequence of spacers between the consensus sequences modulates the strength of prokaryotic promoters," Appl Environ Microbiol (1998). 64(I): pp. 82-87.
Mijakovic, I., et al., "Tunable promoters in system biology," Curr. Opin. Biotechnol. (2005), vol. 16, pp. 329-335.
De Mey, M., et al., "Construction and model-based analysis of a promoter library from *E. coli*: an indispensable tool for metabolic engineering." BMC Biotechnology (2007) 7:34, pp. 1-14.
Khlebnikov, A., et al., "Homogeneous expression of the P(BAD) promoter in *Escherichia coli* by constitutive expression of the low-affinity high-capacity AraE transporter." Microbiology (2001), 147 (Pt 12): pp. 3241-3247.

(Continued)

*Primary Examiner*—Russell Kallis
(74) *Attorney, Agent, or Firm*—Fenwick & West LLP

(57) ABSTRACT

The present disclosure identifies pathways and mechanisms to confer improved industrial fitness on engineered organisms. It also discloses engineered organisms having improved industrial fitness. Synthetic biologic engineering modules are disclosed that provide for light capture, carbon dioxide fixation, NADH production, NADPH production, thermotolerance, pH tolerance, flue gas tolerance, salt tolerance, nutrient independence and near infrared absorbance. The disclosed engineered organisms can include one or more of these modules. Also provided are methods of using the engineered organism to produce carbon-based products of interest, biomass or pharmaceutical agents.

16 Claims, 39 Drawing Sheets

OTHER PUBLICATIONS

Figure 3:
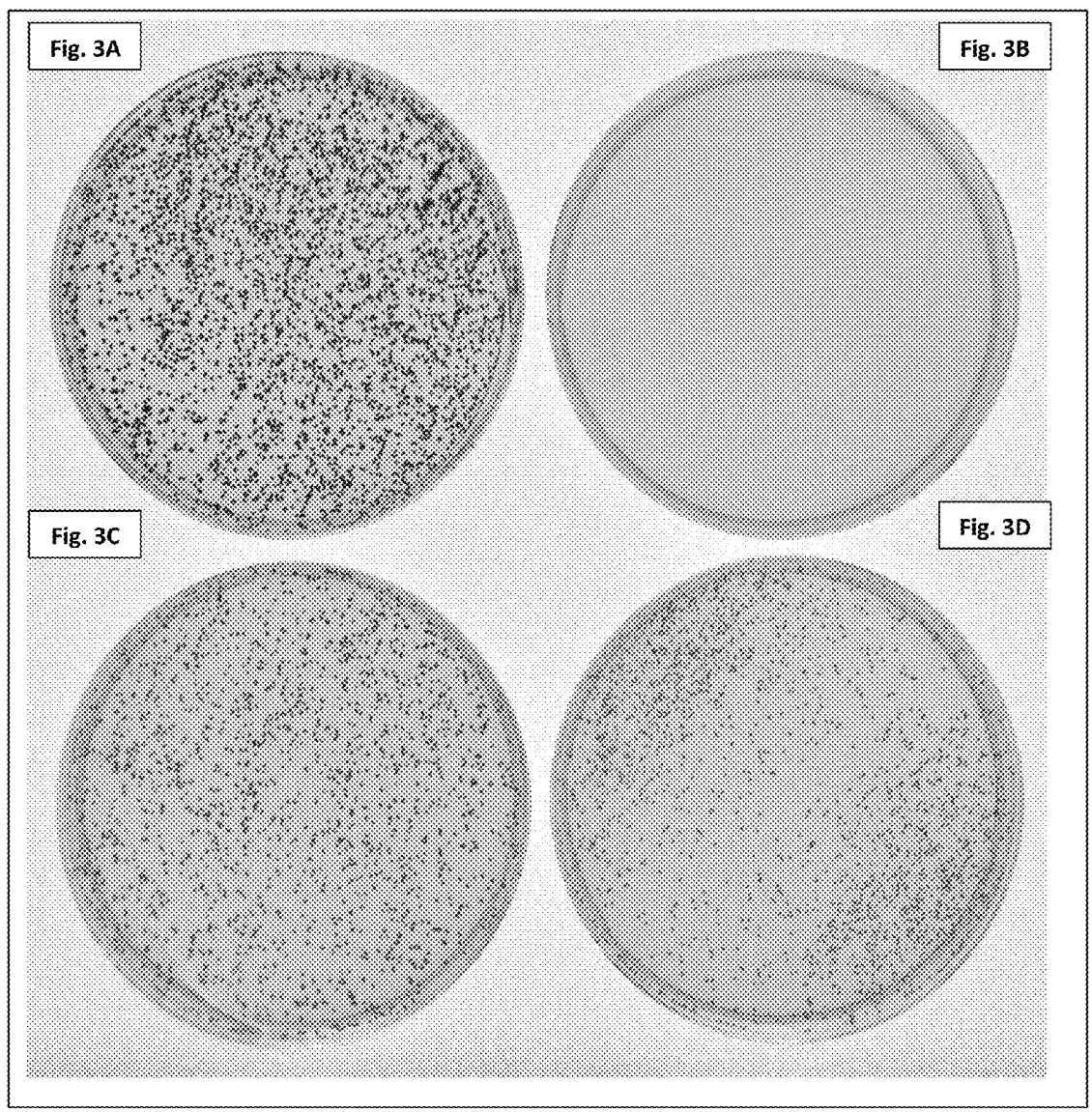

Haldimann, A., et al., "Use of new methods for construction of tightly regulated arabinose and rhamnose promoter fusions in studies of the *Escherichia coli* phosphate regulon," J Bacteriol (1998) 180: pp. 1277-1286.

Lee, S.K., et al., "A propionate-inducible expression system for enteric bacteria." Appl Environ Microbiol (2005). 71(11) pp. 6856-6862.

Gronenborn, B., "Overproduction of phage lambda repressor under control of the lac promoter of *Escherichia coli*." Mol Gen Genet (1976) 148, pp. 243-250.

De Boer, H.A., et al., "The tac promoter: a functional hybrid derived from the trp and lac promoters." PNAS, Jan. 1983, vol. 80, pp. 21-25.

Brosius, J., et al., "Spacing of the -10 and -35 regions in the tac promoter. Effect on its in vivo activity." J Biol Chem (1985), vol. 260, pp. 3539-3541.

Studier, F.W., et al., "Use of bacteriophage T7 RNA polymerase to direct selective high-level expression of cloned genes." J Mol Biol., 1986, vol. 189, pp. 113-130.

Skerra, A. "Use of the tetracycline promoter for the tightly regulated production of a murine antibody fragment in *Escherichia coli*" Gene (1994), vol. 151, pp. 131-135.

Shine, J., et al., "Determination of cistron specificity in bacterial ribosomes" Nature (1975) 254(5495), pp. 34-38.

De Boer, H.A., et al., "Portable Shine-Dalgarno regions; nucleotides between the Shine-Dalgarno sequence and the start codon effect the translation efficiency" Gene Amplif Anal (1983) vol. 3, pp. 103-116.

Mattanovich D, et al., "Optimization of recombinant gene expression in *Escherichia coli*." NY Acad Sci, 1996, pp. 182-190, vol. 782.

Xu, J., et al., "A polylinker-derived sequence, PL, highly increased translation efficiency in *Escherichia coli*." J Basic Microbiol (1999) 39(1), pp. 51-60.

Cebe, R., et al., "Rapid and easy thermodynamic optimization of 5'-end of mRNA dramatically increases the level of wild type protein expression in *Escherichia coli*." Protein Expr Purif (2006) 45(2), pp. 374-380.

Zhang, W., et al., "mRNA secondary structure at start AUG codon is a key limiting factor for human protein expression in *Escherichia coli*," Biochem Biophys Res Commun (2006), 349(1), pp. 69-78.

Voges, D., et al., "Analyzing and enhancing mRNA translational efficiency in an *Escherichia coli* in vitro expression system," Biochem Biophys Res Commun (2004), 318(2) pp. 601-614.

Deng, T., "Bacterial expression and purification of biologically active mouse c-Fos proteins by selective codon optimization" FEBS Lett (1997), 409(2), pp. 269-272.

Hale, R.S., et al., "Codon optimization of the gene encoding a domain from human type 1 neurofibromin protein results in a threefold improvement in expression level in *Escherichia coli*." Protein Expr Purif (1998) 12(2), pp. 185-188.

Berger and Kimmel, Guide to Molecular Cloning Techniques, Methods in Enzymology vol. 152 Academic Press, Inc., San Diego, Calif. (1987).

Sambrook, J., et al. (1989) Molecular Cloning—A Laboratory Manual (2nd ed.) vol. 1-3, Cold Spring Harbor Laboratory, Cold Spring Harbor Press, N.Y.

Ausubel, F. M. et al., eds., Current Protocols in Molecular Biology, Current Protocols, a joint venture between Greene Publishing Associates, Inc. and John Wiley & Sons, Inc., (through and including the 1997 Supplement).

Datsenko, K.A., et al., "One-step inactivation of chromosomal genes in *E. coli* K-12 using PCR Products" PNAS (2000), 97: pp. 6640-6645.

Link, A.J., et al. "Methods for generating precise deletions and insertions in the genome of wild-type *Escherichia coli*: Application to open reading frame characterization." J Bacteriol (1997), vol. 179, pp. 6228-6237.

Baba, T., et al., "Construction of *Escherichia coli* K-12 in-frame, single gene knockout mutants: the Keio collection." Mol Syst Biol (2006) vol. 2, pp. 1-11.

Tischer, B.K., et al., "Two-step red-mediated recombination for versatile high-efficiency markerless DNA manipulation in *Escherichia coli*." Biotechniques (2006), vol. 40(2), pp. 191-197.

Mckenzie, G.J., et al., "Fast, easy and efficient: site-specific insertion of transgenes into enterobacterial chromosomes using Tn7 without need for selection of the insertion event." BMC Microbiol (2006) vol. 6:39, pp. 1-7.

Camilli, A., et al., "Bacterial small-molecule signaling pathways," Science, Feb. 2006, vol. 311, pp. 1113-1116.

Venturi, V., "Regulation of quorum sensing in Pseudomonas," FEMS Microbiology Review, Nov. 18, 2005, vol. 30, pp. 274-291.

Reading, N.C., et al., "Quorum sensing: the many languages of bacteria," FEMS Microbiol. Lett., vol. 254, pp. 1-11 (2006).

Murli, S., et al., "A Role for the umuDC Gene Products of *Escherichia coli* in Increasing Resistance to DNA Damage in Stationary Phase by Inhibiting the Transition to Exponential Growth" Journal of Bacteriology, Feb. 2000, p. 1127-1135, vol. 182, No. 4.

Deshpande, M., "Ethanol Production from Cellulose by Coupled Saccharification/Fermentation using *Saccharomyces cerevisiae* and Cellulose Complex from Sclerotium rolfsil UV-8 Mutant," Appl. Biochem. Biotechnol (1992), vol. 36, pp. 227-234.

Alton, N.K., et al., "Nucleotide sequence analysis of the chloramphenicol resistance transposon Tn9," Nature, Dec. 1979, vol. 282, pp. 864-869.

De Wet, J. R., et al., "Firefly Luciferase gene: structure and expression in mammalian cells," Mol. And Cell. Biol., Feb. 1987, vol. 7, No. 2, pp. 725-737.

Engerbrecht, J., et al., "Identification of genes and gene products necessary for bacterial bioluminescence," PNAS Jul. 1, 1984 vol. 81 No. 13, pp. 4154-4158.

Baldwin, T., et al., "Cloning of the luciferase structural genes from Vibrio harveyi and expression of bioluminescence in *Escherichia coli*," Biochemistry, Jul. 31, 1984, vol. 23, pp. 3663-3667.

Toh, Y., et al. "Isolation and characterization of a rat liver alkaline phosphatase gene," (1989) Eur. J. Biochem., vol. 182, pp. 231-238.

Hall, C.V., et al. Expression and regulation of *Escherichia coli* lacZ gene fusions in mammalian cells. J. Mol. Appl. Gen. 1983, vol. 2, pp. 101-109.

Cullen, B., et al., "Secreted Placental Alkaline Phosphatase as a Eukaryotic Reporter Gene," Methods in Enzymol., (1992), vol. 216, pp. 362-368.

Sheng, M., et al., "The Regulation and Funtion of c-fos and Other Immediate Early Genes in the Nervous System," Neuron (1990), vol. 4, pp. 477-485.

Keasling, J. D. et al., "New tools for metabolic engineering of *Escherichia coli*," in Metabolic Engineering, Publisher Marcel Dekker, New York, Nym 1999, pp. 97-111.

Keasling, J. D. "Gene-expression tools for the metabolic engineering of bacteria," Trends in Biotechnology, Nov. 1999, vol. 17, pp. 452-460.

Martin, V. J. J., et al., "Redesigning cells for production of complex organic molecules," ASM News, 2002, vol. 68, No. 7, pp. 336-343.

Henry, C. S., et al., "Genome-Scale Thermodynamic Analysis of *Escherichia coli* Metabolism," Biophys. J., 90, pp. 1453-1461, 2006.

Pramanik, J., et al., "A stoichiometric model of *Escherichia coli* metabolism: incorporation of growth-rate dependent biomass composition and mechanistic energy requirements." Biotechnol. Bioeng. 1997, vol. 56, pp. 398-421.

Pramanik, J., et al., "Effect of *Escherichia coli* Biomass composition and metabolic fluxes predicted by a stoichiometric model." Biotechnol. Bioeng., 1998, vol. 60, pp. 230-238.

Pramanik, J., et al., "A flux-based stoichiometric model of enhanced biological phosphorus removal metabolism." Wat. Sci. Tech., 1998, vol. 37, pp. 609-613.

Pramanik, J., et al., "Development and validation of a flux-based stoichiometric model for enhanced biological phosphorus removal metabolism." Water Res., 1999, vol. 33, No. 2, pp. 462-476.

Crawford, R.L., "Lignin biodegradation and transformation," John Wiley and Sons, New York., 1981.

Futterer, O., et al., "Genome sequence of Picrophilus torridus and its implications for life around pH 0," PNAS USA, 2004, vol. 101, No. 24, pp. 9091-9096.

Sabehi, G., et al., "New Insights into Metabolic Properties of Marine Bacteria Encoding Proteorhodopsins," PLoS Biol, 2005, vol. 3:8, e273, pp. 1409-1417.

Rajalahti, T., et al., "Proteins in Different Synechocystis Compartemnts Have Distinguishing N-Terminal Features: A Combined Proteomics and Multivariate Sequence Analysis," J. Proteome Res., vol. 6 (2007) pp. 2420-2434.
Beja, O., et al., "Proteorhodopsine phototrophy in the ocean," Nature, Jun. 14, 2001, vol. 444, pp. 786-789.
Bielawski, J. P., et al. "Darwinian adaptation of proteorhodopsin to different light intensities in the marine environment," Proc. Natl. Acad. Sci. USA, Oct. 12, 2004, vol. 101 pp. 14824-14829.
Li X., et al. "Fast noninvasive activation and inhibition of neural and network activity by vertebrate phodopsin and green algae channelrhodopsin," Proc. Natl. Acad. Sci. USA, Dec. 2005, vol. 102 pp. 17816-17821.
Bertani, G., "Studies on lysogenesis. I. The mode of phage liberation by lysogenic Escherichia coli" J. Bacteriol (1951) vol. 62, pp. 293-300.
J. R. Broach, E. W. Jones, and J. R. Pringle (eds.), "The Molecular and Cellular Biology of the Yeast Saccharomyces," vol. 1. Genome Dynamics, Protein Synthesis, and Energetics. Cold Spring Harbor Laboratory Press, Cold Spring Harbor, New York, 1991.
E. W. Jones, J. R. Pringle, and J. R. Broach, (eds.), "The Molecular and Cellular Biology of the Yeast Saccharomyces," vol. 2. Gene Expression. Cold Spring Harbor Laboratory Press, Cold Spring Harbor, New York, 1992.
J. R. Pringle, J. R. Broach, and E. W. Jones, (eds.), "The Molecular and Cellular Biology of the Yeast Saccharomyces," vol. 3. Cell cycle and Cell Biology. Cold Spring Harbor Laboratory Press, Cold Spring Harbor, New York, 1997.
Nacken, V., et al., "Probing the limits of expression levels by varying promoter strength and plasmid copy number in Saccharomyces cerevisiae." Gene (1996), vol. 175(1-2), pp. 253-260.
Okumura, H., et al., "Construction of plasmid vector and genetic transformation system for Acetobacter aceti." Agril. Biol. Chem (1985) vol. 49 pp. 1011-1017.
PCT Invitation to Pay Additional Fees and, Where Applicable, Protest Fee and Communication Relating to the Results of the Partial International Search Report, PCT/US2008/083056, Apr. 7, 2009,11 Pages.
Nakano, S., et al., "Putative ABC Transporter Responsible for Acetic Acid Resistance in Acetobacter aceti." Appl. And Environ. Microbiol (2006), vol. 72(1) pp. 497-505.
Martinez, A., et al, "Proteorhodopsin photosystem gene expression enables photophosphorylation in a heterologous host." PNAS, Mar. 27, 2007, vol. 104, No. 13, pp. 5590-5595.
Oesterhelt, D., et al., "Rhodopsin-like protein from the purple membrane of Halobacterium halobium." Nature (1971), vol. 233, pp. 149-152.
HG, W.V., et al., "Genome sequence of Halobacterium species NRC-1." PNAS (2000) vol. 97(22) pp. 12176-22181.
Hoffmann, A., et al., "Photoactive mitochondria: in vivo transfer of a light-driven proton pump into the inner mitochondrial membrane of Schizosaccharomyces pombe." Proc. Natl. Acad. Sci (1994), vol. 91, pp. 9367-9371.
Ihara, K. et al., "Evolution of the archael rhodopsins: evolution rate changes by gene duplication and functional differentiation." J Mol Biol (1999) vol. 285 pp. 163-174.
Kamo N, et al., "A light-driven proton pump from Haloterrigena turkmenica: functional expression in Escherichia coli membrane and coupling with a H+ co-transporter," Biochem. Biophys. Res. Commun., 2006, pp. 285-290, vol. 342, No. 2.
PCT International Search Report and Written Opinion, PCT/US2008/075899, Dec. 22, 2008, 25 Pages.
Waschuk SA, et al., "Leptosphaeria rhodopsin: Bacteriorhodopsin-like proton pump from a eukaryote," PNAS, 2005, pp. 6879-6883, vol. 102, No. 19.
Balashov SP, et al., "Xanthorhodopsin: A proton pump with a light harvesting cartenoid antenna," Science, 2005, pp. 2061-2064, vol. 309, No. 5743.
Mongodin, E.F., et al. "The genome of Salinibacter ubber: Convergence and gene exchange among hyperhalophilic bacteria and archaea." PNAS, Dec. 13, 2005, vol. 102, No. 50, pp. 18147-18152.
Neidhardt FC et al. Escherichia coli and Salmonella: cellular and molecular biology, vol. 1. ASM Press, Washington DC, 1996.

Claas, K., et al., "Lesions in the nuo operon, encoding NADH dehydrogenase complex I, prevent PurF-independent thiamine synthesis and reduce flux through the oxidative pentose phosphate pathway in Salmonella enterica serovar typhimurum," J Bacteriol (2000) vol. 182(1) pp. 228-232.
Beja, O., et al., "Bacterial Rhodopsin: Evidence for a New Type of Phototrophy in the Sea," Science, Sep. 15, 2000, vol. 289, pp. 1902-1906.
Parikh, M. R., et al., "Directed Evolution of RuBisCO hypermorphs through genetic selection in engineered E. coli. Protein Engineering," Protein Engineering, Design & Selection, 2006, vol. 19, No. 3, pp. 113-119.
Dietzler, D. N., et al., "Rates of Glycogen Synthesis and the Cellular Levels of ATP and FDP During Exponential Growth and Nitrogen-Limited Stationary Phase of Escherichia coli W4597 (K)" Arch. Biochem. Biophys. 1973, vol. 156, pp. 684-693.
Herter, S., et al., "Autotrophic CO2 fixation by Chloroflexus aurantiacus: study of glyoxylate formation and assimilation via the 3-hydroxypropionate cycle." Journal of Bacteriology, Jul. 2001, vol. 183(14) pp. 4305-4316.
Yun, N.R., et al., "The Genes for anabolic 2-oxoglutarate: Ferredoxin oxidoreductase from Hydrogenobacter thermophilus TK6," Biochem Biophys Res Communic (2001), vol. 282 (2) pp. 589-594.
Yun, N.R., et al. "A novel five-subunit-type 2-oxoglutalate:ferredoxin oxidoreductases from Hydrogenobacter thermophilus TK-6," Biochem Biophys Res Communic (2002), vol. 292(1) pp. 280-286.
Roberts, D.L., et al., "The reductive acetyl-CoA Pathway: Sequence and heterologous expression of active methyltetrahydrofolate:corrinoid/Urib -sulfur protein methyltransferase from Clostridium thermoaceticum." J. Bacteriol (1994), vol. 176(19), pp. 6127-6130.
Chung, T., et al., "Glyoxylate bypass operon of Escherichia coli: cloning and determination of the functional map." J Bacteriol (1988) vol. 170(1), pp. 386-392.
Hers, H.G., et al., "Gluconeogenesis and related aspects of glycolysis." Ann Rev. Biochem (1983) vol. 52 pp. 617-653.
Furdui, C., et al., "The role of pyruvate ferredoxin oxidoreductase in pyruvate synthesis during autotrophic growth by the Woods-Ljungdahl pathway" J. Biol. Chem (2000), vol. 275(37) pp. 28494-28499.
Dupuis, A., et al., "Genetic disruption of the respiratory NADH-ubiquinone reductase of Rhodobacter capsulatus leads to an unexpected photosynthesis-negative phenotype" FEMS Microbiol Lett (1997), vol. 149, pp. 107-114.
Dupuis, A., et al., "Distal genes of the nuo operon of Rhodobacter capsulatus equivalent to the mitochondrial ND subunits are all essential for the biogenesis of the respiratory NADH-ubiquinone oxidoreductase," J. Mol. Microbiol (1998) vol. 28 pp. 531-541.
Kabir, MM, et al., "Fermentation characteristics and protein expression patterns in a recombinant Escherichia coli mutant lacking phosphoglucose isomerase for poly (3-hydroxybutyrate) production." Appl. Microbiology Biotechnology, 2003, pp. 244-255, vol. 62.
Kabir MM, et al., "Gene expression patterns for metabolic pathway in pgi knockout Escherichia coli with and without phb genes based on RT-PCR," J. Biotechnology, 2003, pp. 11-31, vol. 105 No. 1-2.
Vadali, R., et al., "Applicability of CoA/acetyl-CoA manipulation system to enhance isoamyl acetate production in Escherichia coli," Metab Eng., 2004, pp. 294-299, vol. 6.
Shaw, J., et al., "Metabolic Engineering of the Xylose Utilizing Thermophile Thermoanaerobacterium saccharolyticum JW/SL-YS485 for Ethanol Production." Presented at AICHE Annual Meeting, Aug. 28, 2006, 22 pages.
Atsumi S., et al., "Non-fermentative pathways for synthesis of branched-chain higher alcohols as biofuels," Nature, 2008, p. 86-90, vol. 451.
Mutsuda M, et al., "Translation initiation of cyanobacterial rbcS mRNAs requires the 38-kDa ribosomal protein S1 but not the Shine-Dalgarno sequence," J Biol Chem, 2006, pp. 38314-38321, vol. 281, No. 50.
Mussgnug JH, et al., "Engineering photosynthetic light capture: impacts on improved solar energy to biomass conversion," Plant Biotechnology Journal, 2007, pp. 802-814, vol. 5, No. 6.

Tamoi M, et al., "Carbon metabolism in the Calvin cycle." Plant Biotechnology, 2005, pp. 355-360, vol. 22.

Kimura A, et al., "Protection of the Oxygen-Evolving Machinery by the Extrinsic Proteins of Photosystem II is Essential for Development of Cellular Thermotolerance in Synechocystis sp. PCC 6803," Plant Cell Physiol., 2002, pp. 932-938, vol. 43, No. 8.

Nakamoto H, et al., "Targeted inactivation of the hrcA repressor gene in cyanobacteria," FEBS Lett., 2003, pp. 57-62, vol. 549, No. 1-3.

Yang X, et al., "Genetic engineering of the biosynthesis of glycinebetaine enhances thermotolerance of photosystem II in tobacco plants," Plant, 2007, pp. 719-733, vol. 225, No. 3.

Waditee R, et al., "Genes for direct methylation of glycine provide high levels of glycinebetaine and abiotic-stress tolerance in *Synechococcus* and *Arabidopsis*," Proc Natl Acad Sci., 2005, pp. 1318-1323, vol. 102, No. 5.

Ohta H, et al., "Identification of genes expressed in response to acid stress in Synechocystis sp. PCC 6803 using DNA microarrays," Photosynth Res., 2005, pp. 225-230, vol. 84, No. 1-3.

Friedrich T., et al., "Proteorhodopsin is a light-driven proton pump with variable vectoriality," Journal of Molecular Biology, Aug. 30, 2002, pp. 821-838, vol. 321, No. 5.

Kim S., et al., "Screening and characterization of proteorhodopsin color-tuning mutations in *Escherichia* colo with endogenous retinal synthesis," Biochemica Et Biophysica Acta., Jun. 1, 2008, pp. 504-513, vol. 1777, No. 6.

Gourdon et al., "Optimized in vitro and in vivo expression of proteorhodopsin: A seven-transmembrane proton pump," Protein Expression and Purification, Nov. 20, 2007, pp. 103-113, vol. 58, No. 1.

Fuhrman J., et al., "Opinion Proteorhodopsins: an array of physiological roles?" Nature Reviews Microbiology, pp. 488-494, vol. 6, No. 6. (Jun. 2008).

Sineshcheko, O., et al., "Two rhodopsins mediate phototaxis to low- and high-intensity light in *Chlamydomonas reinhardtii*" Proceedings of the National Academy of Sciences of the United States of America, vol. 99, No. 13, Jun. 25, 2002, pp. 8689-8694.

Katsiou, E., et al., "Heterologous expression of genes encoding bacterial light-harvesting complex II in *Rhodobacter capsulatus* and *Rhodovulum sulfidophilum*" Microbiological Research, vol. 153, No. 3, Nov. 1998, pp. 189-204.

Du, C., et al., "Construction of a genetically engineered microorganism for C02 fixation using a *Rhodopseudomonas/Escherichia coli* shuttle Vector," FEMS Microbiology Letters, vol. 225, No. 1, Aug. 8, 2003, pp. 69-73.

Hohenfeld, I., et al., "Purification of histidine tagged bacteriorhodopsin, pharaonis halorhodopsin and pharaonis sensory rhodopsin II functionally expressed in *Escherichia coli*," FEBS Letter, 1999, vol. 442, pp. 198-202.

* cited by examiner

TABLE 1 GENES TO BE OVEREXPRESSED

| Module | Target | EC (If Relevant) | Exemplary Gene Name | Organism | Locus/Accession | Alternates |
|---|---|---|---|---|---|---|
| Carbon Fixation | 3-Hydroxypropionate cycle | 6.4.1.2 | Acetyl-CoA carboxylase (subunit alpha) | Escherichia coli | AAA70370 | Homo sapiens [ACACA, NC000017.9] |
| Carbon Fixation | 3-Hydroxypropionate cycle | 6.4.1.2 | Acetyl-CoA carboxylase (subunit beta) | Escherichia coli | AAA23807 | Arabidopsis thaliana [AtCg00500] |
| Carbon Fixation | 3-Hydroxypropionate cycle | 6.4.1.2 | Biotin-carboxyl carrier protein (accB) | Escherichia coli | JW3223 | Bacillus halodurans [BH1132], Vibrio cholerae [EAZ76879.1 or A5E_0311] |
| Carbon Fixation | 3-Hydroxypropionate cycle | 6.4.1.2 | biotin-carboxylase | Escherichia coli | AAA23748 | Photobacterium profundum 3TCK [EAS42088.1 or 90325619] |
| Carbon Fixation | 3-Hydroxypropionate cycle | 1.1.1.59 | malonyl-CoA reductase | Chloroflexus aurantiacus | AY530019 | only one I can find via BLASTp |
| Carbon Fixation | 3-Hydroxypropionate cycle | | 3-hydroxypropionyl-CoA synthase | Chloroflexus aurantiacus | AF445079 | BLASTp homolog 2702 bits, 81% positive, 4% gaps IDs AMP-dependent synthetase and ligase [ABQ91563.1] from Roseiflexus sp RS-1. |
| Carbon Fixation | 3-Hydroxypropionate cycle | 6.4.1.3 | propionyl-CoA carboxylase (subunit alpha) | Roseobacter denitrificans | RD1_2032 | Homo sapiens mitochondrial PCCA gene [X14608], Mus musculus PCCA gene [AY046947] |
| Carbon Fixation | 3-Hydroxypropionate cycle | 6.4.1.3 | propionyl-CoA carboxylase (subunit beta) | Roseobacter denitrificans | RD1_2028 | Rhodococcus erythropolis [AAB80770.1], Homo sapiens mitochondrial PCCB [X73424] |

Figure 1

| Module | Target | EC (If Relevant) | Exemplary Gene Name | Organism | Locus/ Accession | Alternates |
|---|---|---|---|---|---|---|
| Carbon Fixation | 3-Hydroxypropionate cycle | 5.1.99.1 | methylmalonyl-CoA epimerase | Rhodobacter sphaeroides | CP000661 | Homo sapiens MCEE [AF364547] |
| Carbon Fixation | 3-Hydroxypropionate cycle | 5.1.99.2 | methylmalonyl-CoA mutase | Escherichia coli | NC000913.2 | Homo sapiens MUT [M65131] |
| Carbon Fixation | 3-Hydroxypropionate cycle | | succinyl-CoA:L-malate CoA transferase (subunit alpha) | Chloroflexus aurantiacus | DQ472736.1 | Chloroflexus aggregans DSM 0485 [ZP_01516527.1 or EAV09800.1] |
| Carbon Fixation | 3-Hydroxypropionate cycle | | succinyl-CoA:L-malate CoA transferase (subunit beta) | Chloroflexus aurantiacus | DQ472737.1 | Chloroflexus aggregans DSM 9485 [ZP_01516526.1 or EAV09799.1] |
| Carbon Fixation | 3-Hydroxypropionate cycle | 1.3.1.6 | fumarate reductase - frdA - flavoprotein subunit | Escherichia coli | J01611, AAA23437.1 | Salmonella enterica subsp. Enterica serovar fumarate reductase NP_458782.1 or Klebsiella pneumoniae ABR79907.1 |
| Carbon Fixation | 3-Hydroxypropionate cycle | 1.3.1.6 | fumarate reductase iron-sulfur subunit- frdb | Escherichia coli | J01611, EAY46226.1 | Salmonella typhimurium LT2 succinate dehydrogenase [NP_463206.1] |
| Carbon Fixation | 3-Hydroxypropionate cycle | 1.3.1.6 | g15 subunit [fumarate reductase subunit c] | Escherichia coli | J01611; NP_290787.1 | Shigella flexneri 2a str. 301 [NP_710021.1], Klebsiella pneumoniae ABR79905.1] |
| Carbon Fixation | 3-Hydroxypropionate cycle | 1.3.1.6 | g13 subunit [fumarate reductase subunit D] | Escherichia coli | J01611, NP_757087.1 | Salmonella enterica [YP_153210.1], Photorhabdus luminescens [NP_931317.1] |
| Carbon Fixation | 3-Hydroxypropionate cycle | 4.2.1.2 | fumarate hydratase - class I aerobic (fumA) | Escherichia coli | CAA25204 | E. coli class I anaerobic fumarate hydratase (fumB) AAA23827 or class II (fumC) CAA27698 |

Figure 1 (Continued)

| Module | Target | EC (If Relevant) | Exemplary Gene Name | Organism | Locus/ Accession | Alternates |
|---|---|---|---|---|---|---|
| Carbon Fixation | 3-Hydroxypropionate cycle | 4.1.3.24 | L-malyl-CoA lyase | Roseobacter denitrificans | NC_008209.1 | Silicibacter pomeroyi DSS-3 citrate lyase putative [Ided from BLASTp] [YP_166806.1] and alpha proteobacterium HTCC2255 [ZP_01447127.1] |
| Carbon Fixation | Reductive TCA | 2.3.3.8 | ATP-citrate lyase, subunit 1 | Chlorobium tepidum | CT1089 | Chlorobium limicola [BAB21375.1], Chlorobium ferrooxidans DSM 13031 [ZP_01385848.1] |
| Carbon Fixation | Reductive TCA | 2.3.3.8 | ATP-citrate lyase, subunit 2 | Chlorobium tepidum | CT1088 | Chlorobium limicola [BAB21376.1], Chlorobium phaeobacteroides [YP_911761.1], Chlorobium ferrooxidans [ZP_01385849.1]. |
| Carbon Fixation | Reductive TCA | | citryl-CoA synthase (large subunit | Hydrogenobacter thermophilus | BAD17844 | Aquifex aeolicus [O67330], Leptospirillum sp. Group II UBA [A3ERU1] |
| Carbon Fixation | Reductive TCA | | citryl-CoA synthase (small subunit) | Hydrogenobacter thermophilus | BAD17846 | Aquifex aeolicus [NP_214297.1], Leptospirillum sp Group II UBA [EAY57418.1] |
| Carbon Fixation | Reductive TCA | | citryl-CoA ligase | Hydrogenobacter thermophilus | BAD17841 | Aquifex aeolicus [NP_213101.], Hydrogenobacter hydrogenophilus [ABI50086.1] |
| Carbon Fixation | Reductive TCA | 1.1.1.37 | malate dehydrogenase | Chlorobium tepidum | CAA56810 | Prosthecochloris vibrioformis [CAA56809.1], Pelodictyon luteolum DSM 273 [YP_375410.1] |
| Carbon Fixation | Reductive TCA | 4.2.1.2 | fumarase hydratase (aerobic isozyme, fumA) | Escherichia coli | JW1604 | E. coli class I anaerobic isozyme fumB (JW4083) and class II fumC (JW1603) |

Figure 1 (Continued)

| Module | Target | EC (If Relevant) | Exemplary Gene Name | Organism | Locus/ Accession | Alternates |
|---|---|---|---|---|---|---|
| Carbon Fixation | Reductive TCA | 1.3.99.1 | succinate dehydrogenase (flavoprotein subunit - SdhA) | Escherichia coli | NP_415251 | Enterobacter sp. 638 [YP_001175956.1], Serratia proteamaculans [ZP_01538596.1] |
| Carbon Fixation | Reductive TCA | 1.3.99.1 | SdhB iron-sulfur subunit | Escherichia coli | NP_415252 | Salmonella enterica [YP_151223.1], Yersinia enterocolitica [YP_001007133.1] |
| Carbon Fixation | Reductive TCA | 1.3.99.1 | SdhC membrane anchor subunit | Escherichia coli | NP_415249 | Enterobacter sp. 638 [ABP59903.1], Yersinia frederiksenii [ZP_00828037.1] |
| Carbon Fixation | Reductive TCA | 1.3.99.1 | SdhD membrane anchor subunit | Escherichia coli | NP_415250 | Enterobacter sp. 638 [YP_001175955.1], Klebsiella pneumoniae [YP_001334402.1] |
| Carbon Fixation | Reductive TCA | 6.2.1.5 | succinyl-CoA synthetase subunit alpha (sucD) | Escherichia coli | AAA23900 | Chlorobium tepidum [AAM71515] |
| Carbon Fixation | Reductive TCA | 6.2.1.5 | succinyl-CoA synthetase subunit beta (sucC) | Escherichia coli | AAA23899 | Chlorobium tepidum [AAM71626] |
| Carbon Fixation | Reductive TCA | 1.2.7.3 | alpha-ketoglutarate subunit alpha -korA | Hydrogenobacter thermophilus | AB046568:46-1869 | Chlorobium limicola DSM 245; Accession numbers EAM42575, EAM42574, EAM42853, EAM42852. |
| Carbon Fixation | Reductive TCA | 1.2.7.3 | alpha-ketoglutarate subunit beta -korB | Hydrogenobacter thermophilus | AB046568:1883-2770 | Hydrogenobacter thermophilus TK-6, forDABGE 5-gene cluster |
| Carbon Fixation | Reductive TCA | 1.1.1.42 | Isocitrate dehydrogenase - NADP dependent | Chlorobium limicola | EAM42635 | Synechococcus sp WH 8102, icd, accession CAE06681 |
| Carbon Fixation | Reductive TCA | 1.1.1.41 | isocitrate dehydrogenase - NAD depend. Subunit 1 | Saccharomyces cerevisiae | YNL037C | |
| Carbon Fixation | Reductive TCA | 1.1.1.41 | isocitrate dehydrogenase - NAD depend. Subunit 2 | Saccharomyces cerevisiae | YOR136W | |

Figure 1 (Continued)

| Module | Target | EC (If Relevant) | Exemplary Gene Name | Organism | Locus/Accession | Alternates |
|---|---|---|---|---|---|---|
| Carbon Fixation | Reductive TCA | 4.2.1.3 | aconitate hydratase 1 (acnA) | Escherichia coli | b1276 | |
| Carbon Fixation | Reductive TCA | 4.2.1.3 | aconitate hydratase 2 (acnB) | Escherichia coli | b0118 | |
| Carbon Fixation | Reductive TCA | 1.2.7.1 | Pyruvate synthase, subunit A porA | Clostridium tetani E88 | AAO36986 | |
| Carbon Fixation | Reductive TCA | 1.2.7.1 | Pyruvate synthase, subunit B porB | Clostridium tetani E88 | AAO36985 | |
| Carbon Fixation | Reductive TCA | 1.2.7.1 | Pyruvate synthase, subunit C porC | Clostridium tetani E88 | AAO36988 | |
| Carbon Fixation | Reductive TCA | 1.2.7.1 | Pyruvate synthase, subunit D porD | Clostridium tetani E88 | AAO36987 | |
| Carbon Fixation | Reductive TCA | 2.7.9.2 | Phosphoenolpyruvate synthase - ppsA | Escherichia coli | AAA2431 | Aquifex aeolicus VF5 ppsA (AAC07865). |
| Carbon Fixation | Reductive TCA | 4.1.1.31 | PEP carboxylase, ppC | Escherichia coli | CAA29332 | |
| Carbon Fixation | Woods-Ljungdahl | 1.2.1.4.3 | NADP-dependent formate dehydrogenase - subunit A Mt-fdhA | Moorella thermoacetica | AAB18330 | |
| Carbon Fixation | Woods-Ljungdahl | 1.2.1.4.3 | NADP-dependent formate dehydrogenase - subunit B Mt-fdhB | Moorella thermoacetica | AAB18329 | |
| Carbon Fixation | Woods-Ljungdahl | 6.3.4.3 | formate tetrahydrofolate ligase | Clostridium acidi-urici | M21507 | AAB49329 from Streptococcus mutans (protein = Q59925) or the Q8XHL4 protein from Clostridium perfingens (coded_by="complement(BA0000 16.3:2825121..2826791). |

Figure 1 (Continued)

| Module | Target | EC (If Relevant) | Exemplary Gene Name | Organism | Locus/ Accession | Alternates |
|---|---|---|---|---|---|---|
| Carbon Fixation | Woods-Ljungdahl | 3.5.4.9 and 1.5.1.5 | Methenyltetrahydrofolate cyclohydrolase | Escherichia coli | AAA23803 | ABC19825 (folD) from Moorella thermoacetica, AAO36126 from Clostridium tetani, and BAB81529 from Clostridium perfingens All are bifunctional folD enzymes. |
| Carbon Fixation | Woods-Ljungdahl | 1.5.1.20 | methylene tetrahydrofolate reductase, metF | Escherichia coli | CAA24747 | AAC23094 from Haemophilus influenzae, or CAA30531 from Salmonella typhimurium. |
| Carbon Fixation | Woods-Ljungdahl | - | 5-methyltetrahydrofolate corrinoid/iron sulfur protein methyltransferase, acsE | Moorella thermoacetica | AAA53548 | acsE from Carboxydothermus hydrogenoformans locus ABB15216. |
| Carbon Fixation | Woods-Ljungdahl | 1.2.7.4/ 1.2.99.2 | Carbon monoxide dehydrogenase/acetyl-CoA synthase - subunit alpha | Moorella thermoacetica | AAA23229 | Carboxydothermus hydrogenoformase [YP_360060] |
| Carbon Fixation | Woods-Ljungdahl | 1.2.7.4/ 1.2.99.2 | Carbon monoxide dehydrogenase/acetyl-CoA synthase - subunit beta | Moorella thermoacetica | AAA23228 | |
| Carbon Fixation | Glyoxylate Shunt | 2.3.3.9 | malate synthase - aceB | Escherichia coli | JW3974 | E. coli JW2943 locus malate synthase G (glcB) |
| Carbon Fixation | Glyoxylate Shunt | 4.1.3.1 | isocitrate lyase - aceA | Escherichia coli | JW3975 | |
| Carbon Fixation | Glyoxylate Shunt | 1.1.1.37 | malate dehydrogenase | Escherichia coli | JW3205 | |
| Carbon Fixation | Gluconeogenesis | 6.4.4.1 | pyruvate carboxylase | Saccharomyces cerevisiae | YGL062W | |
| Carbon Fixation | Gluconeogenesis | 4.1.1.49 | phosphoenolpyruvate carboxykinase | Escherichia coli | JW3366 | |
| Carbon Fixation | Gluconeogenesis | 3.1.3.11 | fructose-1,6-bisphosphatase | Escherichia coli | JW4191 | |

Figure 1 (Continued)

| Module | Target | EC (If Relevant) | Exemplary Gene Name | Organism | Locus/ Accession | Alternates |
|---|---|---|---|---|---|---|
| Carbon Fixation | Gluconeogenesis | 3.1.3.68 | glucose-6-phosphatase - dog1 | Saccharomyces cerevisiae | YHR044C | Saccharomyces cerevisiae YHR043C locus, dog2 |
| Carbon Fixation | pyruvate synthesis | 1.2.7.1 | pyruvate ferredoxin:oxidoreductase with pyruvate synthase activity | Moorella thermoaceticum | Moth_0064 | |
| Carbon Fixation | Calvin cycle | EC 4.1.2.13 | Fructose-1,6-bisphosphate aldolase – class I (Fda) | Synechocystis sp PCC 6803 | NP_441723 | Synechococcus sp. WH 7805 = ZP_01124026 |
| Carbon Fixation | Calvin cycle | EC 4.1.2.13 | Fructose-1,6-bisphosphate aldolase – class II (FbaA) | Synechocystis sp PCC 6803 | BAA10184 | |
| Carbon Fixation | Calvin cycle | EC 1.2.1.13 | glyceraldehyde-3-phosphate dehydrogenase (GAPDH), cbbG | Prochlorococcus marinus | NP_875968 | |
| Carbon Fixation | Calvin cycle | EC 2.7.1.19 | Phosphoribulokinase (PrkA) | Chlamydomonas reinhardtii | AAA33090 | Prochlorococcus marinus = NP_894365 |
| Carbon Fixation | Calvin cycle | | CP12 | Thermosynechoco ccus elongatus BP-1 | BAC09372 | Chlamydomonas reinhardtii = CAO03469; Synechococcus elongatus PCC 6301 = BAD79451 |
| Carbon Fixation | Calvin cycle | EC 2.2.1.1 | Transketolase (TktA) | Synechocystis sp. PCC 6803 | YP_171693 | |
| Carbon Fixation | Calvin cycle | EC 3.1.3.11 | Fructose-1,6-bisphosphatase (Fbp) | Synechocystis sp. PCC 6803 | NP_441738 | |
| Carbon Fixation | Calvin cycle | EC 5.1.3.1 | Pentose-5-phosphate-3-epimerase (Rpe) | Synechocystis sp. PCC 6803 | YP_171630 | |
| Carbon Fixation | Calvin cycle | EC 4.1.2.13 | Sedoheptulose-1,7-bisphosphate aldolase (RpaA) | Thermosynechoco ccus elongatus BP-1 | NP_681166 | |

Figure 1 (Continued)

| Module | Target | EC (If Relevant) | Exemplary Gene Name | Organism | Locus/Accession | Alternates |
|---|---|---|---|---|---|---|
| Carbon Fixation | Calvin cycle | EC 3.1.3.37 | Sedoheptulose-1,7-bisphosphatase (SBPase) | Chlamydomonas reinhardtii | CAA52439 | |
| Carbon Fixation | Calvin cycle | EC 5.3.1.6 | Ribose 5-phosphate isomerase (RpiA) | Synechococcus elongatus PCC 6301 | YP_171649 | |
| Carbon Fixation | Calvin cycle | EC 2.7.2.3 | phosphoglycerate kinase | Synechococcus elongatus PCC 6301 | BAD78623 | |
| Carbon Fixation | Calvin cycle | EC 5.3.1.1 | triosephosphate isomerase, tpiA | Synechocystis sp PCC 6803 | Q59994 | |
| Carbon Fixation | Calvin cycle | EC 4.1.1.39 | Ribulose-1,5-bisphosphate carboxylase/oxygenase (RubisCo) - small subunit - cbbS | Synechococcus sp WH7803 | AAB48081 | |
| Carbon Fixation | Calvin cycle | EC 4.1.1.39 | Ribulose-1,5-bisphosphate carboxylase/oxygenase (RubisCo) - large subunit cbbL | Synechococcus sp WH7803 | AAB8080 | |
| Carbon Fixation | Calvin cycle | EC 4.1.1.39 | Ribulose-1,5-bisphosphate carbyxlase/oxygenase - small subunit (RbcS) | Synechococcus elongatus PCC 6301 | YP_170839 | |
| Carbon Fixation | Calvin cycle | EC 4.1.1.39 | Ribulose-1,5-bisphosphate carbyxlase/oxygenase - large subunit (RbcL) | Synechococcus elongatus PCC 6301 | YP_170840 | |
| Carbon Fixation | Calvin cycle | EC 4.1.1.39 | Ribulose-1,5-bisphosphate carbyxlase/oxygenase - small subunit (CbbS) | Rhodobacter sphaeroides | P27998 | |

Figure 1 (Continued)

| Module | Target | EC (If Relevant) | Exemplary Gene Name | Organism | Locus/Accession | Alternates |
|---|---|---|---|---|---|---|
| Carbon Fixation | Calvin cycle | EC 4.1.1.39 | Ribulose-1,5-bisphosphate carbyxlase/oxygenase- large subunit (CbbL) | Rhodobacter sphaeroides | P27997 | |
| Carbon Fixation | Calvin cycle | EC 4.1.1.39 | Ribulose-1,5-bisphosphate carbyxlase/oxygenase (CbbM) | Rhodobacter sphaeroides | P29278 | |
| Carbon Fixation | Calvin cycle | EC 4.1.1.39 | Ribulose-1,5-bisphosphate carbyxlase/oxygenase (RbcL) | Methanocaldococcus jannaschii | Q58632 | |
| Carbon Fixation | Calvin cycle | | Rubisco activase | Synechococcus sp. JA-3-3Ab | ABC98646 | Chlamydomonas reinhardtii (EDP04194) |
| Carbon Fixation | Carbon-acetyl-CoA flux | EC 2.7.1.33 | pantothenate kinase (panK) | Synechococcus sp. JA-3-3Ab | YP_473820 | |
| Carbon Fixation | Carbon-acetyl-CoA flux | EC 1.2.4.1 | Pyruvate, dehydrogenase, alpha subunit (pdhA) | Synechococcus PCC 6301 | YP_172860 | |
| Carbon Fixation | Carbon-acetyl-CoA flux | EC 1.2.4.1 | Pyruvate, dehydrogenase, alpha subunit (pdhB) | Synechococcus PCC 6301 | YP_172072 | |
| Flue gas tolerance | NOx tolerance | | Multicopper oxidase type 1 (NirK) | Nitrosomonas europaea | NP_840998 | |
| Flue gas tolerance | NOx tolerance | | Multicopper oxidase type 1 (ncgA) | Nitrosomonas europaea | NP_841001 | |
| Flue gas tolerance | NOx tolerance | | Cytochrome c, class I (ncgB) | Nitrosomonas europaea | NP_841000 | |
| Flue gas tolerance | NOx tolerance | | Cytochrome c, class IC (ncgC) | Nitrosomonas europaea | NP_840999 | |
| Flue gas tolerance | SOx tolerance | EC 4.2.99.8 and 2.5.1.47 | cysteine synthase A (cysK) | Synechococcus PCC 7942 | YP_398721 | |

Figure 1 (Continued)

| Module | Target | EC (If Relevant) | Exemplary Gene Name | Organism | Locus/ Accession | Alternates |
|---|---|---|---|---|---|---|
| Flue gas tolerance | SOx tolerance | EC 1.15.1.1 | superoxide dismutase (sodA) | Synechocystis PCC 6803 | NP_441347 | |
| Flue gas tolerance | SOx tolerance | EC 1.11.16 | catalase (katG) | Synechocystis PCC 6803 | NP_441295 | |
| Light capture | light->PMF | | Proteorhodopsin | Uncultured marine bacterium HF10_19P19 | ABL60988 | HOT 0m1 gene (AF349978), the HOT 75m4 gene (AF349981), the palE6 gene (AF350002), and the SAR86 gene from eBAC31A08 (AAG10475). |
| Light capture | light->PMF | | bacteriorhodopsin | Halobacterium species NRC-1 | NP_280292 | Halobacterium salinarum gene (V00474) |
| Light capture | light->PMF | | deltarhodopsin | Haloterrigena sp arg-4 | AB009620 | Alternatives include the variant described in Kamo N et al, BBRC 2006, from Haloterrigena turkmenica, which differs only in 2 positions compared to AB009620 (no accession number was ever deposited) |
| Light capture | light->PMF | | xanthorhodopsin | Salinibacter ruber DSM 13855 | ABC44767 | |
| Light capture | light->PMF | | opsin | Leptosphaeria maculans | AAG01180 | |
| Light capture | Retinal biosynthesis | 5.3.3.2 | Isopentenyl-diphosphate delta-isomerase | Uncultured marine bacterium HF10_19P19 | ABL60982 | Alternatives include E. coli (JW2857) and Rhodococcus capsulatus (CAA77535.1) |
| Light capture | Retinal biosynthesis | 1.14.99.36 | 15,15'-beta-carotene dioxygenase | Uncultured marine bacterium HF10_19P19 | ABL60983 | Homo sapiens (AAG15380) and Mus musculus (AJ278064) |

Figure 1 (Continued)

| Module | Target | EC (If Relevant) | Exemplary Gene Name | Organism | Locus/Accession | Alternates |
|---|---|---|---|---|---|---|
| Light capture | Retinal biosynthesis | | Lycopene cyclase | Uncultured marine bacterium HF10_19P19 | ABL60984 | cruA gene from Synechococcus sp PCC 7002 (EF529626) and cruP from same species (EF529627), and crtY from Streptomyces coelicolor (SCJ12.03, or NC_003888.3) |
| Light capture | Retinal biosynthesis | | Phytoene synthase | Uncultured marine bacterium HF10_19P19 | ABL60985 | Streptomyces coelicolor A3(2) [locus SCO0187] or Prochlorococcus marinus crtB [Pro0166 or NC_005042.1] |
| Light capture | Retinal biosynthesis | | Phytoene dehydrogenase | Uncultured marine bacterium HF10_19P19 | ABL60986 | Prochlorococcus marinus [Pro0167] or Thermosynechococcus elongatus BP-1 [tll1561] |
| Light capture | Retinal biosynthesis | | Geranylgeranyl pyrophosphate synthetase | Uncultured marine bacterium HF10_19P19 | ABL60987 | Rhodobacter sphaeroides 2.4.1 crtE gene [RSP_0265] and Arabidopsis thaliana GGPS3 [AT3G14550] |
| Light capture | Salinixanthin | | beta-carotene ketolase | Salinibacter ruber DSM 13855 | SRU_1502 | CrtO genes include Rhodococcus erythropolis (AY705709), Deinococcus radiodurans R1 (pir-1E75561), and Gloeobacter violaceus PCC 7421 [gvip239]. |
| Light capture | ATP synthesis | 3.6.3.14 | F0 sector of membrane-bound ATP synthase, subunit a (Aconsisting of atpB) | Escherichia coli | NP_418194 | |
| Light capture | ATP synthesis | 3.6.3.14 | F0 sector of membrane-bound ATP synthase, subunit c (AtpE) | Escherichia coli | NP_418193 | |

Figure 1 (Continued)

| Module | Target | EC (If Relevant) | Exemplary Gene Name | Organism | Locus/ Accession | Alternates |
|---|---|---|---|---|---|---|
| Light capture | ATP synthesis | 3.6.3.14 | F0 sector of membrane-bound ATP synthase, subunit b (AtpF) | Escherichia coli | NP_418192 | |
| Light capture | ATP synthesis | 3.6.3.14 | F1 sector of membrane-bound ATP synthase, alpha subunit (AtpA) | Escherichia coli | NP_418190 | |
| Light capture | ATP synthesis | 3.6.3.14 | F1 sector of membrane-bound ATP synthase, epsilon subunit (AtpC) | Escherichia coli | NP_418187 | |
| Light capture | ATP synthesis | 3.6.3.14 | F1 sector of membrane-bound ATP synthase, beta subunit (AtpD), I atpD (Locus NP_418188) | Escherichia coli | NP_418188 | |
| Light capture | ATP synthesis | 3.6.3.14 | F1 sector of membrane-bound ATP synthase, gamma subunit (AtpG) | Escherichia coli | NP_418189 | |
| Light capture | ATP synthesis | 3.6.3.14 | F1 sector of membrane-bound ATP synthase, delta subunit, (AtpH) | Escherichia coli | NP_418191 | |
| Nutrient independence | Nitrate/Nitrite Assimilation | | ABC-type nitrate/nitrite transport system substrate-binding protein (nrtA) | Synechococcus elongatus PCC 6301 | YP_171021 | |
| Nutrient independence | Nitrate/Nitrite Assimilation | | ABC-type nitrate/nitrite transport system permease protein (nrtB) | Synechococcus elongatus PCC 6301 | YP_171022 | |
| Nutrient independence | Nitrate/Nitrite Assimilation | | ABC-type nitrate/nitrite transport system ATP-binding protein (nrtC) | Synechococcus elongatus PCC 6301 | YP_171023 | |

Figure 1 (Continued)

| Module | Target | EC (If Relevant) | Exemplary Gene Name | Organism | Locus/Accession | Alternates |
|---|---|---|---|---|---|---|
| Nutrient independence | Nitrate/Nitrite Assimilation | | ABC-type nitrate/nitrite transport system ATP-binding protein (nrtD) | Synechococcus elongatus PCC 6301 | YP_171024 | |
| Nutrient independence | Nitrate/Nitrite Assimilation | | Nitrite/Nitrate permease (nrtP) | Synechococcus sp. PCC 7002 | AAD45941 | |
| Nutrient independence | Nitrate/Nitrite assimilation - Nitrite tolerance | | Multicopper oxidase type 1 (NirK) | Nitrosomonas europaea | NP_840998 | |
| Nutrient independence | Nitrate/Nitrite assimilation - Nitrite tolerance | | Multicopper oxidase type 1 (ncgA) | Nitrosomonas europaea | NP_841001 | |
| Nutrient independence | Nitrate/Nitrite assimilation - Nitrite tolerance | | Cytochrome c, class I (ncgB) | Nitrosomonas europaea | NP_841000 | |
| Nutrient independence | Nitrate/Nitrite assimilation - Nitrite tolerance | | Cytochrome c, class IC (ncgC) | Nitrosomonas europaea | NP_840999 | |
| Nutrient independence | Nitrate/Nitrite Assimilation | | nitrite reductase (nirA) | Synechococcus sp. PCC 7002 | AAK49018 | |
| Nutrient independence | Nitrate/Nitrite Assimilation | | nitrate reductase (narB) | Synechococcus sp. PCC 7002 | AAD45942 | |
| Nutrient independence | Ammonia Assimilation | | high affinity ammonium/methylammonium permease (amt1) | Synechocystis sp. PCC 6803 | NP_442561 | |
| Nutrient independence | Ammonia Assimilation | | ammonium/methylammonium permease (amt2) | Synechocystis sp. PCC 6803 | NP_440272 | |
| Nutrient independence | Ammonia Assimilation | | ammonium/methylammonium permease (amt3) | Synechocystis sp. PCC 6803 | NP_442793 | |

Figure 1 (Continued)

| Module | Target | EC (If Relevant) | Exemplary Gene Name | Organism | Locus/ Accession | Alternates |
|---|---|---|---|---|---|---|
| Nutrient independence | Urea Assimilation | 3.5.1.5 | urea amidohydrolase, gamma subunit (ureA) | Synechococcus sp. WH 7805 | AAC61500.1 | |
| Nutrient independence | Urea Assimilation | 3.5.1.5 | urea amidohydrolase, beta subunit (ureB) | Synechococcus sp. WH 7805 | AAC61501.1 | |
| Nutrient independence | Urea Assimilation | 3.5.1.5 | urea amidohydrolase, alpha subunit (ureC) | Synechococcus sp. WH 7805 | AAC61502.1 | |
| Nutrient independence | Urea Assimilation | | urease accessory protein (ureD) | Synechococcus sp. WH 7805 | AAC61499.1 | |
| Nutrient independence | Urea Assimilation | | urease accessory protein (ureE) | Synechococcus sp. WH 7805 | AAC61498.1 | |
| Nutrient independence | Urea Assimilation | | urease accessory protein (ureF) | Synechococcus sp. WH 7805 | AAC61497.1 | |
| Nutrient independence | Urea Assimilation | | urease accessory protein (ureG) | Synechococcus sp. WH 7805 | AAC61496.1 | |
| Nutrient independence | Urea Assimilation | | ABC-type, high-affinity urea permease, periplasmic domain (urtA) | Nostoc sp. PCC 7120 | CAB70948.1 | |
| Nutrient independence | Urea Assimilation | | ABC-type, high-affinity urea permease, membrane domain (urtB) | Nostoc sp. PCC 7120 | CAB70949.1 | |
| Nutrient independence | Urea Assimilation | | ABC-type, high-affinity urea permease, membrane domain (urtC) | Nostoc sp. PCC 7120 | CAB70950.1 | |
| Nutrient independence | Urea Assimilation | | ABC-type, high-affinity urea permease, ATP binding domain (urtD) | Nostoc sp. PCC 7120 | CAB70951.1 | |

Figure 1 (Continued)

| Module | Target | EC (If Relevant) | Exemplary Gene Name | Organism | Locus/ Accession | Alternates |
|---|---|---|---|---|---|---|
| Nutrient independence | Urea Assimilation | | ABC-type, high-affinity urea permease, ATP binding domain (urtE) | Nostoc sp. PCC 7120 | CAB70952.1 | |
| Nutrient independence | Nitrogen Fixation | | FeMo cofactor biosynthesis protein (nifB) | Nostoc. Sp PCC 7120 | NP_485557 | |
| Nutrient independence | Nitrogen Fixation | | [4Fe-4S] ferredoxin (fdxN) | Nostoc. Sp PCC 7120 | BA000019.2 | |
| Nutrient independence | Nitrogen Fixation | 2.8.1.7 | L-Cysteine desulfurase (nifS) | Nostoc. Sp PCC 7120 | NP_485499 | |
| Nutrient independence | Nitrogen Fixation | | Fe cluster accessory protein (nifU) | Nostoc. Sp PCC 7120 | NP_485498 | |
| Nutrient independence | Nitrogen Fixation | 1.18.6.1 | Nitrogenase - Fe subunit (nifH) | Nostoc. Sp PCC 7120 | NP_485497 | |
| Nutrient independence | Nitrogen Fixation | 1.18.6.1 | Nitrogenase - alpha subunit (nifD) | Nostoc. Sp PCC 7120 | NP_485484 | |
| Nutrient independence | Nitrogen Fixation | 1.18.6.1 | Nitrogenase - beta subunit (nifK) | Nostoc. Sp PCC 7120 | NP_485483 | |
| Nutrient independence | Nitrogen Fixation | | FeMo cofactor accessory protein (nifE) | Nostoc. Sp PCC 7120 | NP_485481 | |
| Nutrient independence | Nitrogen Fixation | | FeMo cofactor accessory protein (nifN) | Nostoc. Sp PCC 7120 | NP_485480 | |
| Nutrient independence | Nitrogen Fixation | | FeMo cofactor accessory protein (nifX) | Nostoc. Sp PCC 7120 | NP_485479 | |
| Nutrient independence | Nitrogen Fixation | | FeMo cofactor accessory protein (nifW) | Nostoc. Sp PCC 7120 | NP_485476 | |

Figure 1 (Continued)

| Module | Target | EC (If Relevant) | Exemplary Gene Name | Organism | Locus/ Accession | Alternates |
|---|---|---|---|---|---|---|
| Nutrient independence | Nitrogen Fixation | | FeMo cofactor accessory protein (hesA) | Nostoc. Sp PCC 7120 | NP_485475 | |
| Nutrient independence | Nitrogen Fixation | | FeS cluster cofactory assembly accessory protein (hesB) | Nostoc. Sp PCC 7120 | NP_485474 | |
| Nutrient independence | Nitrogen Fixation | | nitrogen-fixation-specific ferredoxin (FdxH) | Nostoc. Sp PCC 7120 | NP_485473 | |
| Nutrient independence | Nitrogen Fixation | 1.2.7.1 | pyruvate:flavodoxin oxidoreductase (nifJ) | Nostoc. Sp PCC 7120 | NP_486843 | |
| Nutrient independence | Nitrogen Fixation | 2.3.3.14 | homocitrate synthase (nifV) | Nostoc. Sp PCC 7120 | NP_485450 | |
| Nutrient independence | Nitrogen Fixation | | FeMo cofactor accessory protein (nifZ) | Nostoc. Sp PCC 7120 | NP_485451 | |
| Nutrient independence | Nitrogen Fixation | | FeMo cofactor accessory protein (nifT) | Nostoc. Sp PCC 7120 | NP_485452 | |
| Nutrient independence | Vitamin B12 independence | EC 2.1.1.14 | 5-methyltetrahydropteroyltriglutamate-homocysteine methyltransferase (metE) | Thermotoga maritima | NP_229090 | |
| Nutrient independence | Vitamin B12 independence | | Ribonucleoside-diphosphate reductase, alpha subunit (nrdA) | Synechocystis sp. PCC 6803 | NP_441654 | |
| Nutrient independence | Vitamin B12 independence | | Ribonucleoside-diphosphate reductase, beta subunit (nrdB) | Synechocystis sp. PCC 6804 | NP_443040 | |
| Nutrient independence | Vitamin B12 biosynthesis | 2.1.1.107 | uroporphyrin-III C-methyltransferase; cobaltochelatase (cysG) | S. typhimurium | NP_462380 | |

Figure 1 (Continued)

| Module | Target | EC (If Relevant) | Exemplary Gene Name | Organism | Locus/ Accession | Alternates |
|---|---|---|---|---|---|---|
| Nutrient independence | Vitamin B12 biosynthesis | 4.99.1.3 | Sirohydrochlorin cobaltochelatase (cbiK) | S. typhimurium | NP_460970 | |
| Nutrient independence | Vitamin B12 biosynthesis | 2.1.1.130 | precorrin-2 C20-methyltransferase (cbiL) | S. typhimurium | NP_460969 | |
| Nutrient independence | Vitamin B12 biosynthesis | 2.1.1.131 | Precorrin-3B methylase (cbiH) | S. typhimurium | NP_460972 | |
| Nutrient independence | Vitamin B12 biosynthesis | | Bifunctional CbiG/precorrin methyltransferase (cbiG) | S. typhimurium | NP_460973 | |
| Nutrient independence | Vitamin B12 biosynthesis | 2.1.1.133 | precorrin-4 C11-methyltransferase (cbiF) | S. typhimurium | NP_460974 | |
| Nutrient independence | Vitamin B12 biosynthesis | | Cobalamin biosynthesis protein (cbiD) | S. typhimurium | NP_460977 | |
| Nutrient independence | Vitamin B12 biosynthesis | 1.3.1.54 | NADPH-dependent precorrin-6A reductase (cbiJ) | S. typhimurium | NP_460971 | |
| Nutrient independence | Vitamin B12 biosynthesis | 2.1.1.132 | precorrin-6B C5,15-methyltransferase (cbiE) | S. typhimurium | NP_460976 | |
| Nutrient independence | Vitamin B12 biosynthesis | 2.1.1.132 | precorrin-6B C12 decarboxylase (cbiT) | S. typhimurium | NP_460975 | |
| Nutrient independence | Vitamin B12 biosynthesis | 5.4.1.2 | Precorrin-8X-methylmutase (cbiC) | S. typhimurium | NP_460978 | |
| Nutrient independence | Vitamin B12 biosynthesis | 6.3.1.- | cobyrinic acid A,C-diamide synthase (cbiA) | S. typhimurium | NP_460980 | |
| Nutrient independence | Vitamin B12 biosynthesis | 2.5.1.17 | Cob(I)yrinic acid a,c-diamide adenosyltransferase (btuR) | S. typhimurium | NP_460677 | |
| Nutrient independence | Vitamin B12 biosynthesis | 6.3.5.10 | cobyrinic acid synthase (cbiP) | S. typhimurium | NP_460964 | |

Figure 1 (Continued)

| Module | Target | EC (If Relevant) | Exemplary Gene Name | Organism | Locus/ Accession | Alternates |
|---|---|---|---|---|---|---|
| Nutrient independence | Vitamin B12 biosynthesis | 4.1.1.81 | cobyric acid decarboxylase (cobD) | S. typhimurium | NP_459636 | |
| Nutrient independence | Vitamin B12 biosynthesis | 6.3.1.10 | Adenosylcobinamide-phosphate synthase (cbiB) | S. typhimurium | NP_460979 | |
| Nutrient independence | Vitamin B12 biosynthesis | 3.1.3.73 | alpha ribazole-5'-P phosphatase (cobC) | S. typhimurium | NP_459635 | |
| Nutrient independence | Vitamin B12 biosynthesis | 2.7.8.26 | cobalamin(5'-phosphate) synthase (cobS) | S. typhimurium | NP_460962 | |
| Nutrient independence | Vitamin B12 biosynthesis | 2.7.7.62 | cobinamide phosphate guanylyl transferase (cobU) | S. typhimurium | NP_460963 | |
| Nutrient independence | Vitamin B12 biosynthesis | 2.4.2.21 | nicotinate-nucleotide dimethylbenzimidazole-P phophoribosyl transferase (cobT) | S. typhimurium | NP_460961 | |
| Nutrient independence | Vitamin B12 biosynthesis - Co2+ transport | | ABC-type Co2+ transport system, permease component | S. typhimurium | NP_460968 | |
| Nutrient independence | Vitamin B12 biosynthesis - Co2+ transport | | ABC-type cobalt transport system, periplasmic component | S. typhimurium | NP_460967 | |
| Nutrient independence | Vitamin B12 biosynthesis - Co2+ transport | | ABC-type cobalt transport system, permease component | S. typhimurium | NP_461989 | |
| pH tolerance | | EC 1.15.1.1 | superoxide dismutase (sodA) | Synechocystis PCC 6803 | NP_441347 | |
| pH tolerance | | EC 4.1.1.15 | glutamate decarboxylase A (GadA), | Escherichia coli | NP_417974 | |

Figure 1 (Continued)

| Module | Target | EC (If Relevant) | Exemplary Gene Name | Organism | Locus/Accession | Alternates |
|---|---|---|---|---|---|---|
| pH tolerance | | EC 4.1.1.15 | Glutamate decarboxylase beta (GadB) | Escherichia coli | NP_416010 | |
| pH tolerance | | | glutamate:gamma-aminobutyric acid antiporter (GadC) | Escherichia coli | NP_416009 | |
| pH tolerance | | EC 4.1.1.19 | biodegradative arginine decarboxylase (AdiA) | Escherichia coli | NP_418541 | |
| pH tolerance | | | arginine:agmatin antiporter (AdiC) | Escherichia coli | NP_418539 | |
| pH tolerance | | | Chloride channel protein (EriC) | Escherichia coli | NP_414697 | |
| pH tolerance | | | Chloride channel protein (MriT) | Escherichia coli | NP_416109 | |
| pH tolerance | | | Chaperone protein dnaK2 (DnaK) | Synechocystis PCC 6803 | NP_441989 | |
| pH tolerance | | | DNA-directed RNA polymerase, sigma subunit (sll0306) | Synechocystis PCC 6803 | NP_441950 | |
| pH tolerance | | | Zn-dependent protease (sll0528) | Synechocystis PCC 6803 | NP_442805 | |
| pH tolerance | | | metal-dependent phosphoesterase (sll0549) | Synechocystis PCC 6803 | NP_442414 | |
| pH tolerance | | | Acid-stress tolerance protein (sll0846) | Synechocystis PCC 6803 | NP_441124 | |
| pH tolerance | | | Acid-stress related membrane protein (sll0939) | Synechocystis PCC 6803 | NP_440194 | |

Figure 1 (Continued)

| Module | Target | EC (If Relevant) | Exemplary Gene Name | Organism | Locus/ Accession | Alternates |
|---|---|---|---|---|---|---|
| pH tolerance | | | Acid-stress tolerance protein (sll1086) | Synechocystis PCC 6803 | NP_441667 | |
| pH tolerance | | | Acid-stress tolerance protein (sll1483) | Synechocystis PCC 6803 | NP_442911 | |
| pH tolerance | | | 16.6 kDa small heat shock protein, molecular chaperone (sll1514) | Synechocystis PCC 6803 | NP_440316 | |
| pH tolerance | | EC 2.7.7.13 | mannose-1-phosphate guanyltransferase (sll1558) | Synechocystis PCC 6803 | NP_441699 | |
| pH tolerance | | | RNA polymerase sigma factor (sll2012) | Synechocystis PCC 6803 | NP_441031 | |
| pH tolerance | | EC 3.4.21.102 | carboxyl-terminal processing protease (slr0008) | Synechocystis PCC 6803 | NP_442119 | |
| pH tolerance | | | molecular chaperone (slr0093) | Synechocystis PCC 6803 | NP_442496 | |
| pH tolerance | | | Acid-stress tolerance protein (slr0270), | Synechocystis PCC 6803 | NP_441273 | |
| pH tolerance | | | Geranylgeranyl pyrophosphate synthase (slr0611) | Synechocystis PCC 6803 | NP_439899 | |
| pH tolerance | | | Acid-stress tolerance protein (slr0967) | Synechocystis PCC 6803 | NP_440193 | |
| pH tolerance | | | CheY-like receiver (slr1214) | Synechocystis PCC 6803 | NP_440716 | |
| pH tolerance | | | Signal transduction histidine kinase (slr1285) | Synechocystis PCC 6803 | NP_441610 | |

Figure 1 (Continued)

| Module | Target | EC (If Relevant) | Exemplary Gene Name | Organism | Locus/ Accession | Alternates |
|---|---|---|---|---|---|---|
| pH tolerance | | | Acid-stress tolerance protein (slr1413) | Synechocystis PCC 6803 | NP_440062 | |
| pH tolerance | | EC 1.15.1.1 | superoxide dismutase (slr1516) | Synechocystis PCC 6803 | NP_441347 | |
| pH tolerance | | | Acid-stress tolerance protein (slr1544) | Synechocystis PCC 6803 | NP_440790 | |
| pH tolerance | | | Acid-stress tolerance protein (slr1573) | Synechocystis PCC 6803 | NP_442902 | |
| pH tolerance | | | Acid-stress tolerance protein (slr1674) | Synechocystis PCC 6803 | NP_441676 | |
| pH tolerance | | | hydrogenase expression/formation protein (slr1675) | Synechocystis PCC 6803 | NP_441677 | |
| pH tolerance | | | Acid-stress tolerance protein (slr1676) | Synechocystis PCC 6803 | NP_441678 | |
| pH tolerance | | | Acid-stress tolerance protein (slr1687) | Synechocystis PCC 6803 | NP_441698 | |
| pH tolerance | | | Acid-stress tolerance protein (slr1915) | Synechocystis PCC 6803 | NP_440459 | |
| pH tolerance | | | Esterase (slr1916) | Synechocystis PCC 6803 | NP_440460 | |
| pH tolerance | | | Hydrogenase component protein (ssl3044) | Synechocystis PCC 6803 | NP_441697 | |
| pH tolerance | | | Acid-stress tolerance protein (ssl3769) | Synechocystis PCC 6803 | NP_441305 | |

Figure 1 (Continued)

| Module | Target | EC (If Relevant) | Exemplary Gene Name | Organism | Locus/ Accession | Alternates |
|---|---|---|---|---|---|---|
| pH tolerance | | | Acid-stress tolerance protein (ssr2016) | Synechocystis PCC 6803 | NP_440709 | |
| pH tolerance | | | Acid-stress tolerance protein (ssr2595) | Synechocystis PCC 6803 | NP_440789 | |
| Reducing power | NADH | 1.1.1.41 | NAD+-dependent isocitrate dehydrogenase - idh1 | Saccharomyces cerevisiae | YNL037C | |
| Reducing power | NADH | 1.1.1.41 | NAD+-dependent isocitrate dehydrogenase - idh2 | Saccharomyces cerevisiae | YOR136W | |
| Reducing power | NADH | 1.1.1.37 | malate dehydrogenase | Escherichia coli | JW3205 | |
| Reducing power | NADH | | NADH:ubiquinone oxidoreductase - OPERON (a-n), genes not listed individually | Rhodobacter capsulatus | AF029365 | |
| Reducing power | NADPH | 1.1.1.49 | glucose-6-phosphate dehydrogenase, zwf | Escherichia coli | JW1841 | |
| Reducing power | NADPH | 3.1.1.31 | 6-phosphogluconolactonase - pgl | Escherichia coli | JW0750 | |
| Reducing power | NADPH | 1.1.1.44 | 6-phosphogluconate dehydrogenase, gnd | Escherichia coli | JW2011 | |
| Reducing power | NADPH | 1.1.1.42 | NADP-dependent isocitrate dehydrogenase | Escherichia coli | JW1122 | |
| Reducing power | NADPH | 1.1.1.40 | NADP-dependent malic enyme | Escherichia coli | JW2447 | |
| Reducing power | NADPH | 1.6.1.1 | soluble pyridine nucleotide transhydrogenase | Escherichia coli | JW551 NP_418397.2 | |

Figure 1 (Continued)

| Module | Target | EC (If Relevant) | Exemplary Gene Name | Organism | Locus/Accession | Alternates |
|---|---|---|---|---|---|---|
| Reducing power | NADPH | | membrane-bound pyridine nucleotide transhydrogenase, subunit alpha, pntA | Escherichia coli | JW1595 | |
| Reducing power | NADPH | | membrane-bound pyridine nucleotide transhydrogenase, subunit beta, pntB | Escherichia coli | JW1594 | |
| Salt tolerance | | | Na+/H+ antiporter (apnhaP) | Aphanothece halophytica | BAB69459 | |
| Salt tolerance | | EC 1.11.16 | catalase (katG) | Synechocystis PCC 6803 | NP_441295 | |
| Salt tolerance | | | Salt and cadmium stress related protein (CW80Cd404) | Chlamydomonas sp. W80 | BAE53693 | |
| Salt tolerance | | | breast basic conserved (bbc1) | Chlamydomonas sp. W80 | BAA23724 | |
| Salt tolerance | betaine biosynthesis | | glycine sarcosine methyltransferase (ApGSMT) | Aphanothece halophytica | BAC56839 | |
| Salt tolerance | betaine biosynthesis | | dimethylglycine methyltransferase (ApDMT) | Aphanothece halophytica | BAC56840 | |
| Thermotolerance | Photosystem stability and repair | | Photosystem II manganese-stabilizing polypeptide (PsbO) | Synechocystis sp. PCC 6803 | NP_441796 | |
| Thermotolerance | Photosystem stability and repair | | PS II complex 12 kDa extrinsic protein (PsbU) | Synechocystis sp. PCC 6803 | NP_440167 | |
| Thermotolerance | Photosystem stability and repair | | Cytochrome c550 (PsbV) | Synechocystis sp. PCC 6803 | NP_441834 | |
| Thermotolerance | Protein folding | | 16.6 kDa small heat shock protein molecular chaperon (HspA) | Thermosynechococcus elongatus BP-1 | NP_681663 | |

Figure 1 (Continued)

| Module | Target | EC (If Relevant) | Exemplary Gene Name | Organism | Locus/ Accession | Alternates |
|---|---|---|---|---|---|---|
| Thermotolerance | Protein folding | | 60kD chaperonin 1 (GroEL-1) | Thermosynechoco ccus elongatus BP-1 | NP_680976 | |
| Thermotolerance | Protein folding | | 60kD chaperonin 2 (GroEL-2) | Thermosynechoco ccus elongatus BP-1 | NP_682202 | |
| Thermotolerance | Protein folding | | Co-chaperonin (GroES) | Thermosynechoco ccus elongatus BP-1 | NP_680977 | |
| Thermotolerance | Protein folding | | Endopeptidase (ClpB) | Thermosynechoco ccus elongatus BP-1 | NP_683242 | |
| Thermotolerance | betaine biosynthesis | | glycine sarcosine methyltransferase (ApGSMT) | Aphanothece halophytica | BAC56839 | |
| Thermotolerance | betaine biosynthesis | | dimethylglycine methyltransferase (ApDMT) | Aphanothece halophytica | BAC56840 | |

Figure 1 (Continued)

Table 2: Genes to be Downregulated or Knocked Out

| Module | Target | Relevance | EC (if relevant) | Exemplary Gene Name | Organism | Locus/Accession |
|---|---|---|---|---|---|---|
| Light harvesting | chlorophyll antenna size | plants, algae | n/a | tla1 | Chlamydomonas reinhardtii | AF534570 |
| Light harvesting | chlorophyll antenna size | plants, algae | n/a | LHCA1 | Chlamydomonas reinhardtii | AB122114 |
| Light harvesting | chlorophyll antenna size | plants, algae | n/a | LHCA2 | Chlamydomonas reinhardtii | AB122115 |
| Light harvesting | chlorophyll antenna size | plants, algae | n/a | LHCA3 | Chlamydomonas reinhardtii | AB122116 |
| Light harvesting | chlorophyll antenna size | plants, algae | n/a | LHCA4 | Chlamydomonas reinhardtii | AB122117 |
| Light harvesting | chlorophyll antenna size | plants, algae | n/a | LHCA5 | Chlamydomonas reinhardtii | AB122118 |
| Light harvesting | chlorophyll antenna size | plants, algae | n/a | LHCA6 | Chlamydomonas reinhardtii | AB122119 |
| Light harvesting | chlorophyll antenna size | plants, algae | n/a | LHCA7 | Chlamydomonas reinhardtii | AB122120 |
| Light harvesting | chlorophyll antenna size | plants, algae | n/a | LHCA8 | Chlamydomonas reinhardtii | scaffold_3:307726-310521 |
| Light harvesting | chlorophyll antenna size | plants, algae | n/a | LHCA9 | Chlamydomonas reinhardtii | AF244524 |
| Light harvesting | chlorophyll antenna size | plants, algae | n/a | LHCBM1 | Chlamydomonas reinhardtii | AF495473 |
| Light harvesting | chlorophyll antenna size | plants, algae | n/a | LHCBM2 | Chlamydomonas reinhardtii | AB051209 |
| Light harvesting | chlorophyll antenna size | plants, algae | n/a | LHCBM3 | Chlamydomonas reinhardtii | AB051208 |

Figure 2

| Module | Target | Relevance | EC (if relevant) | Exemplary Gene Name | Organism | Locus/Accession |
|---|---|---|---|---|---|---|
| Light harvesting | chlorophyll antenna size | plants, algae | n/a | LHCBM4 | Chlamydomonas reinhardtii | AF104630 |
| Light harvesting | chlorophyll antenna size | plants, algae | n/a | LHCBM5 | Chlamydomonas reinhardtii | AF104631 |
| Light harvesting | chlorophyll antenna size | plants, algae | n/a | LHCBM6 | Chlamydomonas reinhardtii | M24072.1 |
| Light harvesting | chlorophyll antenna size | plants, algae | n/a | LHCBM7 | Chlamydomonas reinhardtii | AF479779 |
| Light harvesting | chlorophyll antenna size | plants, algae | n/a | LHCBM8 | Chlamydomonas reinhardtii | AF330793 |
| Light harvesting | chlorophyll antenna size | plants, algae | n/a | LHCBM9 | Chlamydomonas reinhardtii | AF479778 |
| Light harvesting | chlorophyll antenna size | plants, algae | n/a | LHCBM10 | Chlamydomonas reinhardtii | AF479777 |
| Light harvesting | chlorophyll antenna size | plants, algae | n/a | LHCBM11 | Chlamydomonas reinhardtii | ? Can't locate |
| Light harvesting | chlorophyll antenna size | plants, algae | n/a | LHCB4 (cp29) | Chlamydomonas reinhardtii | AB051207 |
| Light harvesting | chlorophyll antenna size | plants, algae | n/a | LHCB5 (cp26) | Chlamydomonas reinhardtii | AB050007 |
| Light harvesting | bacteriochlorophyll antenna size | green sulfur and non-sulfur | n/a | bchK, BChl C synthase | Chlorobium tepidum | CT1992 |
| Light harvesting | bacteriochlorophyll antenna size | green sulfur and non-sulfur | n/a | bchQ, BChl c8 methyltransferase | Chlorobium tepidum | CT1777 |
| Light harvesting | bacteriochlorophyll antenna size | green sulfur and non-sulfur | n/a | bchR, BChl c12 methyltransferase | Chlorobium tepidum | CT1320 |
| Light harvesting | phycobillisome antenna size | cyanobacteria | n/a | cpcG2 | Synechocystis PCC 6803 | sll1471 |

Figure 2 (Continued)

| Module | Target | Relevance | EC (if relevant) | Exemplary Gene Name | Organism | Locus/Accession |
|---|---|---|---|---|---|---|
| Light harvesting | phycobillisome antenna size | cyanobacteria | n/a | apcE | Synechococcus PCC 6301 | YP_171895 |
| Light harvesting | phycobillisome antenna size | cyanobacteria | n/a | cpcG1 | Synechocystis PCC 6803 | slr2051 |
| Light harvesting | phycobillisome antenna size | cyanobacteria | n/a | CpcA, phycocyanin alpha subunit | Synechococcus PCC 6301 | syc0495 |
| Light harvesting | phycobillisome antenna size | cyanobacteria | n/a | CpcB, phycocyanin beta subunit | Synechococcus PCC 6301 | syc0496 |
| Light harvesting | phycobillisome antenna size | cyanobacteria | n/a | CpcC, phycobilisome rod linker peptide | Synechococcus PCC 6301 | syc0498 |
| Light harvesting | phycobillisome antenna size | cyanobacteria | n/a | CpcD, phycocyanin linker protein 9K | Synechococcus PCC 6301 | syc0497 |
| Light harvesting | phycobillisome antenna size | cyanobacteria | n/a | cpcE, phycobiliosme maturation protein | Synechococcus PCC 6301 | syc0494 |
| Light harvesting | phycobillisome antenna size | cyanobacteria | n/a | CpcG, phycobilisome rod-core linker polypeptide | Synechococcus PCC 6301 | syc2065 |
| Light harvesting | phycobillisome antenna size | cyanobacteria | n/a | CpcF, phycocyanin alpha-subunit phycocyanobilin lyase | Synechococcus PCC 6301 | YP_171203 |
| Light harvesting | Purple bacteria antenna size | purple sulfur and non-sulfur bacteria | n/a | pufA, Light-harvesting B875 alpha chain | Rhodobacter sphaeroides | YP_353331 |
| Light harvesting | Purple bacteria antenna size | purple sulfur and non-sulfur bacteria | n/a | pufB, Light-harvesting B875 beta chain | Rhodobacter sphaeroides | YP_353332 |
| Reducing power | NADPH | All photoautotrophic organisms | n/a | pgi, phosphoglucose isomerase | Synechococcus PCC 6301 | YP_172776 |
| Thermotolerance | transcriptional regulators | All photoautotrophic organisms | n/a | hrcA, heat-inducible transcription repressor | Synechocystis PCC 6803 | NP_440130 |

Figure 2 (Continued)

| Module | Target | Relevance | EC (if relevant) | Exemplary Gene Name | Organism | Locus/Accession |
|---|---|---|---|---|---|---|
| Thermotolerance | transcriptional regulators | cyanobacteria | n/a | hik34, histidine kinase 34 | Synechocystis PCC 6803 | slr1285 |
| Thermotolerance | lipid profiles of membranes | All photoautotrophic organisms | 1.14.19 | desA, delta-12-desaturase | Synechocystis PCC 6803 | NP_441489 |
| Thermotolerance | lipid profiles of membranes | All photoautotrophic organisms | n/a | desB, delta-15 desaturase | Synechocystis PCC 6803 | NP_441622 |
| Thermotolerance | lipid profiles of membranes | All photoautotrophic organisms | 1.14.19.1 | desC, stearoyl-CoA 9-desaturase | Synechocystis PCC 6803 | NP_442430 |
| Thermotolerance | lipid profiles of membranes | All photoautotrophic organisms | 1.14.19.3 | desD, delta-6-desaturase | Synechocystis PCC 6803 | NP_441824 |
| CO2 fixation | acetyl-CoA flux | All photoautotrophic organisms | 1.3.99.3 | acyl coenzyme A dehydrogenase | Synechococcus PCC 6301 | YP_171045 |
| CO2 fixation | acetyl-CoA flux | All photoautotrophic organisms | 1.1.1.94 | glycerol 3-phosphate dehydrogenase, NADP-dependent | Synechococcus PCC 7942 | YP_401539 |
| CO2 fixation | acetyl-CoA flux | All photoautotrophic organisms | 1.1.1.28 | lactate dehydrogenase, ldhA | Synechococcus PCC 6301 | YP_170916 |

Figure 2 (Continued)

>Q3M3Y1|epoxide hydrolase|EC 3.3.2.3|Anabaena variabilis
(strain ATCC 29413 / PCC 7937)|TrEMBL MFPSFLPAAVGQLTESESIALAKTIQTQAIATPLSNQPITTAYVRQGSGGTPILLIHGFD
SSVLEFRRLLPLLGKENETWAVDLLGFGFTQRLAGIKFSPVAIRTHLYSFWKTLINQPVI
LVGASMGGAAAIDFTLTYPEAVQKLVLIDSAGLRGGSPLSKFMFPPLDYLAAQFLRSPKV
RDRVSRAAYKNPNLATVDALCCGALHLEMPSWPEALIAFTKSGGYTAFRFKQLAEIISPT
LILWGDADRILGTEDGKRFKRAIPHSQLIWIQDCGHIPHLEQPGITAQHILSFCS (SEQ ID NO. 19)

FIG. 5

Table 3. Genes identified as putative oxygenases in the *A. marina* genome

| Locus tag | Location | Product |
|---|---|---|
| AM1_0031 | chromosome | pheophorbide A oxygenase |
| AM1_0459 | chromosome | oxidoreductase, 2-nitropropane dioxygenase family |
| AM1_0159 | chromosome | Rieske 2Fe-2S domain protein |
| AM1_0450 | chromosome | Rieske iron-sulfur (cyt b6f) fusion protein |
| AM1_0466 | chromosome | heme oxygenase |
| AM1_0519 | chromosome | phytanoyl-CoA dioxygenase (PhyH), putative |
| AM1_0571 | chromosome | glyoxalase/bleomycin resistance protein/dioxygenase |
| AM1_0661 | chromosome | lignostilbene-alpha,beta-dioxygenase, putative |
| AM1_0817 | chromosome | lipoxygenase |
| AM1_0850 | chromosome | heme oxygenase |
| AM1_0925 | chromosome | retinal pigment epithelial membrane protein, putative (member of COG3670 dioxygenase family) |
| AM1_0975 | chromosome | kynurenine 3-monooxygenase, putative |
| AM1_0983 | chromosome | phytanoyl-CoA dioxygenase (PhyH) superfamily, putative |
| AM1_1146 | chromosome | dioxygenase subfamily protein |
| AM1_1232 | chromosome | glyoxalase/bleomycin resistance protein/dioxygenase |
| AM1_1272 | chromosome | retinal pigment epithelial membrane protein, putative (member of COG3670 dioxygenase family) |
| AM1_1622 | chromosome | luciferase-like monooxygenase |
| AM1_1961 | chromosome | short putative Rieske iron sulfur protein |
| AM1_2001 | chromosome | antibiotic biosynthesis monooxygenase domain protein |
| AM1_2165 | chromosome | salicylate 1-monooxygenase, putative |
| AM1_2263 | chromosome | glyoxalase/bleomycin resistance protein/dioxygenase |
| AM1_2357 | chromosome | kynurenine 3-monooxygenase, putative |

FIG. 6

Table 3. Genes identified as putative oxygenases in the *A. marina* genome

| Locus tag | Location | Product |
|---|---|---|
| AM1_2424 | chromosome | 2OG-Fe(II) oxygenase, putative |
| AM1_2850 | chromosome | Rieske 2Fe-2S domain protein, ISS putative |
| AM1_2858 | chromosome | oxidoreductase, 2OG-Fe(II) oxygenase family, putative |
| AM1_2905 | chromosome | pheophorbide A oxygenase |
| AM1_2911 | chromosome | glyoxalase/bleomycin resistance protein/dioxygenase |
| AM1_2965 | chromosome | glyoxalase/bleomycin resistance protein/dioxygenase |
| AM1_3102 | chromosome | retinal pigment epithelial membrane protein, putative (member of COG3670 dioxygenase family) |
| AM1_3225 | chromosome | monooxygenase, flavin binding family |
| AM1_3286 | chromosome | conserved hypothetical protein, possible aromatic ring-cleaving dioxygenase-like protein |
| AM1_3288 | chromosome | glyoxalase/bleomycin resistance protein/dioxygenase |
| AM1_3306 | chromosome | monooxygenase, FAD-binding protein, putative |
| AM1_3564 | chromosome | lipoxygenase |
| AM1_3682 | chromosome | short putative Rieske iron sulfur protein |
| AM1_3707 | chromosome | oxidoreductase, 2OG-Fe(II) oxygenase family |
| AM1_3768 | chromosome | glyoxalase/bleomycin resistance protein/dioxygenase |
| AM1_3889 | chromosome | antibiotic biosynthesis monooxygenase family protein |
| AM1_3903 | chromosome | lipoxygenase |
| AM1_4154 | chromosome | oxidoreductase, 2OG-Fe(II) oxygenase family |
| AM1_4158 | chromosome | Predicted membrane protein fused with a Rieske [2Fe-2S] domain |
| AM1_4175 | chromosome | antibiotic biosynthesis monooxygenase, putative |
| AM1_4450 | chromosome | cytochrome b6f complex Rieske iron-sulfur subunit PetC |
| AM1_4518 | chromosome | oxidoreductase, 2OG-Fe(II) oxygenase family |

FIG. 6A

Table 3. Genes identified as putative oxygenases in the *A. marina* genome

| Locus tag | Location | Product |
|---|---|---|
| AM1_4550 | chromosome | 4-hydroxyphenylpyruvate dioxygenase |
| AM1_4675 | chromosome | glyoxalase/bleomycin resistance protein/dioxygenase |
| AM1_4788 | chromosome | glyoxalase/bleomycin resistance protein/dioxygenase, putative |
| AM1_4806 | chromosome | oxidoreductase, 2OG-Fe(II) oxygenase family |
| AM1_4978 | chromosome | Rieske, 2Fe-2S protein, putative |
| AM1_5032 | chromosome | glyoxalase/bleomycin resistance protein/dioxygenase |
| AM1_5320 | chromosome | Ferredoxin subunits of nitrite reductase and ring-hydroxylating dioxygenases, containing conserved Rieske (2Fe-2S) region |
| AM1_5665 | chromosome | possible chlorophyllide *a* oxygenase analog |
| AM1_6008 | chromosome | monooxygenase, FAD-binding |
| AM1_6344 | chromosome | cysteine dioxygenase type I family, putative |
| AM1_A0048 | pREB1 | Glyoxalase/bleomycin resistance/dioxygenase, EC 1.13.11.27 and 2.5.1.18 |
| AM1_A0067 | pREB1 | Phenylpropionate dioxygenase and related ring-hydroxylating dioxygenases, large terminal subunit |
| AM1_B0068 | pREB2 | glyoxalase/bleomycin resistance protein/dioxygenase, EC 1.13.11.39 and 1.13.11.27 |
| AM1_B0070 | pREB2 | glyoxalase/bleomycin resistance protein/dioxygenase |
| AM1_B0244 | pREB2 | dioxygenase, putative |
| AM1_C0108 | pREB3 | heme oxygenase |
| AM1_C0205 | pREB3 | heme oxygenase (decyclizing) |
| AM1_C0276 | pREB3 | antibiotic biosynthesis monooxygenase, putative |
| AM1_C0277 | pREB3 | antibiotic biosynthesis monooxygenase, putative |
| AM1_D0277 | pREB4 | glyoxalase/bleomycin resistance protein/dioxygenase, putative, EC 1.13.11.39 and 1.13.11.27 |
| AM1_F0119 | pREB6 | glyoxalase/bleomycin resistance protein/dioxygenase, EC 2.5.1.18 |
| AM1_G0157 | pREB7 | glyoxalase/bleomycin resistance protein/dioxygenase, EC 1.13.11.39 and 1.13.11.27 |

FIG. 6B

Table 4. Genes identified as putative epoxide reductases in the *A. marina* genome

| Locus tag | Expect | Location | Product |
| --- | --- | --- | --- |
| AM1_2935 | | chromosome | Possible thioredoxin reductase, vitamin k epoxide reductase protein |
| AM1_5243 | 3.00E-93 | chromosome | alpha/beta hydrolase fold |
| AM1_2117 | 8.00E-21 | chromosome | alpha/beta hydrolase fold |
| AM1_3177 | 9.00E-21 | chromosome | hydrolase, alpha/beta fold family protein, putative |
| AM1_3250 | 4.00E-17 | chromosome | hydrolase, alpha/beta fold family protein |
| AM1_2791 | 6.00E-13 | chromosome | alpha/beta hydrolase fold |
| AM1_2887 | 4.00E-12 | chromosome | alpha/beta hydrolase fold |
| AM1_1180 | 5.00E-12 | chromosome | hydrolase, alpha/beta fold family |
| AM1_5371 | 2.00E-10 | chromosome | alpha/beta hydrolase fold |
| AM1_3451 | 6.00E-08 | chromosome | alpha/beta hydrolase fold |
| AM1_5472 | 1.00E-07 | chromosome | hydrolase, alpha/beta fold family |
| AM1_5195 | 6.00E-07 | chromosome | alpha/beta hydrolase fold |
| AM1_E0219 | 5.00E-06 | pREB5 | carboxylesterase NP, putative |
| AM1_E0084 | 6.00E-06 | pREB5 | hydrolase, alpha/beta fold family |
| AM1_B0059 | 2.00E-05 | pREB2 | alpha/beta hydrolase |
| AM1_5958 | 0.001 | chromosome | lysophospholipase |
| AM1_6117 | 0.15 | chromosome | hydrolase, alpha/beta fold family |
| AM1_2640 | 0.32 | chromosome | conserved hypothetical protein |

FIG. 7

Table 5. Genes identified as putative SAM-utilizing oxygenases in the *A. marina* genome

| Locus tag | Location | Product |
|---|---|---|
| AM1_0849 | chromosome | S-adenosyl-methyltransferase MraW, putative |
| AM1_1692 | chromosome | radical SAM domain/ B12 binding domain protein |
| AM1_1842 | chromosome | precorrin-2 C20-methyltransferase |
| AM1_2229 | chromosome | radical SAM domain protein |
| AM1_2342 | chromosome | radical SAM domain protein |
| AM1_2373 | chromosome | radical SAM domain protein |
| AM1_3674 | chromosome | magnesium protoporphyrin O-methyltransferase |
| AM1_3982 | chromosome | radical SAM enzyme, Cfr family |
| AM1_5023 | chromosome | radical SAM domain protein |
| AM1_5798 | chromosome | radical SAM domain protein |
| AM1_A0041 | pREB1 | SAM-dependent methyltransferase, putative |

FIG. 8

Table 6. Genes identified as photosystem proteins in the *A. marina* genome

| Locus tag | Location | Product |
|---|---|---|
| AM1_2457 | chromosome | photosystem I core protein PsaA |
| AM1_2458 | chromosome | photosystem I core protein PsaB |
| AM1_2166 | chromosome | photosystem II D1 protein PsbA |
| AM1_1083 | chromosome | photosystem II D2 protein PsbD |
| AM1_2026 | chromosome | photosystem II CP47 protein PsbB |
| AM1_1084 | chromosome | photosystem II CP43 protein PsbC |

FIG. 9

HYPERPHOTOSYNTHETIC ORGANISMS

CROSS REFERENCE TO RELATED APPLICATIONS

This application claims priority from U.S. Provisional Applications 60/987,046, filed on Nov. 10, 2007; 61/032,169 filed on Feb. 28, 2008; and 61/090,933, filed on Aug. 22, 2008, the disclosure of each of which is incorporated by reference herein for all purposes.

SEQUENCE LISTING

The instant application contains a Sequence Listing which has been submitted via EFS-Web and is hereby incorporated by reference in its entirety. Said ASCII copy, created on Dec. 23, 2009, is named 14953US.txt, and is 26,428 bytes in size.

FIELD

The present invention relates to the field of synthetic biology, and more particularly to industrialized photoautotrophic organisms designed to efficiently convert carbon dioxide and light into biomass and carbon-based products of interest.

BACKGROUND

Photosynthesis is a process by which biological entities utilize sunlight and $CO_2$ to produce sugars for energy. Existing photoautotrophic organisms (i.e., plants, algae, and photosynthetic bacteria) are poorly suited for industrial bioprocessing. In particular, most organisms have slow doubling times (10-72 hrs) compared to industrialized heterotrophic organisms such as *Escherichia coli* (20 minutes). Additionally, photoautotrophic organisms are often susceptible to moderate variations in common environmental stresses including pH, temperature and salt tolerance. Such susceptibilities make industrial applications of photoautotrophs inefficient. Moreover, increasingly toxic environmental factors (for example, toxic pollutants including heavy metals, nitrogen and sulfer based industrial by-products) can further limit applications of photoautotrophs to particular industrial uses.

Desirable products which can potentially be produced in microorganisms (for example ethanol and other branched chain higher alcohols produced in engineered *E. coli* (Atsumi, et al. Nature (2008) vol 451:86-90)) have been found difficult to process in photoautotrophs because of incompatible or inefficient metabolic pathways of production or the complete absence of necessary cell based biocatalysts.

Thus, there is need in the art for improved photoautotrophic organisms that are better suited for industrial bioprocessing.

SUMMARY

The present invention provides methods and compositions for engineering pathways that stably utilize photosynthetic organisms by, e.g., genetically improving their light capture and carbon fixation efficiencies and by optimizing their growth properties for propagation in photobioreactors. The present invention also provides the resulting engineered "HyperPhotosynthetic" cells and organisms that enable efficient conversion of carbon dioxide and light into carbon-based products of interest.

Provided herein is an engineered photosynthetic cell comprising: at least one engineered nucleic acid selected from the group consisting of a light capture nucleic acid, a carbon dioxide fixation pathway nucleic acid, an NADH pathway nucleic acid, an NADPH pathway nucleic acid, a thermotolerance nucleic acid, a pH tolerance nucleic acid, a flue gas tolerance nucleic acid, a salt tolerance nucleic acid, a nutrient independence nucleic acid and a near infrared absorbance nucleic acid wherein said engineered cell expresses a heterologous protein encoded by said engineered nucleic acid, overexpresses an endogenous protein as a result of the presence of said engineered nucleic acid, downregulates an endogenous protein as a result of the presence of said engineered nucleic acid, or has a gene knocked-out as a result of the presence of said engineered nucleic acid.

Also provided herein is an engineered cell comprising a plurality of engineered light capture nucleic acids, carbon dioxide fixation pathway nucleic acids, NADH pathway nucleic acids, NADPH pathway nucleic acids, thermotolerance nucleic acids, pH tolerance nucleic acids, flue gas tolerance nucleic acids, salt tolerance nucleic acids, nutrient independence nucleic acids and near infrared absorbance nucleic acids.

The invention also provides an engineered photosynthetic cell comprising an engineered carbon fixation pathway nucleic acid encoding one or more proteins selected from the group consisting of 3-hydroxypropionate cycle protein, Calvin cycle protein, carbon-acetyl-CoA flux protein, gluconeogenesis pathway protein, glyoxylate shunt pathway protein, pyruvate synthesis pathway protein, reductive TCA cycle protein and Woods-Ljungdahl pathway protein.

The invention also provides an engineered photosynthetic cell comprising an engineered NADH pathway nucleic acid encoding one or more proteins selected from the group consisting of $NAD^+$-dependent isocitrate dehydrogenase-idh1 protein; $NAD^+$-dependent isocitrate dehydrogenase-idh2 protein; malate dehydrogenase protein; soluble pyridine nucleotide transhydrogenase (sthA or udhA) protein; membrane-bound pyridine nucleotide transhydrogenase, subunit alpha, pntA protein; membrane-bound pyridine nucleotide transhydrogenase, subunit beta, pntB protein; and NADH: ubiquinone oxidoreductase (nuo) operon protein.

The invention also provides an engineered photosynthetic cell comprising an engineered NADPH pathway nucleic acid encoding one or more proteins selected from the group consisting of a glucose-6-phosphate dehydrogenase; zwf protein; 6-phosphogluconolactonase-pgl protein; 6-phosphogluconate dehydrogenase, gnd protein; NADP-dependent isocitrate dehydrogenase protein; NADP-dependent malic enzyme; soluble pyridine nucleotide transhydrogenase (sthA or udhA) protein; membrane-bound pyridine nucleotide transhydrogenase, subunit alpha, pntA protein; and membrane-bound pyridine nucleotide transhydrogenase, subunit beta, pntB protein.

The invention also provides an engineered photosynthetic cell comprising an engineered thermotolerance nucleic acid encoding one or more proteins selected from the group consisting of betaine biosynthesis protein; photosystem stability and repair protein; and protein folding protein.

The invention also provides an engineered photosynthetic cell comprising an engineered pH tolerance nucleic acid encoding one or more proteins selected from the group consisting of glutamate decarboxylase A (GadA) protein; glutamate decarboxylase beta (GadB) protein; glutamate: gamma-aminobutyric acid antiporter (GadC) protein; biodegradative arginine decarboxylase (AdiA) protein; arginine: agmatin antiporter (AdiC) protein; chaperone protein dnaK2 (DnaK) protein; DNA-directed RNA polymerase, sigma subunit (sll0306) protein; Zn-dependent protease (sll0528) protein; metal-dependent phosphoesterase (sll0549) protein; acid-stress related membrane protein (sll0939) protein; heat shock molecular chaperone (sll1514) protein; mannose-1-phosphate guanyltransferase (sll1558) protein; RNA polymerase sigma factor (sll2012) protein; carboxyl-terminal processing protease (slr0008) protein; molecular chaperone (slr0093) protein; geranylgeranyl pyrophosphate synthase (slr0611) protein; CheY-like receiver (slr1214) protein; signal transduction histidine kinase (slr1285) protein; superoxide dismutase (slr1516) protein; hydrogenase expression/formation protein (slr1675) protein; esterase (slr1916) protein; hydrogenase component protein (ssl3044) protein; chloride channel protein; and acid-stress tolerance protein.

In addition, the invention further provides an engineered photosynthetic cell comprising an engineered flue gas tolerance nucleic acid encoding one or more proteins selected from the group consisting of $NO_x$ tolerance protein, $SO_x$ tolerance protein, mercury tolerance protein, metal tolerance protein and particulate aerosol tolerance protein.

In yet another embodiment, the invention provides an engineered photosynthetic cell comprising an engineered salt tolerance nucleic acid encoding one or more proteins selected from the group comprising $Na^+/H^+$ antiporter protein (apnhaP), catalase protein (katG), salt and cadmium stress related protein (CW80Cd404), breast basic conserved protein (bbc1) and betaine biosynthesis protein.

In still another embodiment, the invention provides an engineered photosynthetic cell comprising an engineered near infrared absorbance nucleic acid, wherein the nucleic acid comprises a chlorophyll d biosynthetic nucleic acid.

In still another embodiment, the invention provides an engineered photosynthetic cell comprising an engineered nutrient independence nucleic acid encoding one or more a proteins selected from the group consisting of an ammonia assimilation protein, a nitrate/nitrite assimilation protein, a nitrate/nitrite assimilation-nitrite tolerance protein, a nitrogen fixation protein, an urea assimilation protein, a Vitamin $B_{12}$ biosynthesis protein, a Vitamin $B_{12}$ biosynthesis-$Co^{2+}$ transport protein and a Vitamin $B_{12}$ independence protein. In certain related embodiments, the Vitamin $B_{12}$ biosynthesis protein comprises one or more proteins selected from the group consisting of uroporphyrin-III C-methyltransferase cobaltochelatase (cysG) protein; sirohydrochlorin cobaltochelatase (cbiK) protein; precorrin-2 C20-methyltransferase (cbiL) protein; precorrin-3B methylase (cbiH) protein; bifunctional CbiG/precorrin methyltransferase (cbiG) protein; precorrin-4 C11-methyltransferase (cbiF) protein; cobalamin biosynthesis protein (cbiD); NADPH-dependent precorrin-6A reductase (cbiJ) protein; precorrin-6B C5,15-methyltransferase (cbiE) protein; precorrin-6B C12 decarboxylase (cbiT) protein; precorrin-8X-methylmutase (cbiC) protein; cobyrinic acid A,C-diamide synthase (cbiA) protein; cob(I)yrinic acid a,c-diamide adenosyltransferase (btuR) protein; cobyrinic acid synthase (cbiP) protein; cobyric acid decarboxylase (cobD) protein; adenosylcobinamide-phosphate synthase (cbiB) protein; alpha ribazole-5'-P phosphatase (cobC) protein; cobalamin (5'-phosphate) synthase (cobS) protein; cobinamide phosphate guanylyl transferase (cobU) protein; and nicotinate-nucleotide dimethylbenzimidazole-P phosphoribosyl transferase (cobT) protein. In yet another related embodiment, the Vitamin $B_{12}$ biosynthesis-$Co^{2+}$ transport protein comprises one or more proteins selected from the group consisting of ABC-type $Co^{2+}$ transport system, permease component protein; ABC-type cobalt transport system, periplasmic component protein; and ABC-type cobalt transport system, permease component protein. In other related embodiments, the Vitamin $B_{12}$ independence protein comprises one or more proteins selected from the group consisting of 5-methyltetrahydropteroyltriglutamate-homocysteine methyltransferase (metE) protein; ribonucleoside-diphosphate reductase, alpha subunit (nrdA) protein; and ribonucleoside-diphosphate reductase, beta subunit (nrdB) protein. In a related embodiment, the metE protein is from *Escherichia coli* K12 (accession number NP_418273.1 (SEQ ID NO: 20)) or *Thermosynechococcus elongatus* BP-1 (accession number NP_681881 (SEQ ID NO: 21)).

In various embodiments of the invention, the engineered nucleic acid encodes a heterologous protein that is expressed by the engineered cell, causes overexpression of an endogenous protein within the engineered cell, causes downregulation of an endogenous protein in the engineered cell, or causes a gene knock-out in the engineered cell.

In another embodiment of the invention, the engineered cell is used to produce biomass, carbon-based products of interest or pharmaceutical agents.

In yet other embodiments, the invention provides an engineered carbon-fixing cell comprising at least one engineered nucleic acid selected from the group consisting of thermotolerance nucleic acid, pH tolerance nucleic acid, flue gas tolerance nucleic acid, salt tolerance nucleic acid, nutrient independence nucleic acid and near infrared absorbance nucleic acid, wherein said engineered cell expresses heterologous protein encoded by said engineered nucleic acid, overexpresses endogenous protein as a result of the presence of said engineered nucleic acid, downregulates endogenous protein as a result of the presence of said engineered nucleic acid, or has a gene knocked-out as a result of the presence of said engineered nucleic acid is provided.

In certain embodiments of the invention, the engineered cell is an autotrophic cell. In certain other embodiments, the engineered cell is a photoautotrophic cell. In various embodiments of the invention, the engineered cell is selected from a group consisting of plant, prokaryote, eukaryote, yeast, filamentous fungi, protozoa, algae and synthetic cells.

Also disclosed is a method to produce carbon-based products of interest, comprising the steps of: a) engineering a cell to express at least one engineered nucleic acid selected from the group consisting of light capture nucleic acid, carbon dioxide fixation pathway nucleic acid, NADH pathway nucleic acid, NADPH pathway nucleic acid, thermotolerance nucleic acid, pH tolerance nucleic acid, flue gas tolerance nucleic acid, salt tolerance nucleic acid, nutrient independence nucleic acid and near infrared absorbance nucleic acid; b) said cell expressing a heterologous protein encoded by said engineered nucleic acid, overexpressing endogenous protein as a result of the presence of said engineered nucleic acid, downregulating endogenous protein as a result of the presence of said engineered nucleic acid, or having a gene knocked-out as a result of the presence of said engineered nucleic acid; and c) culturing said cell in the presence of $CO_2$ and light to produce the carbon-based products of interest.

FIGURES

FIG. 1 provides Table 1 which identifies genes that can be expressed or upregulated in association with the engineering of various modules of the invention.

FIG. 2 provides Table 2 which identifies genes that can be downregulated or knocked out in association with the engineering of various modules of the invention.

FIG. 3 depicts viability of wild-type and genetically engineered *Synechococcus* sp. PCC 7002 on A+ media agarose plates without B12.

Figure 4:
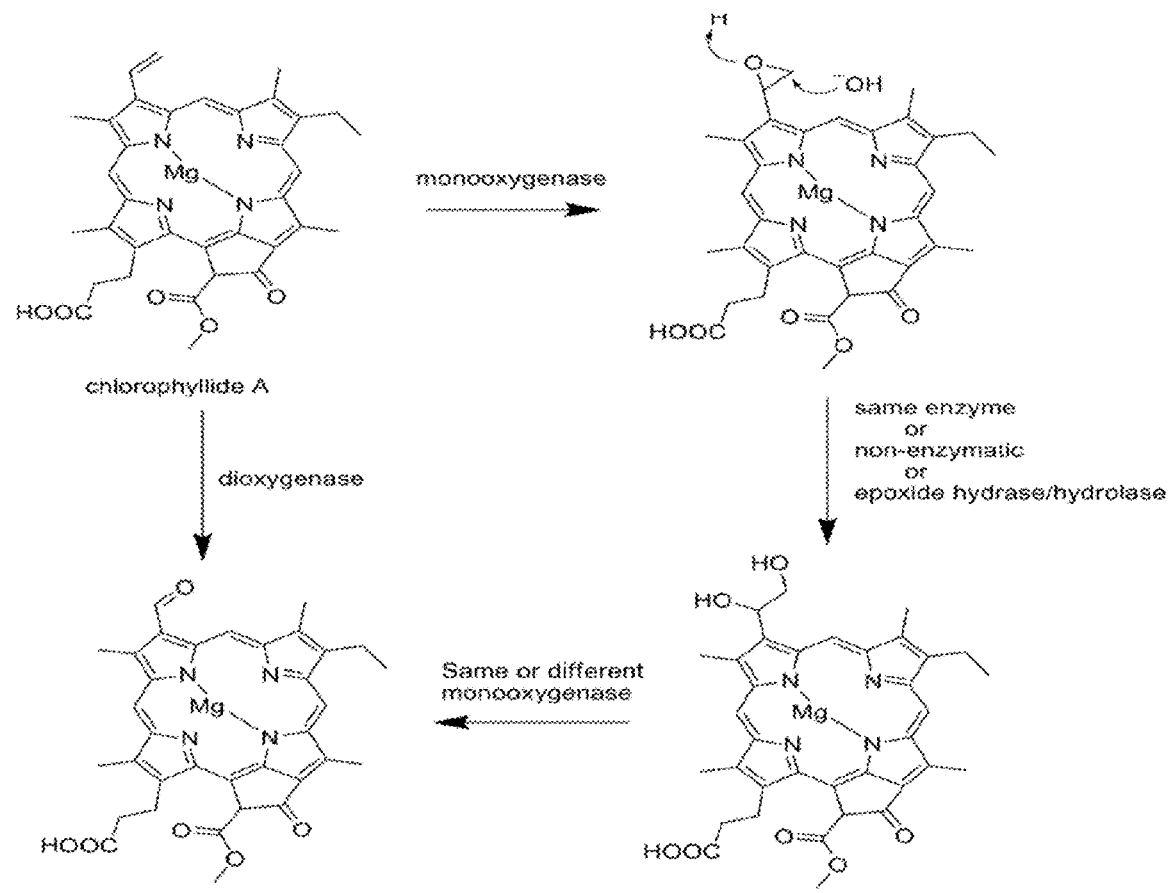

FIG. 4 provides synthetic schemes for chlorophyll d (Chl d) derivation from chlorophyll a (Chl a) with Chlorophyllide, a precursor of Chl, shown here for simplicity.

FIG. 5 provides a query sequence (SEQ ID NO: 19) for an epoxide hydrolase search.

FIG. 6 provides Table 3 which lists genes identified as those encoding oxygenases in the *A. marina* genome.

FIG. 7 provides Table 4 which lists genes identified as those encoding epoxide reductases in the *A. marina* genome.

FIG. 8 provides Table 5 which lists genes identified as those encoding SAM-utilizing oxygenases in the *A. marina* genome.

FIG. 9 provides Table 6 which lists genes identified as those encoding photosystem proteins in the *A. marina* genome.

FIG. 10A is a photograph of an agarose gel showing PCR confirmation of transgenic *Synechococcus* sp. PCC7002 strains: JCC1-UdhA (lanes 2 and 3); JCC1-ZWF (lane 4); and JCC1-SAR86 (lane 5). FIG. 10B is a photograph of an agarose gel showing PCR products from JCC136.

Figure 11:
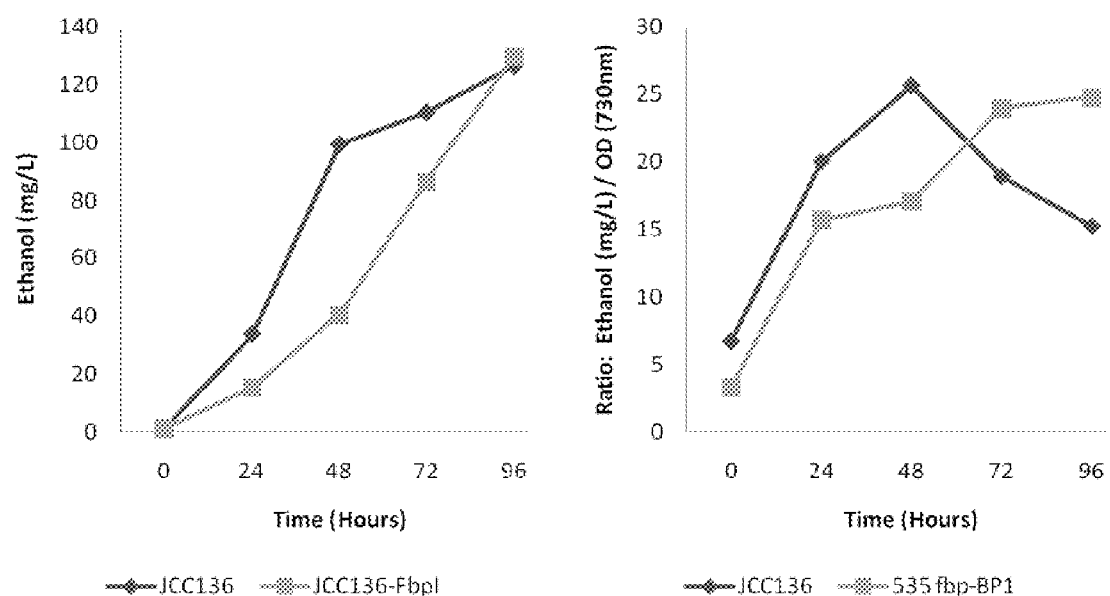

FIG. 11 depicts a graph of ethanol production (left) and ethanol to OD ratio (right) as a function of time in *Synechococcus* sp. PCC7002 strains JCC136 and JCC136-FbpI.

SEQUENCE LISTING

The amino acid sequences listed in the accompanying sequence listing are shown using standard letter abbreviations for amino acid residues, as defined in 37 C.F.R. 1.822. In the accompanying amino acid sequence listing:

Abbreviations and Terms

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a cell" includes one or a plurality of such cells, and reference to "comprising a thioesterase" includes reference to one or more thioesterase peptides and equivalents thereof known to those of ordinary skill in the art, and so forth. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Accession Numbers: The accession numbers throughout this description correspond to those found in the following databases: NCBI (National Center for Biotechnology Information), TIGR (The Institute for Genomic Research), and KEGG (Kyoto Encyclopedia of Genes and Genomes). The accession numbers are as provided in the databases on Nov. 10, 2007.

Enzyme Classification Numbers (EC): The EC numbers provided throughout this description are derived from the KEGG Ligand database, maintained by the Kyoto Encyclopedia of Genes and Genomics, sponsored in part by the University of Tokyo. The EC numbers are as provided in the database on Nov. 10, 2007.

DNA: Deoxyribonucleic acid. DNA is a long chain polymer which includes the genetic material of most living organisms (some viruses have genes including ribonucleic acid, RNA). The repeating units in DNA polymers are four different nucleotides, each of which includes one of the four bases, adenine, guanine, cytosine and thymine bound to a deoxyribose sugar to which a phosphate group is attached.

Codon: Triplets of nucleotides, referred to as codons, in DNA molecules code for amino acids in a peptide. The term codon is also used for the corresponding (and complementary) sequences of three nucleotides in the mRNA into which the DNA sequence is transcribed.

Endogenous: As used herein with reference to a nucleic acid molecule and a particular cell or microorganism refers to a nucleic acid sequence or peptide that is in the cell and was not introduced into the cell using recombinant engineering techniques. For example, a gene that was present in the cell when the cell was originally isolated from nature is considered to be endogenous. A gene is still considered endogenous if the control sequences, such as a promoter or enhancer sequences that activate transcription or translation have been altered through recombinant techniques.

Exogenous: As used herein with reference to a nucleic acid molecule and a particular cell or microorganism refers to a nucleic acid sequence or peptide that was not present in the cell when the cell was originally isolated from nature. For example, a nucleic acid that originated in a different microorganism and was engineered into an alternate cell using recombinant DNA techniques or other methods for delivering said nucleic acid is considered to be exogenous.

Expression: The process by which a gene's coded information is converted into the molecules that support the structures and functions of a cell, such as a protein, transfer RNA, or ribosomal RNA. Expressed genes include those that are transcribed into mRNA and then translated into protein and those that are transcribed into RNA but not translated into protein (for example, transfer and ribosomal RNAs).

Overexpression: Overexpression refers to any state in which a gene is caused to be transcribed at an elevated rate as compared to the endogenous transcription rate for that gene. In some examples, overexpression additionally includes an elevated rate of translation of the gene compared to the endogenous translation rate for that gene. Methods of testing for overexpression are well known in the art, for example transcribed RNA levels can be assessed using reverse transcriptase polymerase chain reaction (RT-PCR) and protein levels can be assessed using sodium dodecyl sulfate polyacrylamide gel electrophoresis (SDS-PAGE) analysis. Furthermore, a gene is considered to be overexpressed when it exhibits elevated activity compared to its endogenous activity, which may occur, for example, through reduction in concentration or activity of its inhibitor, or via expression of mutant version with elevated activity. In preferred embodiments, when the host cell encodes an endogenous gene with a desired biochemical activity, it is useful to overexpress an exogenous gene, which allows for more explicit regulatory control in the bioprocessing and a means to potentially mitigate the effects of central metabolism regulation, which is focused around the native genes explicitly.

Downregulation: Downregulation refers to any state in which a gene is caused to be transcribed at a reduced rate compared to the endogenous gene transcription rate for that gene. In certain embodiments, gene expression is downregulated via expression of nucleic acids, such as antisense oligonucleotides, double-stranded RNA, small interfering RNA, small hairpin RNA, microRNAs, ribozymes, and the like. In some examples, downregulation additionally includes a reduced level of translation of the gene compared to the endogenous translation rate for that gene. Furthermore, a gene is considered to be downregulated when it exhibits decreased activity compared to its endogenous activity, which may occur, for example, through an increase in concentration or activity of its inhibitor, or via expression of mutant version with reduced activity. Methods of testing for downregulation are well known to those in the art, for example the transcribed RNA levels can be assessed using RT-PCR and proteins levels can be assessed using SDS-PAGE analysis.

Knock-out: A gene whose level of expression or activity has been reduced to zero. In some examples, a gene is knocked-out via deletion or replacement of some or all of its coding sequence. In other examples, a gene is knocked-out via introduction or removal of one or more nucleotides into its open-reading frame, which results in translation of a nonsense or otherwise non-functional protein product.

Autotroph: Autotrophs (or autotrophic organisms) are organisms that produce complex organic compounds from simple inorganic molecules and an external source of energy, such as light (photoautotroph) or chemical reactions of inorganic compounds.

Heterotroph: Heterotrophs (or heterotrophic organisms) are organisms that, unlike autotrophs, cannot derive energy directly from light or from inorganic chemicals, and so must feed on organic carbon substrates. They obtain chemical energy by breaking down the organic molecules they consume. Heterotrophs include animals, fungi, and numerous types of bacteria.

Hyperphotosynthetic: a cell or organism expressing photosynthetic proteins that through recombinant DNA techniques has been specifically engineered to express endogenous and/or exogenous nucleic acids that result in one or more functional improvements related to industrial bioprocessing and the conversion of carbon dioxide and light into reduced carbon products or cell mass. A Hyperphotosynthetic cell also encompasses a cell or organism engineered as described above that has been evolved or mutagenized to achieve one or more functional improvements.

Hydrocarbon: generally refers to a chemical compound that consists of the elements carbon (C), optionally oxygen (O), and hydrogen (H).

Biosynthetic pathway: Also referred to as "metabolic pathway," refers to a set of anabolic or catabolic biochemical reactions for converting (transmuting) one chemical species into another. For example, a hydrocarbon biosynthetic pathway refers to the set of biochemical reactions that convert inputs and/or metabolites to hydrocarbon product-like intermediates and then to hydrocarbons or hydrocarbon products. Anabolic pathways involve constructing a larger molecule from smaller molecules, a process requiring energy. Catabolic pathways involve breaking down of larger: molecules, often releasing energy.

Cellulose: Cellulose $[(C_6H_{10}O_5)_n]$ is a long-chain polymer polysaccharide carbohydrate, of beta-glucose. It forms the primary structural component of plants and is not digestible by humans. Cellulose is a common material in plant cell walls and was first noted as such in 1838. It occurs naturally in almost pure form only in cotton fiber; in combination with lignin and any hemicellulose, it is found in all plant material.

Surfactants: Surfactants are substances capable of reducing the surface tension of a liquid in which they are dissolved. They are typically composed of a water-soluble head and a hydrocarbon chain or tail. The water soluble group is hydrophilic and can be either ionic or nonionic, and the hydrocarbon chain is hydrophobic.

Biofuel: A biofuel is any fuel that derives from a biological source.

Engineered nucleic acid: An "engineered nucleic acid" is a nucleic acid molecule that includes at least one difference from a naturally-occurring nucleic acid molecule. An engineered nucleic acid includes all exogenous modified and unmodified heterologous sequences (i.e., sequences derived from an organism or cell other than that harboring the engineered nucleic acid) as well as endogenous genes, operons, coding sequences, or non-coding sequences, that have been modified, mutated, or that include deletions or insertions as compared to a naturally-occurring sequence. Engineered nucleic acids also include all sequences, regardless of origin, that are linked to an inducible promoter or to another control sequence with which they are not naturally associated. Engineered nucleic acids further include all sequences that can be used to down-regulate or knock out expression of an endogenous gene. These include anti-sense molecules, RNAi molecules, constructs for producing homologous recombination, cre-lox constructs, and the like.

Light capture nucleic acid: A "light capture nucleic acid" refers to a nucleic acid that alone or in combination with another nucleic acid encodes one or more proteins that convert light energy (i.e., photons) into chemical energy such as a proton gradient, reducing power, or a molecule containing at least one high-energy phosphate bond such as ATP or GTP. Exemplary light capture nucleic acids include those encoding light-activated proton pumps such as rhodopsin, xanthorhodopsin, proteorhodopsin and bacteriorhodopsin, as well as nucleic acids encoding proteins that directly (light harvesting complexes, LHC I and LHC II) or indirectly (truncated light harvesting antenna, tla1) modulate light harvesting capture efficiencies. A light capture nucleic acids further includes a nucleic acid used to reduce the expression of or knock out one or more endogenous genes whose expression reduces light capture.

Carbon dioxide fixation pathway nucleic acid: A "carbon dioxide fixation pathway nucleic acid" refers to a nucleic acid that alone or in combination with another nucleic acid encodes a protein that enables autotrophic carbon fixation. A carbon dioxide fixation pathway nucleic acid also includes nucleic acids that direct carbon flux to key cellular intermediates required for efficient growth or carbon-based product formation, such as acetyl-CoA. Exemplary carbon dioxide fixation pathway nucleic acids includes those encoding propionyl-CoA carboxylase, pyruvate synthase, formate dehydrogenase, and ribulose-1,5-bisphosphate carboxylase/oxygenase (RuBisCO). A carbon dioxide fixation pathway nucleic acids further includes a nucleic acid used to reduce the expression of or knock out one or more endogenous genes whose expression reduces carbon dioxide fixation.

NADH pathway nucleic acid: A "NADH pathway nucleic acid" refers to a nucleic acid that alone or in combination with another nucleic acid encodes a protein to maintain an appropriately balanced supply of reduced NAD for carrying out carbon fixation. Exemplary NADH pathway nucleic acids include those encoding an $NAD^+$-dependent isocitrate dehydrogenase and malate dehydrogenase. A NADH pathway nucleic acid further includes a nucleic acid used to reduce the expression of or knock out one or more endogenous genes whose expression detracts from maintaining an appropriately balanced supply of reduced NAD for carrying out carbon fixation and other necessary biological processes.

NADPH pathway nucleic acid: A "NADPH pathway nucleic acid" refers to a nucleic acid that alone or in combination with another nucleic acid encodes a protein to maintain an appropriately balanced supply of reduced NADPH for carrying out carbon fixation. Exemplary NADPH pathway nucleic acids include those encoding phosphogluconolactonase and soluble pyridine nucleotide transhydrogenase. A NADPH pathway nucleic acid further includes a nucleic acid used to reduce the expression of or knock out one or more endogenous genes whose expression detracts from maintaining an appropriately balanced supply of reduced NADP for carrying out carbon fixation and other necessary biological processes.

Thermotolerance nucleic acid: A "thermotolerance nucleic acid" refers to a nucleic acid that alone or in combination with another nucleic acid encodes a protein whose overexpression, downregulation, or inhibition results in an increase in thermotolerance. Exemplary thermotolerance nucleic acids include those encoding ClpC/Hsp100, groESL1, HspA, and PsbU. A thermotolerance nucleic acid further includes a nucleic acid used to reduce the expression of or knock out one or more endogenous genes whose expression impairs thermotolerance pH tolerance nucleic acid: A "pH tolerance nucleic acid" refers to a nucleic acid that alone or in combination with another nucleic acid encodes a protein whose overexpression, downregulation, or inhibition enables growth at an elevated or reduced pH. Exemplary pH tolerance nucleic acids include those encoding glutamate decarboxylase and superoxide dismutase. A pH tolerance nucleic acid further includes a nucleic acid used to reduce the expression of or knock out one or more endogenous genes whose expression impairs pH tolerance.

Flue gas tolerance: A "Flue gas tolerance nucleic acid" refers to a nucleic acid that alone or in combination with another nucleic acid encodes a protein whose overexpression, downregulation, or inhibition enables growth in the presence flue gas components including carbon dioxide, $SO_x$, $NO_x$, and $N_2$. Exemplary flue gas tolerance nucleic acids include those encoding superoxide dismutase, catalase, cysteine synthase, and NirK. A flue gas tolerance nucleic acid further includes a nucleic acid used to reduce the expression of or knock out one or more endogenous genes whose expression impairs flue gas tolerance.

Nutrient independence nucleic acid: A "nutrient independence nucleic acid" refers to a nucleic acid that alone or in combination with another nucleic acid encodes a protein whose overexpression, downregulation, or inhibition enables propagation in the absence of, or under reduced concentrations of, an exogenous nutrient. Exemplary nutrient independence nucleic acids include those encoding MetE and NrdB. A nutrient independence gene further includes a nucleic acid used to reduce the expression of or knock out one or more endogenous genes whose expression impairs propagation in the absence of, or under reduced concentrations of, an exogenous nutrient.

Salt-tolerance nucleic acid: A "salt tolerance nucleic acid" refers to a nucleic acid that alone or in combination with another nucleic acid encodes a protein whose overexpression, downregulation, or inhibition enables propagation under conditions of elevated salinity, such as sea water Exemplary salt tolerance nucleic acids include those encoding Na+/H+ antiporter, and breast basic conserved.

Acetyl-CoA flux nucleic acid: An "acetyl-CoA flux nucleic acid" refers to a nucleic acid that alone or in combination with another nucleic acid encodes a protein whose overexpression, downregulation, or inhibition results in an increase in acetyl-CoA produced over a unit of time. Example nucleic acids that may be overexpressed include pantothenate kinase and pyruvate dehydrogenase. Nucleic acids that may be downregulated, inhibited, or knocked-out include acyl coenzyme A dehydrogenase, biosynthetic glycerol 3-phosphate dehydrogenase, and lactate dehydrogenase.

Chlorophyll d nucleic acid: A "chlorophyll d nucleic acid" refers to a nucleic acid that alone or in combination with another nucleic acid encodes a protein whose overexpression, downregulation, or inhibition results in the biosynthesis of chlorophyll d and its incorporation in reaction centers, photosystem (PS)I and PSII. A chlorophyll d nucleic acid enables propagation under, e.g., conditions in which the photosynthetically available radiation is likely completely used by organisms that absorb light using chlorophyll a and/or chlorophyll b such that the environment has low visible light intensity but high near infrared intensity where no other photosynthetic organisms absorb strongly so that an organism that uses chlorophyll d for light capture can thrive. Alternatively, a chlorophyll d nucleic acid enables propagation under conditions in which the wavelength of artificial light used for illumination is selected to allow propagation of an organism that uses chlorophyll d for light capture.

Sequence identity: The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

Comparison window: A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr. Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

DETAILED DESCRIPTION OF THE INVENTION

Organisms

The instant invention enables conversion of a photoautotrophic organism into a Hyperphotosynthetic organism. Photoautotrophic organisms include eukaryotic plants and algae, as well as prokaryotic cyanobacteria, green-sulfur bacteria, green non-sulfur bacteria, purple sulfur bacteria, and purple non-sulfur bacteria.

Plants include but are not limited to the following genera: *Arabidopsis, Beta, Glycine, Jatropha, Miscanthus, Panicum, Phalaris, Populus, Saccharum, Salix Simmondsia,* and *Zea.*

Algae and cyanobacteria include but are not limited to the following genera: *Acanthoceras, Acanthococcus, Acaryochloris, Achnanthes, Achnanthidium, Actinastrum, Actinochloris, Actinocyclus, Actinotaenium, Amphichrysis, Amphidinium, Amphikrikos, Amphipleura, Amphiprora, Amphithrix, Amphora, Anabaena, Anabaenopsis, Aneumastus, Ankistrodesmus, Ankyra, Anomoeoneis, Apatococcus, Aphanizomenon, Aphanocapsa, Aphanochaete, Aphanothece, Apiocystis, Apistonema, Arthrodesmus, Artherospira, Ascochloris, Asterionella, Asterococcus, Audouinella, Aulacoseira, Bacillaria, Balbiania, Bambusina, Bangia, Basichlamys, Batrachospermum, Binuclearia, Bitrichia, Blidingia, Botrdiopsis, Botrydium, Botryococcus, Botryosphaerella, Brachiomonas, Brachysira, Brachytrichia, Brebissonia, Bulbochaete, Bumilleria, Bumilleriopsis, Caloneis, Calothrix, Campylodiscus, Capsosiphon, Carteria, Catena, Cavinula, Centritractus, Centronella, Ceratium, Chaetoceros, Chaetochloris, Chaetomorpha, Chaetonella, Chaetonema, Chaetopeltis, Chaetophora, Chaetosphaeridium, Chamaesiphon, Chara, Characiochloris, Characiopsis, Characium, Charales, Chilomonas, Chlainomonas, Chlamydoblepharis, Chlamydocapsa, Chlamydomonas, Chlamydomonopsis, Chlamydomyxa, Chlamydonephris, Chlorangiella, Chlorangiopsis, Chlorella, Chlorobotrys, Chlorobrachis, Chlorochytrium, Chlorococcum, Chlorogloea, Chlorogonium, Chlorolobion, Chloromonas, Chlorophysema, Chlorophyta, Chlorosaccus, Chlorosarcina, Choricystis, Chromophyton, Chromulina, Chroococcidiopsis, Chroococcus, Chroodactylon, Chroomonas, Chroothece, Chrysamoeba, Chrysapsis, Chrysidiastrum, Chrysocapsa, Chrysocapsella, Chrysochaete, Chrysochromulina, Chrysococcus, Chrysocrinus, Chrysolepidomonas, Chrysolykos, Chrysonebula, Chrysophyta, Chrysopyxis, Chrysosaccus, Chrysophaerella, Chrysostephanosphaera, Clodophora, Clastidium, Closteriopsis, Closterium, Coccomyxa, Cocconeis, Coelastrella, Coelastrum, Coelosphaerium, Coenochloris, Coenococcus, Coenocystis, Colacium, Coleochaete, Collodictyon, Compsogonopsis, Compsopogon, Conjugatophyta, Conochaete, Coronastrum, Cosmarium, Cosmioneis, Cosmocladium, Crateriportula, Craticula, Crinalium, Crucigenia, Crucigeniella, Cryptoaulax, Cryptomonas, Cryptophyta, Ctenophora, Cyanodictyon, Cyanonephron, Cyanophora, Cyanophyta, Cyanothece, Cyanothomonas, Cyclonexis, Cyclostephanos, Cyclotella, Cylindrocapsa, Cylindrocystis, Cylindrospermum, Cylindrotheca, Cymatopleura, Cymbella, Cymbellonitzschia, Cystodinium Dactylococcopsis, Debarya, Denticula, Dermatochrysis, Dermocarpa, Dermocarpella, Desmatractum, Desmidium, Desmococcus, Desmonema, Desmosiphon, Diacanthos, Diacronema, Diadesmis, Diatoma, Diatomella, Dicellula, Dichothrix, Dichotomococcus, Dicranochaete, Dictyochloris, Dictyococcus, Dictyosphaerium, Didymocystis, Didymogenes, Didymosphenia, Dilabifilum, Dimorphococcus, Dinobryon, Dinococcus, Diplochloris, Diploneis, Diplostauron, Distrionella, Docidium, Draparnaldia, Dunaliella, Dysmorphococcus, Ecballocystis, Elakatothrix, Ellerbeckia, Encyonema, Enteromorpha, Entocladia, Entomoneis, Entophysalis, Epichrysis, Epipyxis, Epithemia, Eremosphaera, Euastropsis, Euastrum, Eucapsis, Eucocconeis, Eudorina, Euglena, Euglenophyta, Eunotia, Eustigmatophyta, Eutreptia, Fallacia, Fischerella, Fragilaria, Fragilariforma, Franceia, Frustulia, Curcilla, Geminella, Genicularia, Glaucocystis, Glaucophyta, Glenodiniopsis, Glenodinium, Gloeocapsa, Gloeochaete, Gloeochrysis, Gloeococcus, Gloeocystis, Gloeodendron, Gloeomonas, Gloeoplax, Gloeothece, Gloeotila, Gloeotrichia, Gloiodictyon, Golenkinia, Golenkiniopsis,*

Gomontia, Gomphocymbella, Gomphonema, Gomphosphaeria, Gonatozygon, Gongrosia, Gongrosira, Goniochloris, Gonium, Gonyostomum, Granulochloris, Granulocystopsis, Groenbladia, Gymnodinium, Gymnozyga, Gyrosigma, Haematococcus, Hafniomonas, Hallassia, Hammatoidea, Hannaea, Hantzschia, Hapalosiphon, Haplotaenium, Haptophyta, Haslea, Hemidinium, Hemitoma, Heribaudiella, Heteromastix, Heterothrix, Hibberdia, Hildenbrandia, Hillea, Holopedium, Homoeothrix, Hormanthonema, Hormotila, Hyalobrachion, Hyalocardium, Hyalodiscus, Hyalogonium, Hyalotheca, Hydrianum, Hydrococcus, Hydrocoleum, Hydrocoryne, Hydrodictyon, Hydrosera, Hydrurus, Hyella, Hymenomonas, Isthmochloron, Johannesbaptistia, Juranyiella, Karayevia, Kathablepharis, Katodinium, Kephyrion, Keratococcus, Kirchneriella, Klebsormidium, Kolbesia, Koliella, Komarekia, Korshikoviella, Kraskella, Lagerheimia, Lagynion, Lamprothamnium, Lemanea, Lepocinclis, Leptosira, Lobococcus, Lobocystis, Lobomonas, Luticola, Lyngbya, Malleochloris, Mallomonas, Mantoniella, Marssoniella, Martyana, Mastigocoleus, Gastogloia, Melosira, Merismopedia, Mesostigma, Mesotaenium, Micractinium, Micrasterias, Microchaete, Microcoleus, Microcystis, Microglena, Micromonas, Microspora, Microthamnion, Mischococcus, Monochrysis, Monodus, Monomastix, Monoraphidium, Monostroma, Mougeotia, Mougeotiopsis, Myochloris, Myromecia, Myxosarcina, Naegeliella, Nannochloris, Nautococcus, Navicula, Neglectella, Neidium, Nephroclamys, Nephrocytium, Nephrodiella, Nephroselmis, Netrium, Nitella, Nitellopsis, Nitzschia, Nodularia, Nostoc, Ochromonas, Oedogonium, Oligochaetophora, Onychonema, Oocardium, Oocystis, Opephora, Ophiocytium, Orthoseira, Oscillatoria, Oxyneis, Pachycladella, Palmella, Palmodictyon, Pnadorina, Pannus, Paralia, Pascherina, Paulschulzia, Pediastrum, Pedinella, Pedinomonas, Pedinopera, Pelagodictyon, Penium, Peranema, Peridiniopsis, Peridinium, Peronia, Petroneis, Phacotus, Phacus, Phaeaster, Phaeodermatium, Phaeophyta, Phaeosphaera, Phaeothamnion, Phormidium, Phycopeltis, Phyllariochloris, Phyllocardium, Phyllomitas, Pinnularia, Pitophora, Placoneis, Planctonema, Planktosphaeria, Planothidium, Plectonema, Pleodorina, Pleurastrum, Pleurocapsa, Pleurocladia, Pleurodiscus, Pleurosigma, Pleurosira, Pleurotaenium, Pocillomonas, Podohedra, Polyblepharides, Polychaetophora, Polyedriella, Polyedriopsis, Polygoniochloris, Polyepidomonas, Polytaenia, Polytoma, Polytomella, Porphyridium, Posteriochromonas, Prasinochloris, Prasinocladus, Prasinophyta, Prasiola, Prochlorphyta, Prochlorothrix, Protoderma, Protosiphon, Provasoliella, Prymnesium, Psammodictyon, Psammothidium, Pseudanabaena, Pseudenoclonium, Psuedocarteria, Pseudochate, Pseudocharacium, Pseudococcomyxa, Pseudodictyosphaerium, Pseudokephyrion, Pseudoncobyrsa, Pseudoquadrigula, Pseudosphaerocystis, Pseudostaurastrum, Pseudostaurosira, Pseudotetrastrum, Pteromonas, Punctastruata, Pyramichlamys, Pyramimonas, Pyrrophyta, Quadrichloris, Quadricoccus, Quadrigula, Radiococcus, Radiofilum, Raphidiopsis, Raphidocelis, Raphidonema, Raphidophyta, Peimeria, Rhabdoderma, Rhabdomonas, Rhizoclonium, Rhodomonas, Rhodophyta, Rhoicosphenia, Rhopalodia, Rivularia, Rosenvingiella, Rossithidium, Roya, Scenedesmus, Scherifelia, Schizochlamydella, Schizochlamys, Schizomeris, Schizothrix, Schroederia, Scolioneis, Scotiella, Scotiellopsis, Scourfieldia, Scytonema, Selenastrum, Selenochloris, Sellaphora, Semiorbis, Siderocelis, Diderocystopsis, Dimonsenia, Siphononema, Sirocladium, Sirogonium, Skeletonema, Sorastrum, Spermatozopsis, Sphaerellocystis, Sphaerellopsis, Sphaerodinium, Sphaeroplea, Sphaerozosma, Spiniferomonas, Spirogyra, Spirotaenia, Spirulina, Spondylomorum, Spondylosium, Sporotetras, Spumella, Staurastrum, Stauerodesmus, Stauroneis, Staurosira, Staurosirella, Stenopterobia, Stephanocostis, Stephanodiscus, Stephanoporos, Stephanosphaera, Stichococcus, Stichogloea, Stigeoclonium, Stigonema, Stipitococcus, Stokesiella, Strombomonas, Stylochrysalis, Stylodinium, Styloyxis, Stylosphaeridium, Surirella, Sykidion, Symploca, Synechococcus, Synechocystis, Synedra, Synochromonas, Synura, Tabellaria, Tabularia, Teilingia, Temnogametum, Tetmemorus, Tetrachlorella, Tetracyclus, Tetradesmus, Tetraedriella, Tetraedron, Tetraselmis, Tetraspora, Tetrastrum, Thalassiosira, Thamniochaete, Thorakochloris, Thorea, Tolypella, Tolypothrix, Trachelomonas, Trachydiscus, Trebouxia, Trentepholia, Treubaria, Tribonema, Trichodesmium, Trichodiscus, Trochiscia, Tryblionella, Ulothrix, Uroglena, Uronema, Urosolenia, Urospora, Uva, Vacuolaria, Vaucheria, Volvox, Volvulina, Westella, Woloszynskia, Xanthidium, Xanthophyta, Xenococcus, Zygnema, Zygnemopsis, and Zygonium.

Green non-sulfur bacteria include but are not limited to the following genera: *Chloroflexus, Chloronema, Oscillochloris, Heliothrix, Herpetosiphon, Roseiflexus*, and *Thermomicrobium*.

Green sulfur bacteria include but are not limited to the following genera: *Chlorobium, Clathrochloris*, and *Prosthecochloris*, Purple sulfur bacteria include but are not limited to the following genera: *Allochromatium, Chromatium, Halochromatium, Isochromatium, Marichromatium, Rhodovulum, Thermochromatium, Thiocapsa, Thiorhodococcus*, and *Thiocystis*, Purple non-sulfur bacteria include but are not limited to the following genera: *Phaeospirillum, Rhodobaca, Rhodobacter, Rhodomicrobium, Rhodopila, Rhodopseudomonas, Rhodothalassium, Rhodospirillum, Rodovibrio*, and *Roseospira*.

HyperPhotosynthetic conversion requires extensive genetic modification (Tables 1 and 2); thus, in preferred embodiments the parental photoautotrophic organism can be transformed with exogenous DNA.

Preferred organisms for HyperPhotosynthetic conversion include: *Arabidopsis thaliana, Panicum virgatum, Miscanthus giganteus*, and *Zea mays* (plants), *Botryococcus braunii, Chlamydomonas reinhardtii* and *Dunaliela salina* (algae), *Synechococcus* sp PCC 7002, *Synechococcus* sp. PCC 7942, *Synechocystis* sp. PCC 6803, and *Thermosynechococcus elongatus* BP-1 (cyanobacteria), *Chlorobium tepidum* (green sulfur bacteria), *Chloroflexus auranticus* (green non-sulfur bacteria), *Chromatium tepidum* and *Chromatium vinosum* (purple sulfur bacteria), *Rhodospirillum rubrum, Rhodobacter capsulatus*, and *Rhodopseudomonas palusris* (purple non-sulfur bacteria).

Propagation

Methods for cultivation of photosynthetic organisms in liquid media and on agarose-containing plates are well known to those skilled in the art (see, e.g., websites associated with ATCC, and with the Institute Pasteur). For example, *Synechococcus* sp. PCC 7002 cells (available from the Pasteur Culture Collection of Cyanobacteria) are cultured in BG-11 medium (17.65 mM $NaNO_3$, 0.18 mM $K_2HPO_4$, 0.3 mM $MgSO_4$, 0.25 mM $CaCl_2$, 0.03 mM citric acid, 0.03 mM ferric ammonium citrate, 0.003 mM EDTA, 0.19 mM $Na_2CO_3$, 2.86 mg/L $H_3BO_3$, 1.81 mg/L $MnCl_2$, 0.222 mg/L $ZnSO_4$, 0.390 mg/L $Na_2MoO_4$, 0.079 mg/L $CuSO_4$, and 0.049 mg/L $Co(NO_3)_2$, pH 7.4) supplemented with 16 µg/L biotin, 20 mM $MgSO_4$, 8 mM KCl, and 300 mM NaCl (see, e.g., website associated with the Institute Pasteur, and Price G D, Woodger F J, Badger M R, Howitt S M, Tucker L. "Identification of a SulP-type bicarbonate transporter in marine cyanobacteria. Proc Natl. Acad. Sci. USA (2004). 101(52):18228-33). Typically, cultures are maintained at 28° C. and bubbled continuously with 5% $CO_2$ under a light intensity of 120 µmol photons/$m^2$/s.

*Thermosynechococcus elongatus* BP-1 (available from the Kazusa DNA Research Institute, Japan) is propagated in BG11 medium supplemented with 20 mM TES-KOH (pH 8.2) as described [Iwai M, Katoh H, Katayama M, Ikeuchi M. "Improved genetic transformation of the thermophilic cyanobacterium, *Thermosynechococcus elongatus* BP-1." Plant Cell Physiol (2004). 45(2):171-175)]. Typically, cultures are maintained at 50° C. and bubbled continuously with 5% $CO_2$ under a light intensity of 38 µmol photons/$m^2$/s.

*Chlamydomonas reinhardtii* (available from the Chlamydomonas Center culture collection maintained by Duke University, Durham, N.C.) are grown in minimal salt medium consisting of 143 mg/L $K_2HPO_4$, 73 mg/L $KH_2PO_4$, 400 mg/L $NH_4NO_3$, 100 mg/L $MgSO_4$-7H2O, 50 mg/L $CaCl_2$-2H20, 1 mL/L trace elements stock, and 10 mL/L 2.0 M MOPS titrated with Tris base to pH 7.6 as described (Geraghty A M, Anderson J C, Spalding M H. "A 36 kilodalton limiting-CO2 induced polypeptide of *Chlamydomonas* is distinct from the 37 kilodalton periplasmic anhydrase." Plant Physiol (1990). 93:116-121). Typically, cultures are maintained at 24° C. and bubbled with 5% $CO_2$ in air, under a light intensity of 60 µmol photons/$m^2$/s.

The above define typical propagation conditions. As appropriate, incubations are performed using alternate media or gas compositions, alternate temperatures (5-75° C.), and/or light fluxes (0-5500 µmol photons/$m^2$/s).

Light is delivered through a variety of mechanisms, including natural illumination (sunlight), standard incandescent, fluorescent, or halogen bulbs, or via propagation in specially-designed illuminated growth chambers (for example Model LI15 Illuminated Growth Chamber (Sheldon Manufacturing, Inc. Cornelius, Oreg.). For experiments requiring specific wavelengths and/or intensities, light is distributed via light emitting diodes (LEDs), in which wavelength spectra and intensity can be carefully controlled (Philips).

Carbon dioxide is supplied via inclusion of solid media supplements (i.e., sodium bicarbonate) or as a gas via its distribution into the growth incubator or media. Most experiments are performed using concentrated carbon dioxide gas, at concentrations between 1 and 30%, which is directly bubbled into the growth media at velocities sufficient to provide mixing for the organisms. When concentrated carbon dioxide gas is utilized, the gas originates in pure form from commercially-available cylinders, or preferentially from concentrated sources including off-gas or flue gas from coal plants, refineries, cement production facilities, natural gas facilities, breweries, and the like.

Plasmids

Plasmids relevant to genetic engineering typically include at least two functional elements 1) an origin of replication enabling propagation of the DNA sequence in the host organism, and 2) a selective marker (for example an antibiotic resistance marker conferring resistance to ampicillin, kanamycin, zeocin, chloramphenicol, tetracycline, spectinomycin, and the like). Plasmids are often referred to as "cloning vectors" when their primary purpose is to enable propagation of a desired heterologous DNA insert. Plasmids can also include cis-acting regulatory sequences to direct transcription and translation of heterologous DNA inserts (for example, promoters, transcription terminators, ribosome binding sites); such plasmids are frequently referred to as "expression vectors." When plasmids contain functional elements that allow for propagation in more than one species, such plasmids are referred to as "shuttle vectors." Shuttle vectors are well known to those in the art. For example, pSE4 is a shuttle vector that allows propagation in *E. coli* and *Synechococcus* [Maeda S, Kawaguchi Y, Ohy T, and Omata T. J. Bacteriol. (1998). 180:4080-4088]. Shuttle vectors are particularly useful in the present invention to allow for facile manipulation of genes and regulatory sequences in *E. coli* prior to transformation into the photoautotrophic organism of interest.

Transformation Techniques

Standard methods for transformation of prokaryotes are well known to those skilled in the art [Berger and Kimmel, Guide to Molecular Cloning Techniques, Methods in Enzymology volume 152 Academic Press, Inc., San Diego, Calif.; Sambrook et al. (1989) Molecular Cloning—A Laboratory Manual (2nd ed.) Vol. 1-3, Cold Spring Harbor Laboratory, Cold Spring Harbor Press, N.Y.; and Current Protocols in Molecular Biology, F. M. Ausubel et al., eds., Current Protocols, a joint venture between Greene Publishing Associates, Inc. and John Wiley & Sons, Inc., (through and including the 1997 Supplement)].

Many prokaryotic organisms are naturally competent; others can be rendered competent by chemical treatments. Non-limiting examples of transformation techniques include direct incubation in the presence of exogenous DNA, transformation by heat-shock, transformation by electroporation, transformation by biolistic particle bombardment, transformation via addition of lipids or fusogenic agents (i.e., polyethylene glycol), conjugation with a heterologous microorganism, or transduction via viral particles.

*Synechococcus* sp. PCC 7002 cells are transformed according to the optimized protocol previously described [Essich E S, Stevens Jr E, Porter R D "Chromosomal Transformation in the Cyanobacterium *Agmenellum quadruplicatum*". J Bacteriol (1990). 172(4):1916-1922]. Cells are grown in Medium A (18 g/L NaCl, 5 g/L $MgSO_4.7H_2O$, 30 mg/L $Na_2EDTA$, 600 mg/L KCl, 370 mg/L $CaCl_2.2H_2O$, 1 g/L $NaNO_3$, 50 mg/L $KH_2PO_4$, 1 g/L Trizma base pH 8.2, 4 µg/L Vitamin B12, 3.89 mg/L $FeCl_3$ $6H_2O$, 34.3 mg/L $H_3BO_3$, 4.3 mg/L $MnCl_2.4H_2O$, 315 µg/L $ZnCl_2$, 30 µg/L $MoO_3$, 3 µg/L $CuSO_4.5H_2O$, 12.2 µg/L $CoCl_2.6H_2O$) [Stevens S E, Patterson C O P, and Myers J. "The production of hydrogen peroxide by green algae: a survey." J. Phycology (1973). 9:427-430] plus 5 g/L of $NaNO_3$ to approximately $10^8$ cells/mL. Nine volumes of cells are mixed with 1 volume of 1-10 µg/mL DNA in 0.15 M NaCl/0.015 M $Na_3$citrate and incubated at 27-30° C. for 3 hours before addition of 1 volume of DNaseI to a final concentration of 10 µg/mL. The cells are plated in 2.5 mL of 0.6% medium A overlay agar that was tempered at 45° C. and incubated. Cells are challenged with antibiotic by underlaying 2.0 mL of 0.6% medium A agar containing appropriate concentration of antibiotic with a sterile Pasteur pipette. Transformants are picked 3-4 days later. Selections are typically performed using 200 µg/ml kanamycin, 8 µg/ml chloramphenicol, 10 µg/ml spectinomycin on solid media, whereas 150 µg/ml kanamycin, 7 µg/ml chloramphenicol, and 5 µg/ml spectinomycin are employed in liquid media.

*Thermosynechococcus elongatus* BP-1 cells are transformed according to the optimized protocol previously described [Iwai M, Katoh H, Katayama M, and Ikeuchi M. "Improved genetic transformation of the thermophilic cyanobacterium *Thermosynechococcus elongatus* BP-1. Plant Cell Physiol (2004). 45(2):171-175]. Mid-exponential phase cultures are incubated with exogenous DNA (typically 3-20 µg) and electroporated at a field strength of 10 kV/cm using a BioRad Gene Pulsur Xcell (Bio-Rad Laboratories, Hercules, Calif.). Following electroporation, the cells are recovered in 1 ml BG11 medium for 24-hrs at 45° C. Cells are plated directly on BG11 plates containing the appropriate antibiotic or optionally pre-mixed with BG11 medium containing 0.35% (w/v) melted agar (Difco, USA).

Transformation typically involves incubation of recipient cells with purified plasmid DNA isolated from *E. coli*. In contrast, bacterial conjugation provides an alternate means to directly transfer DNA from one bacterial species to another. For example, techniques enabling conjugation between *E. coli* and cyanobacteria including *Synechocystic* PCC 6803 and PCC 6714 and *Synechococcus* PCC 7942 and PCC 6301, as well as thermophilic *Synechococcus elongatus* have been described [Marraccini P, Bulteau S, Cassier-Chauvat C, Mermet-Bouvier P, and Chauvat F. "A conjugative plasmid vector for promoter analysis in several cyanobacteria of the genera *Synechococcus* and *Synechocystis*." Plant Molecular Biology (1993). 23(4):905-909; Muhlenhoff U and Chauvat; "Gene transfer and manipulation in the thermophilic cyanobacterium *Synechococcus elongatus*." Molecular and General Genetics MGG (1996). 252(1-2):93-100

Techniques related to the transformation of eukaryotic photoautotrophs are known to those skilled in the art. Such methods have been described in textbooks related to molecular biology (see Packer & Glaser, 1988, "Cyanobacteria", Meth. Enzymol., Vol. 167; Weissbach & Weissbach, 1988, "Methods for plant molecular biology," Academic Press, New York, Sambrook, Fritsch & Maniatis, 1989, "Molecular Cloning: A laboratory manual," 2nd edition Cold Spring Harbor Laboratory Press, Cold Spring Harbor, N.Y.; and Clark M S, 1997, Plant Molecular Biology, Springer, N.Y.) and in "Methods and tools for transformation of eukaryotic algae" U.S. Pat. No. 6,027,900.

A variety of approaches can be employed for transformation of *Chlamydomonas reinhardtii* cells. Transformation of the *Chlamydomonas reinhardtii* nuclear compartment is performed as described [Kindle K L. "High-frequency nuclear transformation of *Chlamydomonas reinhardtii*." Proc Natl Acad Sci (1990). 87:1228-1232]. In brief, cells are grown to a concentration of $1.5 \times 10^6$ per ml, pelleted, and resuspended in 5% (v/v) polyethylene glycol (PEG, $M_r$ 6000) from Sigma-Aldrich (St. Louis, Mo.). Subsequently, the resuspended cells are incubated with linear or circular plasmid DNA and agitated in the presence of 300 mg of 0.5-mm glass beads for 10-30 seconds at maximum speed using a Genie Vortex II mixer (Thermo Fisher Scientific, Pittsburgh, Pa.). Cells are immediately plated on agarose plates containing the appropriate antibiotic or nutrient selection. Alternately, *Chlamydomonas reinhardtii* cells are plated directly onto agarose plates and bombarded with 500 μg of tungsten microprojectiles coated with 1 μg of plasmid DNA using the Bio-Rad PDS-1000He particle-delivery system (Bio-Rad Laboratories; Hercules, Calif.), as previously described [Sodeinde O A and Kindle K L. "Homologous recombination in the nuclear genome of *Chlamydomonas reinhardtii*." Proc Natl Acad Sci (1993). 90:9199-9203].

*Chlamydomonas reinhardtii* chloroplasts are transformed as described (Kindle K L, Richards K L, Stem D B. "Engineering the chloroplast genome: Techniques and capabilities for chloroplast transformation in *Chlamydomonas reinhardtii*. Proc Natl Acad. Sci. (2001). 88:1721-1725). In brief, cells are grown to mid log phase, optionally in the presence of 0.5 mM 5-fluorodeoxyuridine, and agitated with single or double-stranded plasmid DNA in the presence of 300 mg of 0.5-mm glass beads for 15-30 seconds at maximum speed using a Genie Vortex II mixer. Following agitation, cells are immediately plated on selective agar plates containing the appropriate concentration of antibiotics. Typically, 100 μg/ml of spectinomycin is used.

*Chlamydomonas reinhardtii* mitochondria are transformed as described (Remacle C, Cardol P, Coosemans N, Galsne M, and Bonnefoy N. "High-efficiency biolistic transformation of *Chlamydomonas* mitochondria can be used to insert mutations in complex I genes." Proc Natl Acad Sci (2006). 103: 4771-4776.] Briefly, cells are grown in liquid Tris Acetate Phosphate media (TAP) [http://openwetware.org/wiki/Media_formula] to a concentration of $2-3 \times 10^6$ cells/ml and $10^8$ cells are spread onto TAP plates and bombarded with tungsten beads coated with DNA using the Bio-Rad PDS-1000He apparatus under 1100 psi pressure and a partial chamber vacuum of at least 29 inches Hg. Plates are positioned approximately 7 cm from the macrocarrier assembly, optionally employing stopping screens to increase transformation efficiencies.

Tables 1 and 2 define preferred genes to convey HyperPhotosynthetic properties to an existing photoautotrophic organism.

Table 1 lists genes which are overexpressed to enhance carbon fixation rates, thermotolerance, pH tolerance, flue gas tolerance, salt tolerance, light harvesting efficiencies, reducing power generation, and nutrient independence, together with information on associated pathways, Enzyme Commission (EC) Numbers, exemplary gene names, source organism, GenBank accession numbers, and homologs from alternate sources. When the parental organism encodes a gene with the indicated enzymatic activity, it is nevertheless useful to overexpress these components to improve $CO_2$ fixation. In one embodiment, the native enzyme sequence is overexpressed. In preferred embodiments, it is useful to overexpress an exogenous gene, which allows for more explicit regulatory control in the bioprocess and a means to potentially mitigate the effects of central metabolism regulation, which is focused around the native genes explicitly.

The nucleotide sequences for the indicated genes (or DNA sequences that encode the identical or homologous polypeptides, but encompassing nucleotide substitutions to 1) alter expression levels based on the host organism's codon usage table; 2) add or remove secondary structure; 3) add or remove restriction endonuclease recognition sequences; and/or 4) facilitate gene synthesis and assembly) are assembled by Codon Devices Inc (Cambridge, Mass.). Alternate providers including DNA2.0 (Menlo Park, Calif.), Blue Heron Biotechnology (Bothell, Wash.), and Geneart (Regensburg, Germany), are used as noted. Sequences untenable by commercial sources may be prepared using polymerase chain reaction (PCR) from DNA or cDNA samples, or cDNA/BAC libraries. Inserts are initially propagated and sequenced in a cloning vector, such as pUC19. Importantly, primary synthesis and sequence verification of each gene of interest in pUC19 provides flexibility to transfer each unit in various combinations to alternate destination vectors to drive transcription and translation of the desired enzymes. Specific and/or unique cloning sites are included at the 5' and 3' ends of the open reading frames (ORFs) to facilitate molecular transfers.

The required metabolic pathways are initially encoded in expression cassettes driven by constitutive promoters which are always "on." Many such promoters are known, for example the spc ribosomal protein operon ($P_{spc}$), the beta-lactamase gene promoter of pBR322 ($P_{bla}$), the bacteriophage lambda $P_L$ promoter, the replication control promoters of plasmid pBR322 ($P_{RNAI}$ or $P_{RNAII}$), or the P1 or P2 promoters of the rrnB ribosomal RNA operon [Liang S T, Bipatnath M, Xu Y C, Chen S L, Dennis P, Ehrenber M, Bremer H. Activities of Constitutive Promoters in *Escherichia coli*. J. Mol Biol (1999). Vol 292, Number 1, pgs 19-37], the Chlorella virus promoters described in U.S. Pat. No. 5,846,744 ["Chlorella virus promoters"], the cauliflower mosaic virus 35S promoter [Zheng X, Deng W, Luo K, Duan H, Chen Y, McAvoy R, Song S, Pei Y, Li Y. "The cauliflower mosaic virus (CaMV) 35S promoter sequence alters the level and patterns of activity of adjacent tissue- and organ-specific gene promoters." Plant Cell Rep (2007). 26(8):1195-1203], the constitutive petH promoter of Anabaena [Valladares A, Muro-Pastor A M, Fillat M F, Herrero A, Flores E. "Constitutive and nitrogen-regulated promoters of the petH gene encoding ferredoxin: NADP+ reductase in the heterocyst-forming cyanobacterium *Anabaena* sp." FEBS Lett (1999). 449(2-3):159-64], the RbcS2 promoter of *Chlamydomonas* [Leon R, Couso I, Fernandez E. "Metabolic engineering of ketocarotenoids biosynthesis in the unicellular microalgae *Chlamydomonas reinhardtii*." J Biotechnol (2007). 130(2):143-152], and the core promoter sequence of psbA from *Microcystis aeruginosa* K-81 [Shibato J, Asayama M, Shirai M. "Specific recognition of the cyanobacterial psbA promoter by RNA polymerases containing principal sigma factors." Biochim. Biophys Acta (1998). 1442(2-3):296-303].

As necessary, after designing and testing pathways, the strength of constitutive promoters are "tuned" to increase or decrease levels of transcription to optimize a network, for example, by modifying the conserved −35 and −10 elements or the spacing between these elements [Alper H, Fischer C, Nevoigt E, Stephanopoulus G. "Tuning genetic control through promoter engineering." PNAS (2005). 102(36): 12678-12783; Jensen P R and Hammer K. "The sequence of spacers between the consensus sequences modulates the strength of prokaryotic promoters." Appl Environ Microbiol (1998). 64(I):82-87; Mijakovic I, Petranovic D, Jensen P R. Tunable promoters in system biology. Curr Opin Biotechnol (2005). 16:329-335; De Mey M, Maertens J, Lequeux G J, Soetaert W K, Vandamme E J. "Construction and model-based analysis of a promoter library from *E. coli*: an indispensable tool for metabolic engineering." BMC Biotechnology (2007) 7:34].

When constitutive expression proves non-optimal (i.e., has deleterious effects, is out of sync with the network, etc.) inducible promoters are used. Inducible promoters are "off" (not transcribed) prior to addition of an inducing agent, frequently a small molecule or metabolite. Examples of suitable inducible promoter systems include the arabinose inducible $P_{bad}$ [Khlebnikov A, Datsenko K A, Skaug T, Wanner B L, Keasling J D. "Homogeneous expression of the P(BAD) promoter in *Escherichia coli* by constitutive expression of the low-affinity high-capacity AraE transporter." Microbiology (2001). 147 (Pt 12): 3241-7], the rhamnose inducible rha$P_{BAD}$ promoter [Haldimann A, Daniels L, Wanner B. J Bacteriol (1998). "Use of new methods for construction of tightly regulated arabinose and rhamnose promoter fusions in studies of the *Escherichia coli* phosphate regulon." 180:1277-1286], the propionate inducible pPRO [Lee S K and Keasling J D. "A propionate-inducible expression system for enteric bacteria." Appl Environ Microbiol (2005). 71(11):6856-62)], the IPTG-inducible lac promoter [Gronenborn. Mol Gen Genet (1976). "Overproduction of phage lambda repressor under control of the lac promoter of *Escherichia coli*." 148:243-250], the synthetic tac promoter [De Boer H A, Comstock L J, Vasser M. "The tac promoter: a functional hybrid derived from the trp and lac promoters." PNAS (1983). 80:21-25], the synthetic trc promoter [Brosius J, Erfle M, Storella J. "Spacing of the −10 and −35 regions in the tac promoter. Effect on its in vivo activity." J Biol Chem (1985). 260:3539-3541], or the T7 RNA polymerase system [Studier F W and Moffatt B A. "Use of bacteriophage T7 RNA polymerase to direct selective high-level expression of cloned genes." J Mol Biol (1986]. 189:113-130, the tetracycline or anhydrotetracycline-inducible tetA promoter/operator system [Skerra A. "Use of the tetracycline promoter for the tightly regulated production of a murine antibody fragment in *Escherichia coli*" Gene (1994). 151:131-135], the nickel inducible Cpx1 and Cyc6 promoters of *Chlamydomonas reinhardtii* [Quinn J M, Kropat J, Merchant S. "Copper response element and Crr1-dependent nickel-responsive promoter for induced, reversible gene expression in *Chlamydomonas reinhardtii*." Eukaryotic Cell (2003). 2(5):995-1002], the nitrite-inducible nirA promoter of *Synechococcus* [Qi Q, Hao M, Ng W, Slater S C, Baszis S R, Weiss J D, and Valentin H E. "Application of the *Synechococcus* nirA promoter to establish an inducible expression system for engineering the *Synechocystis* tocopherol pathway." Appl. Environ. Microb (2005) 71(10):5678-5684], the sulfur-responsive arylsulfatase promoter of *Volvox* [Hallman A and Sumper M. "Reporter genes and highly regulated promoters as tools for transformation experiments in *Volvox carteri*." Proc Natl Acad Sci (1994). 91(24):11562-11566]. These and other naturally-occurring or synthetically-derived inducible promoters are employed (see, e.g., U.S. Pat. No. 7,235,385; Methods for enhancing expression of recombinant proteins).

Alternate origins of replication are selected to provide additional layers of expression control. The number of copies per cell contributes to the "gene dosage effect." For example, the high copy pMB1 or colE1 origins are used to generate 300-1000 copies of each plasmid per cell, which contributes to a high level of gene expression. In contrast, plasmids encoding low copy origins, such as pSC101 or p15A, are leveraged to restrict copy number to about 1-20 copies per cell. Techniques and sequences to further modulate plasmid copy number are known (see, e.g., U.S. Pat. No. 5,565,333, Plasmid replication origin increasing the copy number of plasmid containing said origin; U.S. Pat. No. 6,806,066, Expression vectors with modified ColE1 origin of replication for control of plasmid copy number). Certain organisms, including *Synechococcus* sp. PCC 7002, encode endogenous plasmids with varying copy numbers [Yano S, Kawata Y, Kojima H. "Salinity-dependent copy number changes of endogenous plasmids in *Synechococcus* sp. PCC 7002]; thus, gene dosage can be modified by targeting expression cassettes to distinct endogenous plasmids.

Expression levels are also optimized by modulation of translation efficiency. In *E. coli*, a Shine-Dalgarno (SD) sequence [Shine J and Dalgarno L. Nature (1975) "Determination of cistron specificity in bacterial ribosomes." 254(5495):34-8] is a consensus sequence that directs the ribosome to the mRNA and facilitates translation initiation by aligning the ribosome with the start codon. Modulation of the SD sequence is used to increase or decrease translation efficiency as appropriate [de Boer H A, Comstock L J, Hui A, Wong E, Vasser M. Gene Amplif Anal (1983). "Portable Shine-Dalgarno regions; nucleotides between the Shine-Dalgarno sequence and the start codon effect the translation efficiency". 3: 103-16; Mattanovich D, Weik R, Thim S, Kramer W, Bayer K, Katinger H. Ann N Y Acad Sci (1996). "Optimization of recombinant gene expression in *Escherichia coli*." 782:182-90.]. Of note, a high level of translation can be observed in certain contexts in the absence of an SD sequence [Mutsuda M and Sugiura M. "Translation initiation of cyanobacterial rbcS mRNAs requires the 38-kDa ribosomal protein S1 but not the Shine-Dalgarno sequence." J Biol Chem (2006). 281(50):38314-38321; Xu J, Mironova R, Ivanov I G, Abouhaidar M G. J Basic Microbiol (1999). "A polylinker-derived sequence, PL, highly increased translation efficiency in *Escherichia coli*." 39(1):51-60]. Secondary mRNA structure is engineered in or out of the genes of interest to modulate expression levels [Klinkert B, Elles I, Nickelsen J. "Translation of chloroplast psbD mRNA in *Chlamydomonas* is controlled by a secondary structure blocking the AUG start codon." Nucleic Acids Res (2006). 34(1):384-94; Cebe R and Geiser M. Protein Expr Purif (2006). "Rapid and easy thermodynamic optimization of 5'-end of mRNA dramatically increases the level of wild type protein expression in *Escherichia coli*." 45(2):374-80; Zhang W, Xiao W, Wei H, Zhang J, Tian Z. Biochem Biophys Res Commun (2006). "mRNA secondary structure at start AUG codon is a key limiting factor for human protein expression in *Escherichia coli*." 349(1):69-78; Voges D, Watzele M, Nemetz C, Wizemann S, Buchberger B. Biochem Biophys Res Commun (2004). "Analyzing and enhancing mRNA translational efficiency in an *Escherichia coli* in vitro expression system." 318(2):601-14]. Codon usage is also manipulated to increase or decrease levels of translation [Deng T. FEBS Lett (1997). "Bacterial expression and purification of biologically active mouse c-Fos proteins by selective codon optimization." 409(2):269-72; Hale R S and Thompson G. Protein Expr Purif (1998). "Codon optimization of the gene encoding a domain from human type 1 neurofibromin protein results in a threefold improvement in expression level in *Escherichia coli*." 12(2):185-8].

In some embodiments, each gene of interest is expressed on a unique plasmid. In preferred embodiments, the desired biosynthetic pathways are encoded on multi-cistronic plasmid vectors. Useful expression vectors are designed internally and synthesized by external gene synthesis providers.

Optimizations

The below biosynthetic pathways and modules are first tested and optimized using episomal plasmids described above. Non-limiting optimizations include promoter swapping and tuning, ribosome binding site manipulation, alteration of gene order (e.g., gene ABC versus BAC, CBA, CAB, BCA), co-expression of molecular chaperones, random or targeted mutagenesis of gene sequences to increase or decrease activity, folding, or allosteric regulation, expression of gene sequences from alternate species, codon manipulation, addition or removal of intracellular targeting sequences such as signal sequences, and the like.

Each gene or module is optimized individually, or alternately, in parallel. Functional promoter and gene sequences are subsequently integrated into the photoautotrophic host's chromosome to enable stable propagation in the absence of selective pressure (i.e., inclusion of antibiotics) using standard techniques known to those skilled in the art.

Table 2 lists genes which are downregulated or knocked-out to enhance carbon fixation rates, thermotolerance, pH tolerance, flue gas tolerance, salt tolerance, light harvesting efficiencies, reducing power generation, and nutrient independence, together with information on associated pathways, Enzyme Commission (EC) Numbers, exemplary gene names, source organism, and GenBank accession numbers.

Disruption of Endogenous DNA Sequences

In certain instances, chromosomal DNA sequence native (i.e., "endogenous") to the host organism are altered. Manipulations are made to non-coding regions, including promoters, ribosome binding sites, transcription terminators, and the like to increase or decrease expression of specific gene product(s). In alternate embodiments, the coding sequence of an endogenous gene is altered to affect stability, folding, activity, or localization of the intended protein. Alternately, specific genes can be entirely deleted or "knocked-out." Techniques and methods for such manipulations are known to those skilled in the art [Nelson J A, and Lefebvre P A. "Targeted disruption of the NIT8 gene in *Chlamydomonas reinhardtii*." Mol Cell Bio (1995). 15(10):5762-5769; Hanson T E and Tabita F R. "A ribulose-1,5-bisphosphate carboxylase/oxygenase (RubisCO)-like protein from *Chlorobium tepidum* that is involved with sulfur metabolism and the response to oxidative stress." Proc Natl Acad Sci (2001). 98(8):4397-4402; Sugita C, Mutsuda M, Sugiura M, Sugita M. "Targeted deletion of genes for eukaryotic RNA-binding proteins, Rbp1 and Rbp2, in the cyanobacterium *Synechococcus* sp. Strain PCC7942: Rbp1 is indispensable for cell growth at low temperatures." FEMS Microbiol Letters (1999). 176(1): 155-161; Kirilovsky D, Roncel M, Boussac A, Wilson A, Zurita J L, Ducruet J, Bottin H, Sugiura M, Ortega J M, Rutherford A W. "Cytochrome c550 in the cyanobacterium *Thermosynechococcus elongatus*. Study of Redox mutants." J Biol Chem (2004). 279(51):52869-80; Datsenko K A, Wanner B L. PNAS (2000). "One-step inactivation of chromosomal genes in *E. coli* K-12 using PCR Products." 97: 6640-6645; Link A J et al. J Bacteriol (1997). "Methods for generating precise deletions and insertions in the genome of wild-type *Escherichia coli*: Application to open reading frame characterization." 179:6228-6237; Baba T et al. Mol Syst Biol (2006). Construction of *Escherichia coli* K-12 in-frame, single gene knockout mutants: the Keio collection." 2:2006.0008; Tischer B K, von Einem J, Kaufer B, Osterrieder N. Biotechniques (2006). "Two-step red-mediated recombination for versatile high-efficiency markerless DNA manipulation in *Escherichia coli*." 40(2):191-7; McKenzie G J, Craig N L. BMC Microbiol (2006). Fast, easy and efficient: site-specific insertion of transgenes into enterobacterial chromosomes using Tn7 without need for selection of the insertion event." 6:39].

In certain embodiments, post-transcriptional gene silencing (PTGS) is employed to reduce the expression level of an endogenous gene via expression of a heterologous RNA sequence, frequently antisense to the gene requiring disruption [Lechtreck K, Rostmann J, and Grunow A. "Analysis of *Chlamydomonas* SF-assemblin by GFP tagging and expression of antisense constructs." J. Cell Sci (2002). 115:1511-1522; Smith N A, Singh S P, Wang M, Stotjesdijk P A, Green A G, and Waterhouse P M. "Total silencing by intron-spliced hairpin RNAs." Nature (2000). 407:319-320; Furhmann M, Stahlberg A, Govorunova E, Rank S, and Hegeman P. "The abundant retinal protein of the *Chlamydomonas* eye is not the photoreceptor for phototaxis and photophobic responses." J. Cell Sci (2001). 114:3857-3863; Rohr J, Sarkar N, Balenger S Jeong B R, Cerutti H. "Tandem inverted repeat system for selection of effective transgenic RNAi strains in *Chlamydomonas*" Plant J (2004). 40(4):611-21].]

In other embodiments, expression of naturally encoded or exogenous small RNA or microRNA species is employed to downregulate endogenous gene expression [Molnar A, Schwach F, Studholme D J, Tgyenemann E C, and Baulcombe D C. "miRNAs control gene expression in the single-cell alga *Chlamydomonas reinhardtii*." Nature (2007). 447 (7148):1126-9; Zhao T, Li G, Mi S, Li S, Hannon G J, Wang X J, Qi Y. "A complex system of small RNAs in the unicellular green alga *Chlamydomonas reinhardtii*." Genes Dev (2007). 21(10):1190-203].

Selections and Assays

Selective pressure provides a valuable means for testing and optimizing the HyperPhotosynthetic organisms. The ability to survive under ever increasing temperatures provides evidence for successful implementation of the improved thermotolerance module. The ability to grow in media bubbled with flue gas (or an artificial gas formulation that approximates flue gas composition) confirms the successful implementation of the improved flue gas tolerance module. The ability to replicate more rapidly than the wild-type counterparts confirms the successful implementation of the improved $CO_2$ fixation module. The ability to survive and replicate in media lacking Vitamin $B_{12}$ as a media supplement confirms the successful implementation of the Vitamin $B_{12}$ module.

If desired, additional genetic variation can be introduced prior to selective pressure by treatment with mutagens, such as ultra-violet light, alkylators [e.g., ethyl methanesulfonate (EMS), methyl methane sulfonate (MMS), diethylsulfate (DES), and nitrosoguanidine (NTG, NG, MMG)], DNA intercalators (e.g., ethidium bromide), nitrous acid, base analogs, bromouracil, transposons, and the like.

Alternately or in addition to selective pressure, pathway activity can be monitored following growth under permissive (i.e., non-selective) conditions by measuring specific product output via various metabolic labeling studies (including radioactivity), biochemical analyses (Michaelis-Menten), gas chromatography-mass spectrometry (GC/MS), mass spectrometry, matrix assisted laser desorption ionization time-of-flight mass spectrometry (MALDI-TOF), capillary electrophoresis (CE), and high pressure liquid chromatography (HPLC).

Fermentation Methods

The production and isolation of products from HyperPhotosynthetic organisms can be enhanced by employing specific fermentation techniques. An essential element to maximizing production while reducing costs is increasing the percentage of the carbon source that is converted to such products. Carbon atoms, during normal cellular lifecycles, go to cellular functions including producing lipids, saccharides, proteins, and nucleic acids. Reducing the amount of carbon necessary for non-product related activities can increase the efficiency of output production. This is achieved by first growing microorganisms to a desired density. A preferred density would be that achieved at the peak of the log phase of growth. At such a point, replication checkpoint genes can be harnessed to stop the growth of cells. Specifically, quorum sensing mechanisms (reviewed in Camilli, A. and Bassler, B. L *Science* 311:1113; Venturi, V. *FEMS Microbio Rev* 30: 274; and Reading, N. C. and Sperandio, V. *FEMS Microbiol Lett* 254: 1) can be used to activate genes such as p53, p21, or other checkpoint genes. Genes that can be activated to stop cell replication and growth in *E. coli* include umuDC genes, the overexpression of which stops the progression from exponential phase to stationary growth (Murli, S., Opperman, T., Smith, B. T., and Walker, G. C. 2000 *Journal of Bacteriology* 182: 1127.). UmuC is a DNA polymerase that can carry out translesion synthesis over non-coding lesions—the mechanistic basis of most UV and chemical mutagenesis. The umuDC gene products are required for the process of translesion synthesis and also serve as a DNA damage checkpoint. UmuDC gene products include UmuC, UmuD, umuD', UmuD'$_2$C, UmuD'$_2$ and UmuD$_2$. Simultaneously, the product synthesis genes are activated, thus minimizing the need for critical replication and maintenance pathways to be used while the product is being made.

Alternatively, cell growth and product production can be achieved simultaneously. In this method, cells are grown in bioreactors with a continuous supply of inputs and continuous removal of product. Batch, fed-batch, and continuous fermentations are common and well known in the art and examples can be found in Thomas D. Brock in Biotechnology: A Textbook of Industrial Microbiology, Second Edition (1989) Sinauer Associates, Inc., Sunderland, Mass., or Deshpande, Mukund V., Appl. Biochem. Biotechnol (1992), 36:227.

In all production methods, inputs include carbon dioxide, water, and light. The carbon dioxide can be from the atmosphere or from concentrated sources including offgas or flue gas from coal plants, refineries, cement production facilities, natural gas facilities, breweries, and the like. Water can be no-salt, low-salt, marine, or high salt. Light can be solar or from artificial sources including incandescent lights, LEDs, fiber optics, and fluorescent lights.

Light-harvesting organisms are limited in their productivity to times when the solar irradiance is sufficient to activate their photosystems. In a preferred light-harvesting organism bioprocess, cells are enabled to grow and produce product with light as the energetic driver. When there is a lack of sufficient light, cells can be induced to minimize their central metabolic rate. To this end, the inducible promoters specific to product production can be heavily stimulated to drive the cell to process its energetic stores in the product of choice. With sufficient induction force, the cell will minimize its growth efforts, and use its reserves from light harvest specifically for product production. Nonetheless, net productivity is expected to be minimal during periods when sufficient light is lacking as no to few photons are net captured.

In a preferred embodiment, the cell is engineered such that the final product is released from the cell. In embodiments where the final product is released from the cell, a continuous process can be employed. In this approach, a reactor with organisms producing desirable products can be assembled in multiple ways. In one embodiment, the reactor is operated in bulk continuously, with a portion of media removed and held in a less agitated environment such that an aqueous product will self-separate out with the product removed and the remainder returned to the fermentation chamber. In embodiments where the product does not separate into an aqueous phase, media is removed and appropriate separation techniques (e.g., chromatography, distillation, etc.) are employed.

In an alternate embodiment, the product is not secreted by the cells. In this embodiment, a batch-fed fermentation approach is employed. In such cases, cells are grown under continued exposure to inputs (light, water, and carbon dioxide) as specified above until the reaction chamber is saturated with cells and product. A significant portion to the entirety of the culture is removed, the cells are lysed, and the products are isolated by appropriate separation techniques (e.g., chromatography, distillation, filtration, centrifugation, etc.).

In a preferred embodiment, the fermentation chamber will enclose a fermentation that is undergoing a continuous reductive fermentation. In this instance, a stable reductive environment is created. The electron balance is maintained by the release of carbon dioxide (in gaseous form). Augmenting the NAD/H and NADP/H balance, as described above, also can be helpful for stabilizing the electron balance.

Detection and Analysis of Gene and Cell Products

Any of the standard analytical methods, such as gas chromatography-mass spectrometry, and liquid chromatography-mass spectrometry, HPLC, capillary electrophoresis, Matrix-Assisted Laser Desorption Ionization time of flight-mass spectrometry, etc., can be used to analyze the levels and the identity of the product produced by the modified organisms of the present invention.

The ability to detect formation of a new, functional biochemical pathway in the HyperPhotosynthetic cell is important to the practice of the subject methods. In general, the assays are carried out to detect heterologous biochemical transformation reactions of the host cell that produce, for example, small organic molecules and the like as part of a de novo synthesis pathway, or by chemical modification of molecules ectopically provided in the host cell's environment. The generation of such molecules by the host cell can be detected in "test extracts," which can be conditioned media, cell lysates, cell membranes, or semi-purified or purified fractionation products thereof. The latter can be, as described above, prepared by classical fractionation/purification techniques, including phase separation, chromatographic separation, or solvent fractionation (e.g., methanol ethanol, acetone, ethyl acetate, tetrahydrofuran (THF), acetonitrile, benzene, ether, bicarbonate salts, dichloromethane, chloroform, petroleum ether, hexane, cyclohexane, diethyl ether and the like). Where the assay is set up with a responder cell to test the effect of an activity produced by the host cell on a whole cell rather than a cell fragment, the host cell and test cell can be co-cultured together (optionally separated by a culture insert, e.g. Collaborative Biomedical Products, Bedford, Mass., Catalog #40446).

In certain embodiments, the assay is set up to directly detect, by chemical or photometric techniques, a molecular species which is produced (or destroyed) by a biosynthetic pathway of the recombinant host cell. Such a molecular species' production or degradation must be dependent, at least in part, on expression of the heterologous genomic DNA. In other embodiments, the detection step of the subject method involves characterization of fractionated media/cell lysates (the test extract), or application of the test extract to a biochemical or biological detection system. In other embodiments, the assay indirectly detects the formation of products of a heterologous pathway by observing a phenotypic change in the host cell, e.g. in an autocrine fashion, which is dependent on the establishment of a heterologous biosynthetic pathway in the host cell.

In certain embodiments, analogs related to a known class of compounds are sought, as for example analogs of alkaloids, aminoglycosides, ansamacrolides, beta-lactams (including penicillins and cephalosporins), carbapenems, terpinoids, prostanoid hormones, sugars, fatty acids, lincosaminides, macrolides, nitrofurans, nucleosides, oligosaccharides, oxazolidinones, peptides and polypeptides, phenazines, polyenes, polyethers, quinolones, tetracyclines, streptogramins, sulfonamides, steroids, vitamins and xanthines. In such embodiments, if there is an available assay for directly identifying and/or isolating the natural product, and it is expected that the analogs would behave similarly under those conditions, the detection step of the subject method can be as straightforward as directly detecting analogs of interest in the cell culture media or preparation of the cell. For instance, chromatographic or other biochemical separation of a test extract may be carried out, and the presence or absence of an analog detected, e.g., spectrophotometrically, in the fraction in which the known compounds would occur under similar conditions. In certain embodiments, such compounds can have a characteristic fluorescence or phosphorescence which can be detected without any need to fractionate the media and/or recombinant cell.

In related embodiments, whole or fractionated culture media or lysate from a recombinant host cell can be assayed by contacting the test sample with a heterologous cell ("test cell") or components thereof. For instance, a test cell, which can be prokaryotic or eukaryotic, is contacted with conditioned media (whole or fractionated) from a recombinant host cell, and the ability of the conditioned media to induce a biological or biochemical response from the test cell is assessed. For instance, the assay can detect a phenotypic change in the test cell, as for example a change in: the transcriptional or translational rate or splicing pattern of a gene; the stability of a protein; the phosphorylation, prenylation, methylation, glycosylation or other post translational modification of a protein, nucleic acid or lipid; the production of 2nd messengers, such as cAMP, inositol phosphates and the like. Such effects can be measured directly, e.g., by isolating and studying a particular component of the cell, or indirectly such as by reporter gene expression, detection of phenotypic markers, and cytotoxic or cytostatic activity on the test cell.

When screening for bioactivity of test compounds produced by the recombinant host cells, intracellular second messenger generation can be measured directly. A variety of intracellular effectors have been identified. For instance, for screens intended to isolate compounds, or the genes which encode the compounds, as being inhibitors or potentiators of receptor- or ion channel-regulated events, the level of second messenger production can be detected from downstream signaling proteins, such as adenylyl cyclase, phosphodiesterases, phosphoinositidases, phosphoinositol kinases, and phospholipases, as can the intracellular levels of a variety of ions.

In still other embodiments, the detectable signal can be produced by use of enzymes or chromogenic/fluorescent probes whose activities are dependent on the concentration of a second messenger, e.g., such as calcium, hydrolysis products of inositol phosphate, cAMP, etc.

Many reporter genes and transcriptional regulatory elements are known to those of skill in the art and others may be identified or synthesized by methods known to those of skill in the art. Examples of reporter genes include, but are not limited to CAT (chloramphenicol acetyl transferase) (Alton and Vapnek (1979), Nature 282: 864-869) luciferase, and other enzyme detection systems, such as beta-galactosidase; firefly luciferase (deWet et al. (1987), Mol. Cell. Biol. 7:725-737); bacterial luciferase (Engebrecht and Silverman (1984), PNAS 1: 4154-4158; Baldwin et al. (1984), Biochemistry 23: 3663-3667); alkaline phosphatase (Toh et al. (1989) Eur. J. Biochem. 182: 231-238, Hall et al. (1983) J. Mol. Appl. Gen. 2: 101), human placental secreted alkaline phosphatase (Cullen and Malim (1992) Methods in Enzymol. 216:362-368); β-lactamase or GST.

Transcriptional control elements for use in the reporter gene constructs, or for modifying the genomic locus of an indicator gene include, but are not limited to, promoters, enhancers, and repressor and activator binding sites. Suitable transcriptional regulatory elements may be derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (see, Sheng et al. (1990) Neuron 4: 477-485), such as c-fos. Immediate early genes are genes that are rapidly induced upon binding of a ligand to a cell surface protein. The transcriptional control elements that are preferred for use in the gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

In still other embodiments, the detection step is provided in the form of a cell-free system, e.g., a cell-lysate or purified or semi-purified protein or nucleic acid preparation. The samples obtained from the recombinant host cells can be tested for such activities as inhibiting or potentiating such pairwise complexes (the "target complex") as involving protein-protein interactions, protein-nucleic acid interactions, protein-ligand interactions, nucleic acid-nucleic acid interactions, and the like. The assay can detect the gain or loss of the target complexes, e.g. by endogenous or heterologous activities associated with one or both molecules of the complex.

Assays that are performed in cell-free systems, such as may be derived with purified or semi-purified proteins, are often preferred as "primary" screens in that they can be generated to permit rapid development and relatively easy detection of an alteration in a molecular target when contacted with a test sample. Moreover, the effects of cellular toxicity and/or bioavailability of the test sample can be generally ignored in the in vitro system, the assay instead being focused primarily on the effect of the sample on the molecular target as may be manifest in an alteration of binding affinity with other molecules or changes in enzymatic properties (if applicable) of the molecular target. Detection and quantification of the pairwise complexes provides a means for determining the test samples efficacy at inhibiting (or potentiating) formation of complexes. The efficacy of the compound can be assessed by generating dose response curves from data obtained using various concentrations of the test sample. Moreover, a control assay can also be performed to provide a baseline for comparison. For instance, in the control assay conditioned media from untransformed host cells can be added.

The amount of target complex may be detected by a variety of techniques. For instance, modulation in the formation of complexes can be quantitated using, for example, detectably labeled proteins or the like (e.g., radiolabeled, fluorescently labeled, or enzymatically labeled), by immunoassay, or by chromatographic detection.

In still other embodiments, a purified or semi-purified enzyme can be used to assay the test samples. The ability of a test sample to inhibit or potentiate the activity of the enzyme can be conveniently detected by following the rate of conversion of a substrate for the enzyme.

In yet other embodiments, the detection step can be designed to detect a phenotypic change in the host cell which is induced by products of the expression of the heterologous genomic sequences. Many of the above-mentioned cell-based assay formats can also be used in the host cell, e.g., in an autocrine-like fashion.

In addition to providing a basis for isolating biologically-active molecules produced by the recombinant host cells, the detection step can also be used to identify genomic clones which include genes encoding biosynthetic pathways of interest. Moreover, by iterative and/or combinatorial subcloning methods relying on such detection steps, the individual genes which confer the detected pathway can be cloned from the larger genomic fragment.

The subject screening methods can be carried in a differential format, e.g. comparing the efficacy of a test sample in a detection assay derived with human components with those derived from, e.g., fungal or bacterial components. Thus, selectivity as a bacteriocide or fungicide can be a criterion in the selection protocol.

The host strain need not produce high levels of the novel compounds for the method to be successful. Expression of the genes may not be optimal, global regulatory factors may not be present, or metabolite pools may not support maximum production of the product. The ability to detect the metabolite will often not require maximal levels of production, particularly when the bioassay is sensitive to small amounts of natural products. Thus initial submaximal production of compounds need not be a limitation to the success of the subject method.

Finally, as indicated above, the test sample can be derived from, for example, conditioned media or cell lysates. With regard to the latter, it is anticipated that in certain instances there may be heterologously-expressed compounds that may not be properly exported from the host cell. There are a variety of techniques available in the art for lysing cells. A preferred approach is another aspect of the present invention, namely, the use of a host cell-specific lysis agent. For instance phage (e.g., P1, λ, φ80) can be used to selectively lyse *E. coli*. Similarly, cyanophages can be used to selectively lyse cyanobacteria, such as *Synechococcus* and *Prochlorococcus*. Addition of such phage to grown cultures of host cells can maximize access to the heterologous products of new biosynthetic pathways in the cell. Moreover, such agents do not interfere with the growth of a tester organism, e.g., a human cell, that may be co-cultured with the host cell library.

Metabolic Optimization

As part of the optimization process, the invention also provides steps to eliminate undesirable side reactions, if any, that may consume carbon and energy but do not produce useful products (such as hydrocarbons, wax esters, surfactants and other hydrocarbon products). These steps may be helpful in that they can help to improve yields of the desired products.

A combination of different approaches may be used. Such approaches include, for example, metabolomics (which may be used to identify undesirable products and metabolic intermediates that accumulate inside the cell), metabolic modeling and isotopic labeling (for determining the flux through metabolic reactions contributing to hydrocarbon production), and conventional genetic techniques (for eliminating or substantially disabling unwanted metabolic reactions). For example, metabolic modeling provides a means to quantify fluxes through the cell's metabolic pathways and determine the effect of elimination of key metabolic steps. In addition, metabolomics and metabolic modeling enable better understanding of the effect of eliminating key metabolic steps on production of desired products.

To predict how a particular manipulation of metabolism affects cellular metabolism and synthesis of the desired product, a theoretical framework was developed to describe the molar fluxes through all of the known metabolic pathways of the cell. Several important aspects of this theoretical framework include: (i) a relatively complete database of known pathways, (ii) incorporation of the growth-rate dependence of cell composition and energy requirements, (iii) experimental measurements of the amino acid composition of proteins and the fatty acid composition of membranes at different growth rates and dilution rates and (iv) experimental measurements of side reactions which are known to occur as a result of metabolism manipulation. These new developments allow significantly more accurate prediction of fluxes in key metabolic pathways and regulation of enzyme activity. (Keasling, J. D. et al., "New tools for metabolic engineering of *Escherichia coli*," In Metabolic Engineering, Publisher Marcel Dekker, New York, Nym 1999; Keasling, J. D, "Gene-expression tools for the metabolic engineering of bacteria," *Trends in Biotechnology*, 17, 452-460, 1999; Martin, V. J. J., et al., "Redesigning cells for production of complex organic molecules," *ASM News* 68, 336-343 2002; Henry, C. S., et al., "Genome-Scale Thermodynamic Analysis of *Escherichia coli* Metabolism," *Biophys. J.*, 90, 1453-1461, 2006.)

Such types of models have been applied, for example, to analyze metabolic fluxes in organisms responsible for enhanced biological phosphorus removal in wastewater treatment reactors and in filamentous fungi producing polyketides. See, for example, Pramanik, et al., "A stoichiometric model of *Escherichia coli* metabolism: incorporation of growth-rate dependent biomass composition and mechanistic energy requirements." *Biotechnol. Bioeng.* 56, 398-421, 1997; Pramanik, et al., "Effect of carbon source and growth rate on biomass composition and metabolic flux predictions of a stoichiometric model." *Biotechnol. Bioeng.* 60, 230-238, 1998; Pramanik et al., "A flux-based stoichiometric model of enhanced biological phosphorus removal metabolism." *Wat. Sci. Tech.* 37, 609-613, 1998; Pramanik et al., "Development and validation of a flux-based stoichiometric model for enhanced biological phosphorus removal metabolism." *Water Res.* 33, 462-476, 1998.

Products

The HyperPhotosynthetic organisms in the present invention may be engineered to yield product categories, including but not limited to, biological sugars, hydrocarbon products, solid forms, and pharmaceuticals.

Biological sugars include but are not limited to glucose, starch, cellulose, hemicellulose, glycogen, xylose, dextrose, fructose, lactose, fructose, galactose, uronic acid, maltose, and polyketides. In preferred embodiments, the biological sugar may be glycogen, starch, or cellulose.

Cellulose is the most abundant form of living terrestrial biomass (Crawford, R. L. 1981. Lignin biodegradation and transformation, John Wiley and Sons, New York.). Cellulose, especially cotton linters, is used in the manufacture of nitrocellulose. Cellulose is also the major constituent of paper. Cellulose monomers (beta-glucose) are linked together through 1,4 glycosidic bonds. Cellulose is a straight chain (no coiling occurs). In microfibrils, the multiple hydroxide groups hydrogen-bond with each other, holding the chains firmly together and contributing to their high tensile strength. Given a cellulose material, the portion that does not dissolve in a 17.5% solution of sodium hydroxide at 20° C. is Alpha cellulose, which is true cellulose; the portion that dissolves and then precipitates upon acidification is Beta cellulose, and the proportion that dissolves but does not precipitate is Gamma cellulose. Hemicellulose is a class of plant cell-wall polysaccharide that can be any of several heteropolymers. These include xylane, xyloglucan, arabinoxylan, arabinogalactan, glucuronoxylan, glucomannan, and galactomannan. This class of polysaccharides is found in almost all cell walls along with cellulose. Hemicellulose is lower in weight than cellulose, and cannot be extracted by hot water or chelating agents, but can be extracted by aqueous alkali. Polymeric chains bind pectin and cellulose, forming a network of cross-linked fibers.

There are essentially three types of hydrocarbon products: (1) aromatic hydrocarbon products, which have at least one aromatic ring; (2) saturated hydrocarbon products, which lack double, triple or aromatic bonds; and (3) unsaturated hydrocarbon products, which have one or more double or triple bonds between carbon atoms. A "hydrocarbon product" may be further defined as a chemical compound that consists of C, H, and optionally O, with a carbon backbone and atoms of hydrogen and oxygen, attached to it. Oxygen may be singly or double bonded to the backbone and may be bound by hydrogen. In the case of ethers and esters, oxygen may be incorporated into the backbone, and linked by two single bonds, to carbon chains. A single carbon atom may be attached to one or more oxygen atoms. Hydrocarbon products may also include the above compounds attached to biological agents including proteins, coenzyme A and acetyl coenzyme A. Hydrocarbon products include, but are not limited to, hydrocarbons, alcohols, aldehydes, carboxylic acids, ethers, esters, carotenoids, and ketones.

Hydrocarbon products also include alkanes, alkenes, alkynes, dienes, isoprenes, alcohols, aldehydes, carboxylic acids, surfactants, wax esters, polymeric chemicals [polyphthalate carbonate (PPC), polyester carbonate (PEC), polyethylene, polypropylene, polystyrene, polyhydroxyalkanoates (PHAs), poly-beta-hydroxybutryate (PHB), polylactide (PLA), and polycaprolactone (PCL)], monomeric chemicals [propylene glycol, ethylene glycol, and 1,3-propanediol, ethylene, acetic acid, butyric acid, 3-hydroxypropanoic acid (3-HPA), acrylic acid, and malonic acid], and combinations thereof. In some preferred embodiments, the hydrocarbon products are alkanes, alcohols, surfactants, wax esters and combinations thereof. Other hydrocarbon products include fatty acids, acetyl-CoA bound hydrocarbons, acetyl-CoA bound carbohydrates, and polyketide intermediates.

Recombinant organisms can be engineered to produce hydrocarbon products and intermediates over a large range of sizes. Specific alkanes that can be produced include, for example, ethane, propane, butane, pentane, hexane, heptane, octane, nonane, decane, undecane, dodecane, tridecane, tetradecane, pentadecane, hexadecane, heptadecane, and octadecane. In preferred embodiments, the hydrocarbon products are octane, decane, dodecane, tetradecane, and hexadecane. Hydrocarbon precursors such as alcohols that can be produced include, for example, ethanol, propanol, butanol, pentanol, hexanol, heptanol, octanol, nonanol, decanol, undecanol, dodecanol, tridecanol, tetradecanol, pentadecanol, hexadecanol, heptadecanol, and octadecanol. In more preferred embodiments, the alcohol is selected from ethanol, propanol, butanol, pentanol, hexanol, heptanol, octanol, nonanol, and decanol.

Surfactants are used in a variety of products, including detergents and cleaners, and are also used as auxiliaries for textiles, leather and paper, in chemical processes, in cosmetics and pharmaceuticals, in the food industry and in agriculture. In addition, they may be used to aid in the extraction and isolation of crude oils which are found hard to access environments or as water emulsions. There are four types of surfactants characterized by varying uses. Anionic surfactants have detergent-like activity and are generally used for cleaning applications. Cationic surfactants contain long chain hydrocarbons and are often used to treat proteins and synthetic polymers or are components of fabric softeners and hair conditioners. Amphoteric surfactants also contain long chain hydrocarbons and are typically used in shampoos. Non-ionic surfactants are generally used in cleaning products.

Hydrocarbons can additionally be produced as biofuels. A biofuel is any fuel that derives from a biological source—recently living organisms or their metabolic byproducts, such as manure from cows. A biofuel may be further defined as a fuel derived from a metabolic product of a living organism.

Preferred biofuels include, but are not limited to, biodiesel, biocrude, ethanol, "renewable petroleum," butanol, and propane.

Solid forms of carbon including, for example, coal, graphite, graphene, cement, carbon nanotubes, carbon black, diamonds, and pearls. Pure carbon solids such as coal and diamond are the preferred solid forms.

Pharmaceuticals can be produced including, for example, isoprenoid-based taxol and artemisinin, or oseltamivir.

EXAMPLES

Plasmid Constructions

Construction of pJB5 Base Plasmid

The pJB5 base plasmid was designed as an empty expression vector for recombination into Synechococcus sp. PCC 7002. Two regions of homology, the Upstream Homology Region (UHR) and the Downstream Homology Region (DHR) were designed to flank the cloned gene(s) of interest. These 500 bp regions of homology correspond to positions 3301-3800 and 3801-4300 on the natural plasmid pAQ1 (Genbank Accession NC_005025) for UHR and DHR respectively. The aadA promoter, gene sequence, and terminator were designed to confer spectinomycin and streptomycin resistance to the integrated construct. For expression, pJB5 was designed with the aph2 kanamycin resistance cassette promoter and ribosome binding site (RBS). Downstream of this promoter and RBS, we designed and inserted the restriction endonuclease recognition site for NdeI and EcoRI, as well as the sites for XhoI, BamHI, SpeI and PacI. Following the EcoRI site, the natural terminator from the alcohol dehydrogenase gene from Zymomonas mobilis (adhII) terminator was included. Convenient XbaI restriction sites flank the UHR and the DHR allowing cleavage of the DNA intended for recombination from the rest of the vector. pJB5, pJB6 and pJB7 were constructed by DNA2.0 (Menlo Park, Calif.).

Construction of pJB161 Base Plasmid

The pJB161 base plasmid was designed to complement the pJB5 base plasmid, but with different integration sites and resistance markers to allow for integration of two genes simultaneously into Synechococcus sp. PCC 7002. The UHR and the DHR from pJB5 were replaced with regions flanking the lactate dehydrogenase gene of Synechococcus sp. PCC 7002. The new ldh-UHR and ldh-DHR were amplified by PCR and correspond to positions 185990-77 and 184333-184913 on the natural plasmid pAQ7 (Genbank Accession NC_0104774) for lac-UHR and lac-DHR respectively. The primers used for the PCR were as follows: Forward Primer for lac-UHR—ttgctacctgcagggccaccacagccaaattcatcgtt (SEQ ID NO: 1), Downstream Primer for lac-UHR—ggttgtgcggccg-cagtattggctgtgatgttgg (SEQ ID NO: 2); Upstream Primer for lac-DHR—cgataaggcgcgccgaaactgcgccaagaatagc (SEQ ID NO: 3), Downstream Primer for lac-DHR—gtgtatggccggc-catcgcctttatggtgctttatgtg (SEQ ID NO: 4). The Upstream Primer for lac-UHR added a SbfI restriction endonuclease site, the Downstream Primer for lac-UHR added a NotI restriction site, the Upstream Primer for lac-DHR added an AscI restriction site, and the Downstream Primer for lac-DHR added an FseI restriction site. The homology regions were amplified from Synechococcus sp. PCC 7002 genomic DNA using the high fidelity Phusion DNA Polymerase Master Mix (New England Biolabs, Beverly, Mass.). The amplified ldh-DHR region and the pJB5 plasmid were digested individually with FseI and AscI (New England Biolabs) restriction endonucleases using well known laboratory techniques. The resulting DNA fragments were gel isolated on a 1% TAE agarose gel, purified using a Gel Isolation Kit (Qiagen) and ligated with the Quick Ligation Kit (New England Biolabs) with no deviation from the published techniques. The ligated product was transformed into EPI400 (EpiCentre®) chemically competent cells using standard techniques, and confirmed by PCR. The resulting plasmid was subjected to another round of cloning to integrate the ldh-UHR region. The amplified ldh-UHR region and the newly constructed plasmid were digested individually with SbfI and NotI (New England Biolabs) restriction endonucleases using well known laboratory techniques. Both digestions were gel isolated on a 1% TAE agarose gel, purified using a Gel Isolation Kit (Qiagen) and ligated with the Quick Ligation Kit (New England Biolabs) with no deviation from the published techniques. The ligated product was transformed into EPI400 chemically competent cells using standard techniques (EpiCenter), and confirmed by PCR. The resulting plasmid, pJB165, was confirmed by PCR and restriction digestion.

Finally, to change the resistance marker for the integrated construct, a kanamycin resistance cassette, from the cloning vector pMAKK76 (Accession Number: U08460) was designed with restriction sites for PacI and AscI flanking the 5' and 3' end of the gene respectively. The cassette was constructed by DNA2.0 (Menlo Park, Calif.). This cassette, along with pJB165 were both individually digested with PacI and AscI (New England Biolabs) restriction endonucleases using well known laboratory techniques. Both digestions were gel isolated on a 1% TAE agarose gel, purified using a Gel Isolation Kit (Qiagen) and ligated with the Quick Ligation Kit (New England Biolabs) with no deviation from the published techniques. The ligated product was transformed into EPI400 chemically competent cells using standard techniques (EpiCentre). The resulting plasmid, pJB161, was confirmed by PCR and by resistance of transformed colonies to the antibiotic kanamycin.

Construction of pJB5-PdcAdhII and JCC136

The pyruvate decarboxylase (pdc) and alcohol dehydrogenase (adhII) genes were cloned into the pJB5 plasmid with the following procedure. The pdc-adhII genes from Zymomonas mobilis (Genbank: DD161475, M15394) were designed with an NdeI site replacing the start of the pdc coding region. Following the pdc gene, we designed two restriction endonuclease sites (XhoI and BamHI). Next, the adhII sequence was designed in whole subsequent to the restriction sites, and finally, the natural adhII terminator was included as well, downstream of an inserted EcoRI site. This construct was constructed by DNA2.0 (Menlo Park, Calif.) and was inserted by restriction digest with NdeI and EcoRI (New England Biolabs; Ipswitch, Mass.) on both pJB5 and the insert followed by ligation with a Quick Ligation Kit (New England Biolabs; Ipswitch, Mass.). The ligated construct was transformed into The NEB 5-alpha F'Iq Competent E. coli (High Efficiency) (New England Biolabs: Ipswitch, Mass.).

Transformation of pJB5-PdcAdhII into Synechococcus sp. PCC 7002 Using Standard Procedures.

Briefly, Synechococcus sp. PCC 7002 was grown for 48 h from colonies in an incubated shaker flask at 30° C. with 1% $CO_2$ to an $OD_{730}$ of 1.0 in $A^+$ medium described in Frigaard N U et al. (2004) "Gene inactivation in the cyanobacterium Synechococcus sp. PCC 7002 and the green sulfur bacterium Chlorobium tepidum using in vitro-made DNA constructs and natural transformation" Methods Mol Biol 274:325-340. Five hundred µL of culture was added to a test-tube with 30

μL of 1-5 μg of DNA prepped from a Qiagen Qiaprep Spin Miniprep Kit (Valencia, Calif.) for each construct. Cells were incubated bubbling in 1% $CO_2$ at approximately 1 bubble every 2 seconds for 4 hours. 200 μL of cells were plated on $A^+$ medium plates with 1.5% Bacto-agar and grown at 30° C. for two days in low light. Spectinomycin was underlayed to give a final concentration of 10 μg/mL. Resistant colonies were visible in 7-10 days. Colonies were screened by PCR. The resulting strain was named JCC136.

Construction of pJB263 Base Plasmid

The pJB263 base plasmid was constructed to be similar to pJB5, but for integration and replacement of the glgA gene (Accession Number: NP_441947) in *Synechocystis* sp. PCC 6803. The glgA-UHR and glgA-DHR were designed to 750 bp upstream and downstream of the glgA gene in *Synechocystis* sp. PCC 6803, which corresponds to (−) strands of 2266647 to 22667396 and 2264463 to 2265212 respectively on the chromosome (Accession Number: NC_000911). The glgA-UHR and glgA-DHR were designed with flanking SbfI and NotI restriction endonuclease sites, as well as PacI and AscI restriction endonuclease sites, with a sequence spacer to ease later digest in between. This construct was constructed by DNA2.0 (Menlo Park, Calif.). This cassette, along with pJB5-PdcAdhII, was both individually digested with NotI and AscI (New England Biolabs) restriction endonucleases using well known laboratory techniques. Both digestions were gel isolated on a 1% TAE agarose gel, purified using a Gel Isolation Kit (Qiagen) and ligated with the Quick Ligation Kit (New England Biolabs) with no deviation from the published techniques. The ligated product was transformed into EPI400 chemically competent cells using standard techniques (EpiCentre). The resulting plasmid, pJB263, was confirmed by PCR and by resistance of transformed colonies to the antibiotic spectinomycin.

Examples

The examples provided herein illustrate the invention in more detail. These examples are provided to enable those skilled artisans to help understand and practice various aspects of the invention and therefore should not be construed as limiting. Various modifications and extensions of the invention in addition to those described herein will become apparent to those skilled artisans and therefore such modifications and extensions fall within the scope of invention.

Example 1

Improved Light Capture

Photosynthetic organisms have evolved elaborate methods to efficiently capture light, which is often times limiting in their natural habitats. Eukaryotic photoautotrophic organisms encode a superfamily of chlorophyll and carotenoid-binding proteins known as the light-harvesting complexes (LHCs), which capture and transfer light energy to the photosynthetic reaction centers [Green B R and Dumford D G. "The chlorophyll-carotenoid proteins of oxygenic photosynthesis." Ann Rev Plant Physiol Plant Mol Biol (1996). 47:685-714]. Chlorophyll molecules are specifically arranged in so called "antenna" structures; the number of chlorophyll molecules per reaction center can vary considerably encompassing upwards of 350 chlorophyll a and chlorophyll b molecules per reaction center for photosystem II (PSII) and 300 chlorophyll a molecules for photosystem I (PSI). Antennas provide a means to increase light absorption spectra without having to build an entirely new protein-based reaction center and accompanying electron transport system. Large antenna provides survival advantages to organisms in the wild; however, under conditions of high light intensity, they absorb excess photons which must be wastefully dissipated as fluorescence or heat. Failure to safely dissipate a singlet-state excited chlorophyll molecule can result in formation of singlet oxygen, which is an extremely damaging reactive oxygen species [Muller P, Li X, Niyogi K K. "Non-photochemical quenching. A response to excess light energy." Plant Physiology (2001). 125:1558-66].

Organisms naturally increase or decrease their chlorophyll antenna size as an adaptive response to changing light conditions [Falkowski P G and Owens T G. "Light-shade adaptation." Plant Physiol (1980). 66:592-595; Ballottari M, Dall'Osto L, Morosinotto T, and Bassi R. "Contrasting behavior of higher plant photosystem I and II antenna systems during acclimation." J Biol Chem (2007). 282(12):8947-58].

Recently, it has been demonstrated that the normally dynamic antenna size of microalgae can be permanently truncated genetically via downregulation of tla1 [Polle J, Kanakagiri S, and Melis A. "tla1, a DNA insertional transformant of the green alga *Chlamydomonas reinhardtii* with a truncated light-harvesting chlorophyll antenna size." Planta (2003). 217:49-59; Tetali S D, Mitra M, and Melis A. "Development of the light-harvesting chlorophyll antenna in the green alga *Chlamydomonas reinhardtii* is regulated by the novel Tla1 gene." Planta (2007). 225:813-829] or the entire family of LHC proteins [Mussgnug J H, Thomas-Hall S, Rupprecht J, Foo A, Klassen V, McDowall A, Schenk P M, Kruse O, and Hankamer B. "Engineering photosynthetic light capture: impacts on improved solar energy to biomass conversion." (2007). 5(6):802-14]. Strains possessing smaller antenna exhibit reduced cell shading and higher productivities specifically under high light fluxes.

Chlorosomes, the light-harvesting antenna of green sulfur and green non-sulfur phototrophic bacteria, are specialized lipoprotein compartments typically comprising bacteriochlorophyll (BChl) c, BChl a, carotenoids, and quinones [Frigaard N U, Li H, Milks K J, and Bryant D A. "Nine mutants of *Chlorobium tepidum* each unable to synthesize a different chlorosome protein still assemble functional chlorosomes. J Bacteriol (2004). 186(3):636-53]. In the wild, chlorosomes provide green bacteria significant survival advantages, as they enable growth under extremely low light conditions. The antenna structure can be eliminated by inactivating the BChl c synthase (bchK) [Friggard N U, Voigt G D, and Bryant D A. "*Chlorobium tepidum* mutant lacking bacteriochlorophyll c made by inactivation of the bchK gene, encoding bacteriochlorophyll c synthase." J Bacteriol (2002). 184(12):3368-76]. Such mutants replicate about 7-fold slower than their wild-type counterparts under low-light conditions, but are only partially impaired (~2.3-fold) under higher light intensities.

Phycobilisomes, the light harvesting antenna of cyanobacteria and red algae, are primarily comprised of the phycobiliproteins phycoerythrin, phycocyanin, and allophycocyanin [Grossman A R, Schaefer M R, Chiang G G, and Collier J L. "The phycobilisome, a light-harvesting complex responsive to environmental conditions." Microbiol Rev (1993). 57(3): 725-49]. Like the light harvesting antenna of plants, algae, and green bacteria, the phycobilisomes are entirely dispensable in cyanobacteria [Ughy B and Ajlani G. "Phycobilisome rod mutants in *Synechocystis* sp. Strain PCC 6803."Microbiology (2004). 150:4147-4156; Ajlani G and Vemotte C. Construction and characterization of phycobiliprotein-less mutant of *Synechocystis* sp. PCC 6803." Plant Mol Biol (1998). 37:577-580; Anderson A K and Toole C M. "A model for early events in the assembly pathway of cyanobacterial phycobilisomes." Mol. Microbiol. (1998). 30(3):467-74].

While photoautotrophic organisms invariably utilize photosynthetic reaction centers to convert photonic energy into chemical energy (in the form of ATP, via proton motive force (PMF)-driven ATP synthase) and reducing power (NADPH), no known photoautotrophic organisms employ light-activated proton translocation systems as exemplified by archaeal rhodopsin-like proteins (bacteriorhodopsin) [Oesterhelt D and Stoeckenius W. "Rhodopsin-like protein from the purple membrane of *Halobacterium halobium*." Nature New Biol (1971). 233(39):149-52]. Nevertheless, related sequences have definitively been shown to mediate light-driven energy generation (photoheterotrophy) in bacteria [Beja O, Aravind L, Koonin E V, Suzuki M, Hadd A, Nguyen L P, Jovanovich S B, Gates C M, Feldman R A, Spudich J L, Spudich E N, and DeLong E F. "Bacterial rhodopsin: evidence for a new type of phototrophy in the sea." Science (2000). 289:1902-6; Beja O, Spudich E N, Spudich J L, Leclerc M, DeLong E F. "Proterhodopsin phototrophy in the ocean." Nature (2001). 411:786-9; de la Torre J R, Christianson L M, Beja O, Suzuki M T, Karl D M, Heidelberg J, and DeLong E F. "Proteorhodopsin genes are distributed among divergent marine bacterial taxa." Proc Natl Acad. Sci. (2003). 100(22):12830-5].

The present invention teaches that exogenous expression of one or more forms of light-powered proton pumps in a photoautotroph increases organism efficiency by providing a parallel means to convert photonic energy into PMF, which can be used to power active transport of molecules across membranes or generate ATP through an endogenous or exogenous ATP synthase. It has been estimated that transport consumes between 15-25% of all energy during cell growth [Stouthamer A H. "A theoretical study on the amount of ATP required for synthesis of microbial cell material." Antonie Van Leeuwenhoek (1973). 39(3):545-65; Carruthers A. "Mechanisms for the facilitated diffusion of substrates across cell membranes." Biochemistry (1991). 30(16):3898-906]. Expression of light-powered proton pumps thus provides photoautotrophic organisms with up to a 15-25% gain in energetic efficiency, which is manifested by an improvement in doubling-time, $CO_2$-fixation rates, and/or carbon-based product formation.

The proteorhodopsin (PR) gene is preferentially expressed in organisms. An exemplary PR sequence is locus ABL60988 described in Martinerz A, Bradley A S, Walbauer J R, Summons R E, DeLong E F. PNAS (2007). "Proteorhodopsin photosystem gene expression enables photophosphorylation in a heterologous host." 104(13):5590-5595.

In addition, or as an alternative, a bacteriorhodopsin gene is expressed [Oesterhelt D, Stoeckenius W. Nature (1971) "Rhodopsin-like protein from the purple membrane of *Halobacterium halobium.*" 233:149-152]. An exemplary bacteriorhodopsin sequence is the NP_280292 locus described in Ng W V et al. PNAS (2000). "Genome sequence of Halobacterium species NRC-1." 97(22):12176-22181. Bacteriorhodopsin has previously been functionally expressed in yeast mitochondria [Hoffmann A, Hildebrandt V, Heberle J, Buldt G. "Photoactive mitochondria: In vivo transfer of a light-driven proton pump into the inner mitochondrial membrane of *Schizosaccharomyces pombe*." Proc. Natl. Acad. Sci. (1994). 91: 9637-71].

Similarly, deltarhodopsin is expressed in addition to or as an alternative [Ihara K et al. J Mol Biol (1999). "Evolution of the archael rhodopsins: evolution rate changes by gene duplication and functional differentiation." 285:163-174; Kamo N, Hashiba T, Kikukawa T, Araiso T, Ihara K, Nara T. Biochem Biophys Res Commun (2006). "A light-driven proton pump from *Haloterrigena turkmenica*: functional expression in *Escherichia coli* membrane and coupling with a $H^+$ co-transporter." 342(2): 285-90). An exemplary deltarhodopsin sequence is the AB009620 locus of *Haloterrigena* sp. Arg-4 described in Ihara K et al. J Mol Biol (1999). "Evolution of the archael rhodopsins: evolution rate changes by gene duplication and functional differentiation." 285:163-174.

Similarly, the *Leptosphaeria maculans* opsin protein is expressed as an addition to or as an alternative to other proton pumps. An exemplary eukaryotic light-activated proton pump is opsin, accession AAG01180 from *Leptosphaeria maculans*, described in Waschuk S A, Benzerra A G, Shi L, and Brown L S. PNAS (2005). "*Leptosphaeria* rhodopsin: Bacteriorhodopsin-like proton pump from a eukaryote." 102 (19):6879-83].

Finally a xanthorhodopsin proton pump with a carotenoid antenna is expressed in addition to or as an alternative to other proton pumps (Balashov S P, Imasheva E S, Boichenko V A, Anton J, Wang J M, Lanyi J K. Science (2005) "Xanthorhodopsin: A proton pump with a light harvesting cartenoid antenna." 309(5743): 2061-2064). An exemplary xanthorhodopsin sequence is locus ABC44767 from *Salinibacter ruber* DSM 13855 described in Mongodin E F et al. PNAS (2005). "The genome of *Salinibacter ruber*: Convergence and gene exchange among hyperhalophilic bacteria and archaea." 102(50):18147-18152.

The pumps are used alone or in combination, optimized to the specific cell. The pumps can be directed to be incorporated into one or more than one membrane locations, for example the cytoplasmic, outer, mitochondrial, and/or chloroplast membranes. Xanthorhodopsin and proteorhodopsin co-expression represents an optimal combination.

In addition to the expression of one or more proton pumps described above, a retinal biosynthesis pathway is expressed. When PR and the retinal biosynthetic operon are functionally expressed in *E. coli*, the pump is able to restore proton motive force to azide-treated *E. coli* populations [Walter J M, Greenfield D, Bustamante C, Liphardt J. PNAS (2007). "Light-powering *Escherichia coli* with proteorhodopsin." 104(7): 2408-2412]. A six gene retinal biosynthesis operon, Accession number EF100190 is known (Martinerz A, Bradley A S, Walbauer J R, Summons R E, DeLong E F. PNAS (2007). "Proteorhodopsin photosystem gene expression enables photophosphorylation in a heterologous host." 104 (13):5590-5595) and encodes amino acid sequences Isopentenyl-diphosphate delta-isomerase (Idi), locus ABL60982; 15,15'-beta-carotene dioxygenase (Blh), locus ABL60983; Lycopene cyclase (CrtY), locus ABL60984; Phytoene synthase (CrtB), EC 2.5.1.32, locus ABL60985; Phytoene dehydrogenase (CrtI), locus ABL60986; and Geranylgeranyl pyrophosphate synthetase (CrtE), locus ABL60987.

The above 6 enzymes enable biosynthesis of retinal, which is the essential chromophore common to all rhodopsin-related proton pumps. In certain embodiments, additional spectral absorption is provided by carotenoids, as exemplified by the xanthorhodopsin pump and the C-40 salinixanthin antenna. In these embodiments, a beta-carotene ketolase (CrtO) is expressed, such as the crtO gene of the SRU_1502 locus in *Salinibacter ruber*, described in Mongodin E F et al (2005). Other crtO genes include those from *Rhodococcus erythropolis* (AY705709) and *Deinococcus radiodurans* R1 (NP_293819).

In certain embodiments, an endogenous or exogenous ATP synthase (EC 3.6.3.14) is overexpressed to enable maximal conversion of PMF into ATP. An exemplary ATP synthase is the $F_1$-$F_0$ ATP synthase from *Escherichia coli*. The membrane-bound $F_0$ subunit is comprised of amino acid sequences set forth in F0 sector of membrane-bound ATP synthase, subunit a (AtpB), locus NP_418194; F0 sector of membrane-bound ATP synthase, subunit c (AtpE), locus NP_418193; and F0 sector of membrane-bound ATP synthase, subunit b (AtpF), locus NP_418192. The catalytic $F_1$ subunit is comprised of amino acid sequences set forth in F1 sector of membrane-bound ATP synthase, alpha subunit (AtpA), locus NP_418190; F1 sector of membrane-bound ATP synthase, epsilon subunit (AtpC), locus NP_418187; F1 sector of membrane-bound ATP synthase, beta subunit (AtpD), locus NP_418188; F1 sector of membrane-bound ATP synthase, gamma subunit (AtpG), locus NP_418189; and F1 sector of membrane-bound ATP synthase, delta subunit, (AtpH) locus NP_418191.

In preferred embodiments, light-powered proton pumps are expressed in the context of one or more cellular membranes within an organism previously adapted, evolved, or engineered to contain smaller light harvesting antenna than the wild-type organism prior to adaptation, evolution, or engineering. Such organisms are uniquely efficient at converting light energy into cellular energy, biomass, and products, particularly when propagated under high light fluxes.

Expression of SAR86 Gene Encoding Proteorhodopsin for the Light Capture Module

The SAR86 proteorhodopsin gene (Beja, et al. (*Science* (2000) vol. 289: 1902-1906; Genbank: AF279106) as used herein was obtained from a plasmid previously constructed and provided by Jessica Walters and Jan Liphardt (University of California, Berkeley). The Walters-Liphardt host plasmid is a pBR322 plasmid derivative with a beta-lactamase cassette bearing the SAR86 proteorhodopsin gene. The proteorhodopsin gene was amplified from the Walters-Liphardt plasmid using PCR primers with the forward primer 5'-TATA-CATCATATGGGTAAATTATTACTGATATTAGGTAGTG-TTATTGC-3' (SEQ ID NO: 5) and the reverse primer 5'-GC-TACAATTGTTAAGCATTAGAAGATTCTT-TAACAGCAACATTCC-3' (SEQ ID NO: 6). PCR amplifications were performed with the high fidelity Phusion DNA Polymerase Master Mix (New England Biolabs, Beverly, Mass.). The forward primer adds an NdeI restriction recognition site, and the reverse primer adds a stop codon and an MfeI restriction recognition site.

Figure 10:
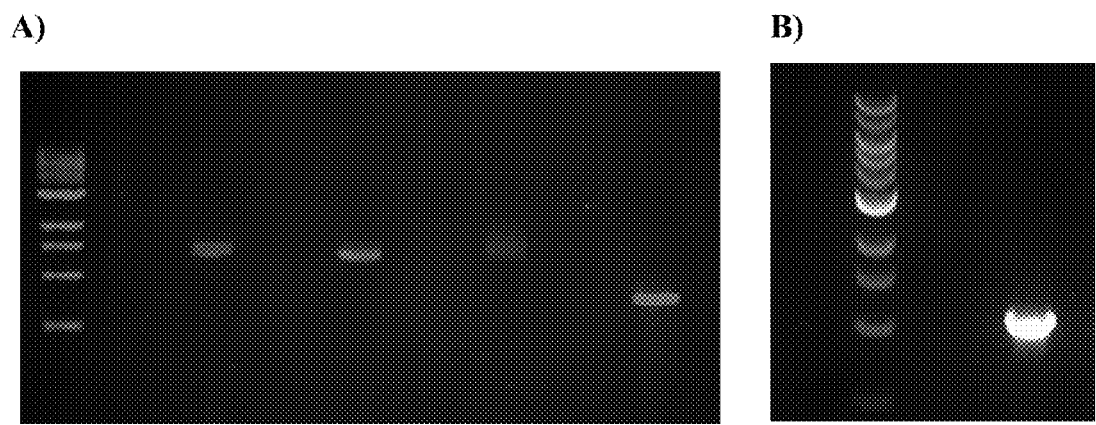

The amplified proteorhodpsin PCR gene product was cloned into the pJB5 expression vector ("pJB5-PR") by digesting the insert and vector individually with NdeI and MfeI (New England Biolabs) restriction endonucleases with well known laboratory techniques. Both digestions were gel isolated on 1% TAE agarose gel, purified using a Gel Isolation Kit (Qiagen) and ligated with the Quick Ligation Kit (New England Biolabs) with no deviation from the published techniques. The ligated product was transformed into EPI400 chemically competent cells using standard techniques (Epi-Center), and confirmed by PCR.

pJB5-PR plasmid stocks were purified using Qiagen miniprep kit for transformation into *Synechococcus* sp. PCC 7002. One to two micrograms of pJB5-PR plasmid was added to *Synechococcus* sp PCC 7002 cells grown to an optical density of 1 and incubated at 37 C for 4 hours using low intensity orbital shaking and low level light source. Cells were then plated onto $A^+$ solid media plates and placed in a lighted incubator (100-250 uE/m2/s, 37 C) for 1 day. Twenty-five micrograms/mL spectinomycin was underplayed on the plates and incubated until colonies grew (~5 days). Integration into target *Synechococcus* host cells is confirmed by PCR of whole cell genomic DNA by a "colony PCR" protocol. Briefly, ~1 mm colonies were resuspended in 50 µl deionized water, and 5 µl were used in 20 µl standard PCR reactions using Phusion DNA Polymerase Master Mix (New England Biolabs, Beverly, Mass.) with the addition of a 2 minute 98 C degree denaturation step at the very start of the standard PCR cycling conditions. The PCR showed correct bands for colonies, and the strain was named JCC1-SAR86 (FIG. 10, lane 5).

Example 2

Improving $CO_2$ Fixation

There are four known pathways that enable autotrophic carbon fixation: the 3-hydroxyproprionate (3-HPA) cycle (employed by *Chloroflexus aurantiacus* and *Crenarchaeota symbiosum*), the reductive TCA cycle (employed by *Chlorobium tepidum*), the reductive acetyl coenzyme A pathway (also known as Woods-Ljungdahl pathway; employed by chemolithoautotrophs such as *Clostridium thermoaceticum, Methanobacterium thermautotrophicum*, and *Dusulfobacterium autotrophicum*), and the reductive pentose phosphate cycle (also known as the Calvin cycle, employed by plants, algae, and all cyanobacteria). By definition, all photoautotrophic organisms possess the ability to fix inorganic $CO_2$ into complex, reduced organic carbon molecules, such as sugars.

The instant invention improves the rate and efficiency of $CO_2$ fixation by engineering functional improvements into the host's endogenous $CO_2$ fixation pathways, including overexpression of wild-type and/or variant enzymes. Alternately or in addition, functional improvements are engineered via supplementing the host's endogenous $CO_2$ fixation pathways with one or more exogenous $CO_2$ fixation enzymes or pathways.

The engineered organisms replicate more rapidly than their wild-type counterparts. Overexpression of two enzymes of the Calvin cycle in tobacco leaves has previously been shown to enhance growth compared to the wild-type plants [Tamoi M, Nagaoka M, Yabuta Y, and Shigeoka S. "Carbon metabolism in the Calvin cycle." Plant Biotechnology (2005). 22:355-360]. While not wishing to be bound by theory, improved endogenous and/or exogenous $CO_2$ fixation enzymes enables more rapid conversion of $CO_2$ into biological intermediates and carbon products, which appears to be a limiting facet governing the doubling time of photoautotrophic organisms.

Table 1 lists genes which are overexpressed to enhance carbon fixation rates and efficiencies, together with information on associated pathways, Enzyme Commission (EC) Numbers, exemplary gene names, source organism, GenBank accession numbers, and homologs from alternate sources. When the parental organism encodes a gene with the indicated enzymatic activity, it is nevertheless useful to overexpress these components to improve $CO_2$ fixation. In one embodiment, the native enzyme sequence is overexpressed. In preferred embodiments, it is useful to overexpress an exogenous gene, which allows for more explicit regulatory control in the bioprocess and a means to potentially mitigate the effects of central metabolism regulation, which is focused around the native genes explicitly.

I. Enzymes for a Functional 3-Hydroxypropionate Cycle

The following enzyme activities are expressed to establish a functional 3-hydroxypropionate cycle. This pathway is natively employed by *Chloroflexus aurantiacus* [Herter S, Farfsing J, Gad'On N, Rieder C, Eisenreich W, Bacher A, and Fuchs G. J Bacteriol (2001). "Autotrophic CO$_2$ fixation by *Chloroflexus aurantiacus*: study of glyoxylate formation and assimilation via the 3-hydroxypropionate cycle." 183(14): 4305-16].

Acetyl-CoA carboxylase (ACCase), (EC 6.4.1.2), generates malonyl-CoA, ADP, and Pi from Acetyl-CoA, CO$_2$, and ATP. An exemplary ACCase subunit alpha is accA from *E. coli*, locus AAA70370. An exemplary ACCase subunit beta is accD from *E. coli*, locus AAA23807. An exemplary biotin-carboxyl carrier protein is accB from *E. coli*, locus ECOA-COAC. An exemplary biotin carboxylase is accC from *E. coli*, locus AAA23748.

Malonyl-CoA reductase (also known as 3-hydroxypropionate dehydrogenase) (EC 1.1.1.59), generates 3-hydroxyproprionate, 2 NADP$^+$, and CoA from malonyl-CoA and 2 NADPH. An exemplary bifunctional enzyme with both alcohol and dehydrogenase activities is mcr from *Chloroflexus aurantiacus*, locus AY530019.

3-hydroxypriopionyl-CoA synthetase (also known as 3-hydroxypropionyl-CoA dehydratase, or acryloyl-CoA reductase) generates propionyl-CoA, AMP, PPi (inorganic pyrophosphate), H$_2$O, and NADP$^+$ from 3-hydroxypriopionate, ATP, CoA, and NADPH. An exemplary gene is propionyl-CoA synthase (pcs) from *Chloroflexus aurantiacus*, locus AF445079.

Propionyl-CoA carboxylase (EC 6.4.1.3) generates S-methylmalonyl-CoA, ADP, and Pi (inorganic phosphate) from Propionyl-CoA, ATP, and CO$_2$. An exemplary two subunit enzyme is propionyl-CoA carboxylase alpha subunit (pccA) from *Roseobacter denitrificans*, locus RD1__2032 and propionyl-CoA carboxylase beta subunit (pccB) from *Roseobacter denitrificans*, locus RD 1__2028.

Methylmalonyl-CoA epimerase (EC 5.1.99.1) generates R-methylmalonyl-CoA from S-methylmalonyl-CoA. An exemplary enzyme from *Rhodobacter sphaeroides* is locus CP000661.

Methylmalonyl-CoA mutase (EC 5.1.99.2) generates succinyl-CoA from R-methylmalonyl-CoA. The ylik protein (locus NC000913.2) is an example.

Succinyl-CoA:L-malate CoA transferase generates L-malyl-CoA and succinate from succinyl-CoA and malate. An exemplary two subunit enzyme is SmtA from *Chloroflexus aurantiacus*, locus DQ472736.1 and SmtB from *Chloroflexus aurantiacus*, locus DQ472737.1.

Fumarate reductase (EC 1.3.1.6) generates fumarate and NADH from succinate and NAD$^+$. An exemplary fumarate reductase is the *E. coli* frd operon (locus J01611). The frdA fumarate reductase flavoprotein subunit is known. It is important to note that some species may favor one direction over the other. Moreover, many of these proteins are present in organisms that express unidirectional and bidirectional versions. Examples are the frdB, fumarate reductase iron-sulfur subunit, and the g15 subunit the g13 subunit.

Fumarate hydratase (EC 4.2.1.2) generates malate from fumarate and water. *E. coli* encodes three distinct exemplary fumarate hydratases: the class I aerobic fumarate hydratase (fumA), locus CAA25204; the class I anaerobic fumarate hydratase (fumB), locus AAA23827; the class II fumarate hydratase (fumC), locus CAA27698.

L-malyl-CoA lyase (EC 4.2.1.2) generates acetyl-CoA and glyoxylate from L-malyl-CoA. An exemplary gene is mclA from *Roseobacter denitrificans*, locus NC__008209.1.

The above enzyme activities, listed in this section, confer the ability to synthesize an organic 2-carbon glyoxylate molecule from 2 molecules of CO$_2$. The stoichiometry of this reaction is 2 CO$_2$+3ATP+3NADPH→Glyoxylate+2ADP+2Pi+AMP+PPi+3NADP$^+$.

II. Enzymes for a Functional Reductive TCA Cycle

The following enzyme activities are expressed to establish a functional reductive TCA cycle. This pathway is natively employed by *Chlorobium tepidum*.

ATP-citrate lyase (EC. 2.3.3.8) generates acetyl-CoA, oxaloacetate, ADP, and Pi from citrate, ATP, and CoA. An exemplary ATP citrate lyase is the two subunit enzyme from *Chlorobium tepidum*, comprising ATP citrate lyase subunit 1, locus CY1089 and ATP citrate lyase subunit 2, locus CT1088.

*Hydrogenobacter thermophilus* employs an alternate pathway to generate oxaloacetate from citrate. In a first step, the 2 subunit citryl-CoA synthetase generates citryl-CoA from citrate, ATP, and CoA. The large subunit: ccsA, locus BAD17844; the small subunit: ccsB, locus BAD17846.

The *Hydrogenobacter thermophilus* citryl-CoA ligase (ccl), locus BAD17841, generates oxaloacetate and acetyl-CoA from citryl-CoA.

Malate dehydrogenase (EC 1.1.1.37) generates malate and NAD$^+$ from oxaloacetate and NADH. An exemplary malate dehydrogenase from *Chlorobium tepidum* is locus CAA56810.

Fumarase (also known as fumarate hydratase) (EC 4.2.1.2) generates fumarate and water from malate. *E. coli* encodes 3 different fumarase genes, which can be overexpressed in photoautotrophic organisms. An exemplary *E. coli* fumarase hydratase class I, (aerobic isozyme) is fumA. An exemplary *E. coli* fumarate hydratase class I (anaerobic isozyme) is fumB. An exemplary *E. coli* fumarate hydratase class II is fumC.

Succinate dehydrogenase (EC 1.3.99.1) generates succinate and FAD$^+$ from fumarate and FADH$_2$. *E. coli* encodes a four-subunit succinate dehydrogenase complex (SdhCDAB). These enzymes are also used in the 3-HPA pathway above, but in the reverse direction. It is important to note that some species may favor one direction or the other. Succinate dehydrogenase and fumarate reductase are reverse directions of the same enzymatic interconversion, succinate+FAD$^+$→fumarate+FADH$_2$. In *Escherichia coli*, the forward and reverse reactions are catalyzed by distinct complexes: fumarate reductase operates under anaerobic conditions and succinate dehydrogenase operates under aerobic conditions. This group also includes a region of the B subunit of a cytosolic archaeal fumarate reductase, for example the SdhA flavoprotein subunit, locus NP__415251; the SdhB iron-sulfur subunit, locus NP__415252; the SdhC membrane anchor subunit, locus NP__415249; and the SdhD membrane anchor subunit, locus NP__415250.

Acetyl-CoA:succinate CoA transferase (also known as succinyl-CoA synthetase) (EC 6.2.1.5) generates succinyl-CoA, ADP, and Pi from succinate, CoA, and ATP. *E. coli* encodes a heterotetramer of two alpha and beta subunits. An exemplary *E. coli* succinyl-CoA synthetase subunit alpha is sucD, locus AAA23900. An exemplary *E. coli* succinyl-CoA synthetase subunit beta is sucC, locus AAA23899. *Chlorobium tepidum* sucC (AAM71626) and sucD (AAM71515) may also be used.

2-oxoketoglutarate synthase (also known as alpha-ketoglutarate synthase) (EC 1.2.7.3) generates alpha-ketoglutarate, CO$_2$, and oxidized ferredoxin from succinyl-CoA, CO$_2$, and reduced ferredoxin. An exemplary enzyme from *Chlorobium limicola* DSM 245 is a 4 subunit enzyme with accession numbers EAM42575; EAM42574; EAM42853; and EAM42852. This activity was functionally expressed in *E. coli*. Yun N R, Arai M, Ishii M, Igarashi Y. Biochem Biophys Res Communic (2001). The Genes for anabolic 2-oxoglutarate: Ferredoxin oxidoreductase from *Hydrogenobacter thermophilus* TK6. 282 (2): 589-594. There is another 5-subunit OGOR cluster in the same bacterium. Yun N R et al. Biochem Biophys Res Communic (2002). A novel five-subunit-type 2-oxoglutalate:ferredoxin oxidoreductases from *Hydrogenobacter thermophilus* TK-6. 292(1):280-6. The corresponding genes are forDABGE. An exemplary alpha-ketoglutarate synthase from *Hydrogenobacter thermophilus* is the heterodimeric enzyme that includes korA, locus AB046568:46-1869 and the korB locus AB046568:1883-2770.

Isocitrate dehydrogenase (EC 1.1.1.42) generates D-isocitrate and NADP+ from alpha-ketoglutarate, $CO_2$, and NADPH. An exemplary gene is the monomeric type idh from *Chlorobium limicola*, locus EAM42635. Another exemplary enzyme is that from *Synechococcus* sp WH 8102, icd, accession CAE06681.

In another embodiment, the NAD-dependent isocitrate dehydrogenase (EC 1.1.1.41) is expressed which generates isocitrate and $NAD^+$ from alpha-ketoglutarate, $CO_2$, and NADH. An exemplary NAD-dependent enzyme is the two-subunit mitochondrial version from *Saccharomyces cerevisiae*. Subunit 1, idh1 locus YNL037C. The second subunit is idh2, locus YOR136W.

Aconitase (also known as aconitate hydratase or citrate hydrolyase) (EC 4.2.1.3) generates citrate from D-citrate via a cis-aconitate intermediate. *E. coli* encodes aconitate hydratase 1 and 2 (acnA and acnB). An exemplary aconitate hydrase 1 is *E. coli* acnA, locus b1276. An exemplary *E. coli* aconitate hydratase 2 is acnB, locus b0118.

Pyruvate synthase (also known as pyruvate:ferredoxin oxidoreductase) (EC 1.2.7.1) generates pyruvate, CoA, and an oxidized ferrodoxin from acetyl-CoA, $CO_2$, and a reduced ferredoxin. An exemplary pyruvate synthase is the tetrameric enzyme porABCD from *Clostridium tetani* E88, whereby subunit porA, locus AAO36986; subunit porB, locus AAO36985; subunit porC, locus AAO36988; and subunit porD, locus AAO36987.

Phosphoenolpyruvate synthase (also known as PEP synthase, pyruvate, water dikinase) (EC 2.7.9.2) generates phosphoenolpyruvate, AMP, and Pi from pyruvate, ATP, and water. *E. coli* encodes an exemplary PEP synthase, ppsA. The *E. coli* ppsA enzyme, locus AAA24319 and the corresponding enzyme from *Aquifex aeolicus* VF5 ppsA, locus AAC07865, may also be used.

Phosphoenolpyruvate carboxylase (also known as PEP carboxylase PEPCase, PEPC) (EC 4.1.1.31) generates oxaloacetate and Pi from phosphoenolpyruvate, water, and $CO_2$. *E. coli* encodes an exemplary PEP carboxylase, ppC. The *E. coli* ppC enzyme, locus CAA29332 may also be used.

The above enzymes, described in this section, confer the ability to synthesize an organic 2-carbon acetyl-CoA molecule from 2 molecules of $CO_2$. The stoichiometry of this reaction is 2 $CO_2$+2ATP+3NADH+1FADH$_2$+CoASH→acetyl-CoA+2ADP+2Pi+AMP+PPi+FAD$^+$+3NAD$^+$.

III. Enzymes for a Functional Woods-Ljungdahl Cycle

The following enzyme activities are expressed in to establish a functional Woods-Ljungdahl pathway. This pathway is natively employed by *Moorella thermoacetica* (previously known as *Clostridium thermoaceticum*), *Methanobacterium thermoautrophicum*, and *Desulfobacterium autotrophicum*.

NADP-dependent formate dehydrogenase (EC 1.2.1.4.3) generates formate and $NADP^+$ from $CO_2$ and NADPH. An exemplary NADP-dependent formate dehydrogenase is the two-subunit Mt-fdhA/B enzyme from *Moorella thermoacetica* (previously known as *Clostridium thermoaceticum*) which contains Mt-fdhA, locus AAB18330 and the beta subunit, Mt-fdhB, locus AAB18329.

Formate tetrahydrofolate ligase (EC 6.3.4.3) generates 10-formyltetrahydrofolate, ADP, and Pi from formate, ATP, and tetrahydrofolate. An exemplary formate tetrahydrofolate ligase is from *Clostridium acidi-urici*, locus M21507. Alternate sources for this enzyme activity include locus AAB49329 from *Streptococcus mutans* (Swiss-Prot entry Q59925), or the protein with Swiss-Prot entry Q8XHL4 from *Clostridium perfringens* encoded by the locus BA000016.

Methenyltetrahydrofolate cyclohydrolase (also known as 5,10-methylenetetrahydrofolate dehydrogenase) (EC 3.5.4.9 and 1.5.1.5) generates 5,10-methylene-THF, water, and $NADP^+$ from 10-formyltetrahydrofolate and NADPH via a 5,10-methyenyltetrahydrofolate intermediate. *E. coli* encodes a bifunctional methenyltetrahydrofolate cyclohydrolase/dehydrogenase, folD for example, the *E. coli* enzyme, locus AAA23803. Alternate sources for this enzyme activity include locus ABC19825 (folD) from *Moorella thermoacetica*, locus AAO36126 from *Clostridium tetani*; and locus BAB81529 from *Clostridium perfringens*. All are bifunctional folD enzymes.

Methylene tetrahydrofolate reductase (EC 1.5.1.20) generates 5-methyltetrahydrofolate and $NADP^+$ from 5,10-methylene-trahydrofolate and NADPH. *E. coli* encodes an exemplary methylene tetrahydrofolate reductase, metF for example, the *E. coli* enzyme, locus CAA24747. Alternative sources for this enzyme activity include locus AAC23094 from *Haemophilus influenzae* and locus CAA30531 from *Salmonella typhimurium*.

5-methyltetrahydrofolate corrinoid/iron sulfur protein methyltransferase generates tetrahydrofolate and a methylated corrinoid Fe—S protein from 5-methyl-tetrahydrofolate and a corrinoid Fe—S protein. An exemplary gene, acsE, is encoded by locus AAA53548 in *Moorella thermoacetica*. This activity has been functionally expressed in *E. coli* (Roberts D L, Zhao S, Doukov T, and Ragsdale S. The reductive acetyl-CoA Pathway: Sequence and heterologous expression of active methyltetrahydrofolate:corrinoid/Urib-sulfur protein methyltransferase from *Clostridium thermoaceticum*. J. Bacteriol (1994). 176(19):6127-30). Another source for this activity is encoded by the acsE gene from *Carboxydothermus hydrogenoformas* locus CP000141.

Carbon monoxide dehydrogenase/acetyl-CoA synthase (EC 1.2.7.4/1.2.99.2 and 2.3.1.169) is a bifunctional two-subunit enzyme which generates acetyl-CoA, water, oxidized ferredoxin, and a corrinoid protein from $CO_2$, reduced ferredoxin, and a methylated corrinoid protein. An exemplary carbon monoxide dehydrogenase enzyme, subunit beta, is encoded by locus AAA23228 from *Moorella thermoacetica*. Another exemplary source of this activity is encoded by the acsB gene, locus CHY_1222 from *Carboxydothermus hydrogenoformase* with protein accession YP_360060. An exemplary acetyl-CoA synthase, subunit alpha, is locus AAA23229 from *Moorella thermoacetica*.

The above enzymes, described in this section, confer the ability to synthesize an organic 2-carbon acetyl-CoA molecule from 2 molecules of $CO_2$. The stoichiometry of this reaction is 2$CO_2$+1ATP+2NADPH+2 reduced ferredoxins+coenzyme A→acetyl-CoA+2$H_2O$+ADP+Pi+2NADP$^+$+2 oxidized ferredoxins.

Cells engineered to contain a functional $CO_2$ fixation pathway are selected for via growth in minimal media lacking an organic carbon source. In addition to survival-based selections, cells can be grown in minimal media in the presence of radiolabeled $CO_2$ (i.e., $C^{14}$—$CO_2$). Detailed incorporation studies are employed to verify and characterize metabolic assimilation using common techniques known to those skilled in the art.

IV. Enzymes for a Functional Reductive Pentose Phosphate Cycle

The following enzyme activities are expressed to establish a functional reductive pentose phosphate (Calvin) cycle. This pathway is natively employed by all plants, algae, and cyanobacteria.

Ribulose-1,5-bisphosphate carboxylase/oxygenase (RuBisCO) (EC 4.1.1.39) which productively generates two molecules of 3-phosphoglycerate from ribulose-1,5-bisphosphate, $CO_2$, and $H2_o$. As its name suggests, RuBisCO can also catalyze a non-productive oxygenation reaction. Several classes of RuBisCO are known, any and all of which can be over-expressed [Watson G M F, Tabita F R. *FEMS Microbiology Letters* (1997) "Microbial ribulose 1,5-bisphosphate carboxylase/oxygenase: a molecule for phylogenetic and enzymological investigation." 146(1):13-22]. An exemplary Type I "Green-like" RuBisCO arising from the purple bacterial group comes from *Synechococcus* sp WH7803 (Ribulose-1,5-bisphosphate carboxylase/oxygenase-small subunit (CbbS), locus AAB48081) and (Ribulose-1,5-bisphosphate carboxylase/oxygenase-large subunit (CbbL), locus AAB8080). An exemplary Form I "Green-like" RuBisCO arising from the cyanobacterial/plant group comes from *Synechococcus elongatus* PCC 6301 (Ribulose-1,5-bisphosphate carboxylase/oxygenase—small subunit (RbcS), locus YP__170839) and (Ribulose-1,5-bisphosphate carboxylase/oxygenase—large subunit (RbcL), locus YP__170840). An exemplary Form I "Red-like" RuBisCO comes from *Rhodobacter sphaeroides* (Ribulose-1,5-bisphosphate carboxylase/oxygenase-small subunit (CbbS), locus P27998) and (Ribulose-1,5-bisphosphate carboxylase/oxygenase-large subunit (CbbL), locus P27997). An exemplary Form II RuBisCO comes from *Rhodobacter sphaeroides* as well (Ribulose-1,5-bisphosphate carboxylase/oxygenase (CbbM), locus P29278). Finally, an exemplary Form III RuBisCO comes from *Methanocaldococcus jannaschii* (Ribulose-1,5-bisphosphate carboxylase/oxygenase (RbcL), locus Q58632).

In some embodiments, rubisco activase is overexpressed to improve the activation of RuBisCO and/or to release competitive inhibitors of RuBisCO carbon fixation. An exemplary rubisco activase is comes from *Synechococcus* sp. JA-3-3Ab (locus ABC98646).

Phosphoglycerate kinase (PGK) (EC 2.7.2.3) generates 1,3-bisphosphoglycerate ADP from 3-phosphoglycerate and ATP. An exemplary phosphoglycerate kinase is locus BAD78623 from *Synechococcus* sp. PCC 6301.

Glyceraldehyde-3-phosphate dehydrogenase (GAPDH) (EC 1.2.1.13) generates glyceraldehyde 3-phosphate and $NADP^+$ from 1,3-bisphosphoglycerate and NADPH. An exemplary GAPDH is encoded by the cbbG gene, locus NP__875968 from *Prochlorococcus marinus*.

Triosephosphate isomerase (EC 5.3.1.1) generates dihydroxyacetone phosphate (DHAP) from glyceraldehyde 3-phosphate. An exemplary triosephosphate isomerase is encoded by the tpiA gene, locus Q59994 from *Synechocystis* sp. PCC 6803.

Fructose-1,6-bisphosphate aldolase (EC 4.1.2.13) generates fructose-1,6-bisphosphate from DHAP and glyceraldehyde 3-phosphate. An exemplary class I fructose 1,6-bisphosphate aldolase is encoded by the fda gene, locus NP__441723 from *Synechocystis* sp. PCC 6803. An exemplary class II fructose 1,6-bisphosphate aldolase is encoded by the fbaA gene, locus BAA10184 from *Synechocystis* sp. PCC 6803.

Fructose-1,6-bisphosphatase (EC 3.1.3.11) generates fructose-6-phosphate and $P_i$ from fructose-1,6-bisphosphate and $H_2 0$. An exemplary fructose-1,6-bisphosphatase is encoded by the fbp gene, locus NP__441738 from *Synechocystis* sp. PCC 6803.

Transketolase (EC 2.2.1.1) generates xylulose 5-phosphate and erythrose 4-phosphate from fructose 6-phosphate and glyceraldehyde 3-phosphate. An exemplary transketolase is encoded by the tktA gene, locus YP__171693 from *Synechococcus* sp. PCC 6301.

Pentose-5-phosphate-3-epimerase (EC 5.1.3.1) generates ribose-5-phosphate from xylulose-5-phosphate. An exemplary Pentose-5-phosphate-3-epimerase is encoded by the rpe gene, locus YP__171630 from *Synechocystis* sp. PCC 6301.

Sedoheptulose-1,7-bisphosphate aldolase (EC 4.1.2.13) generates sedoheptulose-1,7-bisphosphate from erythrose-4-phosphate and DHAP. An exemplary Sedoheptulose-1,7-bisphosphate aldolase is encoded by the rpaA gene, locus NP__681166 from *Thermosynechococcus elongatus* BP-1.

Sedoheptulose-1,7-bisphosphatase (SBPase) (EC 3.1.3.37) generates sedoheptulose-7-phosphate and Pi from sedoheptulose-1,7-bisphosphate and $H_2O$. An exemplary SBPase is encoded by the csbp gene, locus CAA52439 from *Chlamydomonas reinhardtii*.

Transketolase (EC 2.2.1.1) generates ribose 5-phosphate and xylulose 5-phosphate from sedoheptulose 7-phosphate and glyceraldehyde 3-phosphate. An exemplary transketolase is encoded by the tktA gene, locus YP__171693 from *Synechococcus* sp. PCC 6301.

Ribose 5-phosphate isomerase (EC 5.3.1.6) generates ribulose-5-phosphate from xylulose-5-phosphate or ribose-5-phosphate. An exemplary ribose-5-phosphate isomerase is encoded by the rpiA gene, locus YP__171649 from *Synechococcus elongatus* PCC 6301.

Phosphoribulokinase (EC 2.7.1.19) generates ribulose-1,5-bisphosphate and ADP from ribulose-5-phosphate and ATP. An exemplary phosphoribulokinase is the prk4 gene, locus AAA33090 from *Chlamydomonas reinhardtii*. In certain embodiments, the small CP12 protein is overexpressed, which regulates the Calvin cycle in via association/dissociation of PRK/CP12/GAPDH complexes depending on the ratio of NADPH/NADH [Tamoi M, Miyazaki T, Fukamizo T, Shigeoka S. "The calvin cycle in cyanobacteria is regulated by CP12 via the NAD(H)/NADP(H) ratio under light/dark conditions." The Plant Journal (2005). 42:504-12]. An exemplary CP12 gene is locus BAC09372 from *Thermosynechococcus elongatus* BP-1.

In certain embodiments, carbon fixation rates and/or carbon product efficiencies are enhanced by altering carbon flux to specific key intermediates. In one embodiment, carbon flux is directed towards acetyl-CoA via overexpression of pantothenate kinase, such as locus YP__473820 from *Syenchococcus* sp JA-3-3Ab and/or pyruvate dehydrogenase, such as pdhAB, locus YP__1728660 (pdhA) and YP__172072 (pdhB) from *Synechococcus* PCC 6301. In addition or as an alternative, endogenous genes that effectively reduce carbon flux through acetyl-CoA are downregulated or knocked-out. In these embodiments, acyl coenzyme A dehydrogenase (EC 1.3.99.3, locus YP__171045), glycerol-3-phosphate dehydrogenase (EC 1.1.1.94, locus YP__401539), and/or lactate dehydrogenase (ldhA) (EC 1.1.1.28, locus YP__170916) are downregulated or knocked-out.

Certain enzymes described above provide pathways to assimilate $CO_2$ into the 2-carbon acetyl-CoA (reductive TCA and Woods-Ljungdahl pathways) or glyoxylate (3-HPA pathway). Combinations of these (preferentially the 3-HPA cycle and the reductive TCA cycle) are also engineered in special cases. In this scenario, the outputs of the $CO_2$ fixation reactions (acetyl-CoA and glyoxylate) are utilized as inputs for the glyoxylate cycle, which combines acetyl-CoA and glyoxylate into 4-carbon oxaloacetate (via a 4-carbon malate intermediate) [Chung T, Klumpp D J, Laporte D C. J Bacteriol (1988). "Glyoxylate bypass operon of *Escherichia coli*: cloning and determination of the functional map." 170(1): 386-92.] Three key enzymes are involved in the glyoxylate shunt pathway. In preferred embodiments, all are overexpressed to maximize $CO_2$ fixation.

Malate synthase (EC 2.3.3.9) generates malate and coenzyme A from acetyl-CoA, water, and glyoxylate. An exemplary enzyme is encoded by *E. coli* locus JW3974 (aceB). Another exemplary activity is provided by an alternate malate synthase enzyme *E. coli* encodes, the JW2943 locus malate synthase G (glcB).

Isocitrate lyase (EC 4.1.3.1) generates glyoxylate and succinate from isocitrate. An exemplary enzyme is that encoded by *E. coli* locus JW3975 (aceA).

Malate dehydrogenase (EC 1.1.1.37) generates oxaloacetate and NADH from malate and $NAD^+$. An exemplary enzyme is that encoded by *E. coli* locus JW3205 (mdh).

Gluconeogenesis is the process by which organisms generate glucose from non-sugar carbon substrates, including pyruvate, lactate, glycerol, and glucogenic amino acids. Most steps of glycolysis are bidirectional, with three exceptions (reviewed in Hers H G, Hue, L. Ann Rev. Biochem (1983). "Gluconeogenesis and related aspects of glycolysis." 52:617-53). In certain embodiments, these enzyme activities are expressed to improve gluconeogenesis rates.

I. Conversion of Pyruvate to Phosphoenolpyruvate

Conversion of pyruvate to phosphoenolpyruvate requires two enzymatic activities as follows.

Pyruvate carboxylase (EC 6.4.4.1) generates oxaloacetate, ADP, and Pi from pyruvate, ATP, and $CO_2$. An exemplary pyruvate carboxylase is encoded by the YGL062W locus from *Saccharomyces cerevisiae*, pyc1.

Phosphoenolpyruvate carboxykinase (EC 4.1.1.49) generates phosphoenolpyruvate, ADP, Pi, and $CO_2$ from oxaloacetate and ATP. An exemplary phosphoenolpyruvate carboxykinase is encoded by *E. coli* locus JW3366, pck4.

II. Conversion of Fructose 1,6-Bisphosphate to Fructose-6-Phosphate

Conversion of fructose 1,6-bisphosphate to fructose-6-phosphate requires fructose-1,6-bisphosphatase (EC 3.1.3.11), which generates fructose-6-phosphate and Pi from fructose-1,6-bisphosphate and water. An exemplary fructose-1,6-bisphosphatase is encoded by *E. coli* locus JW4191, fbp, (EC #4.1.2.13).

The *Thermosynechoccocus elongates* BP-1 genes fbpI (Accession Number: NP_682066), fbpII (Accession Number: NP_681331) and fbaA (Accession Number: NP_681166) encoding, respectively, a fructose bisphosphatase I protein (E.C. 1.6.1.1), a fructose bisphosphatase II protein (E.C. 1.6.1.1) and a fructose bisphosphatase aldolase protein (E.C. XXX) were amplified directly from *Thermosynechoccocus elongates* BP-1 strain genomic DNA using the following primers: fbpI forward primer 5'-GAATA-CATATGACTGACTATGCAGCC-3' (SEQ ID NO: 7) and reverse fbpI primer 5'-GAATAGAATTCTTACACCTGTGT-CACGG-3' (SEQ ID NO: 8); fbpII forward primer 5'-GAAT-AGTCTCATATGGATAACGTCATCGG-3' (SEQ ID NO: 9) and reverse primer 5'GAATAGAATTCTTAGTACAGCTG-GAGTG-3' (SEQ ID NO: 10); fbaA forward primer 5'-GAATACATATGGCACTCGTACCCATG-3' (SEQ ID NO: 11) and reverse primer 5'-GAATAGAATTCTATAAC-CACCACGG-3' (SEQ ID NO: 12). PCR amplifications were performed with PCR SuperMix High Fidelity (Invitrogen, Carlsbad, Calif.) and standard PCR amplification conditions. The fbpI and fbpII forward primer adds an NdeI restriction recognition site, the fbaA forward primer adds a BsmAI restriction recognition site, and all reverse primers add a stop codon and an EcoRI restriction recognition site.

The amplified fbpI, fbpII and fbaA PCR gene products were cloned into the pJB5 expression vector ("pJB5-fbpI;" "pJB5-fbpII;" "pJB5-fbaA") by digesting the insert and vector individually with NdeI and EcoRI or BsmAI and EcoRI (New England Biolabs) restriction endonucleases with well known laboratory techniques. Digestions were gel isolated on 0.8% TAE agarose gel, purified using a Gel Extraction Kit (Qiagen) and ligated with the T4 DNA Ligase (New England Biolabs) with no deviation from the published techniques. The ligated product was transformed into NEB 5-alpha chemically competent *E. coli* cells using standard techniques (New England Biolabs), and confirmed by PCR.

pJB5-fbpI, pJB5-fbpII and pJB5-fbaA plasmid stocks were purified using Qiagen miniprep kit for individual transformation into separate preparations of JCC136. One to two micrograms of the aforementioned plasmid DNAs were added to individual JCC136 cell preparations having an $OD_{730\ nm}$ of 1 and incubated at 37 C for 4 hours using low intensity orbital shaking and low level light source. Cells were then plated onto $A^+$ solid media plates and placed in a lighted incubator (100-250 µE/m2/s, 37C) for 1 day. Twenty-five micrograms/$ml_{[final]}$ spectinomycin was underlayed on the plates and incubated until colonies grew (~5 days). Integration into target Synechococcus host cells was confirmed by PCR of whole cell genomic DNA by a "colony PCR" protocol for the pJB5-fbpI transformation. Briefly, ~1 mm colonies were resuspended in 50 µl deionized water, and 5 µl were used in 20 µl standard PCR reactions using Phusion DNA Polymerase Master Mix (New England Biolabs, Beverly, Mass.) with the addition of a 2 minute 98 C denaturation step at the very start of the standard PCR cycling conditions. The PCR showed correct bands for colonies, and the strain was named JCC136-FbpI (FIG. 10, panel B, lane 2).

A single colony of both JCC136 and JCC136-FbpI was grown in 10 mL $A^+$ with 100 µg/$ml_{[final]}$ spectinomycin in a test tube immersed in a 37C bath with bubbled 1% $CO_2$. Cultures were grown to $OD_{730nm}$ 5.0 or higher (Molecular Devices Spectramax M2e; previously determined that an $OD_{730\ nm}$ of 1 is equal to ~0.3 g CDW), and then spun down (21,000 RCF, 20C, 5 min), resuspended in fresh A+ media to original concentration, and then appropriately back-diluted to $OD_{730nm}$ 0.2 in 25 mL $A^+$ in a baffled 125 mL shaker flask. Approximately 1 mL of culture was taken for each time point (0, 24, 48, 72, and 96 hours post-dilution, $OD_{730nm}$ was recorded (appropriately diluted to give reading between 0.04 and 0.4, which was previously determined to be most accurate range on the Spectramax M2e). Samples were immediately spun down at 4 C for 10 min at 21,000 RCF. Supernatants were placed in a new tube, and frozen at −80C until ready for analysis.

The supernatant from each time point was analyzed for ethanol and acetaldehyde by use of an Agilent 7890 Gas Chromatograph equipped with a headspace analyzer and a flame ionization detector (Agilent) using a J&W Scientific DB-ALC1 (Catalog Number: 123-9134; length: 30 m, Inner Diameter, 0.320 mm, Film Thickness: 1.80 µm). One hundred µl of each sample was subjected to headspace analysis. Controls were measured for A+ alone, and as well as from serial dilution of standards for ethanol and acetaldehyde obtained from Sigma to obtain a calibration curve. The levels of ethanol, and ethanol normalized with respect to the optical density are plotted in FIG. 11.

III. Conversion of Glucose-6-Phosphate to Glucose

Conversion of glucose-6-phosphate to glucose requires glucose-6-phosphatase (EC 3.1.3.68), which generates glucose and Pi from glucose-6-phosphate and water. An exemplary glucose-6-phosphatase is encoded by the *Saccharomyces cerevisiae* YHR044C locus, dog1. Another exemplary glucose-6-phosphatase activity is encoded by *Saccharomyces cerevisiae* YHR043C locus, dog2.

Oxaloacetate, the starting material for gluconeogenesis, is generated either via the glyoxylate shunt (leveraging inputs from the reductive TCA or Woods-Ljungdahl pathways and the 3-HPA pathway) or via the carboxylation of pyruvate. In the absence of the glyoxylate shunt, the pyruvate synthase activity of pyruvate ferredoxin:oxidoreductase (EC 1.2.7.1) can generate pyruvate, CoA, and oxidized ferredoxin from acetyl-CoA, $CO_2$, and reduced ferredoxin [Furdui C and Ragsdale S W. J. Biol. Chem. (2000). "The role of pyruvate ferredoxin oxidoreductase in pyruvate synthesis during autotrophic growth by the Woods-Ljungdahl pathway." 275 (37): 28494-99]. An exemplary pyruvate ferredoxin oxidoreductase with pyruvate synthase activity is encoded by locus Moth_0064 from *Moorella thermoaceticum*.

Example 3

Engineering Reducing Power

The above $CO_2$-fixation pathways may require generating reducing power, primarily in the form of NADH (nicotinamide adenine dinucleotide, reduced form) and NADPH (nicotinamide adenine dinucleotide phosphate, reduced form).

Maintaining an appropriately-balanced supply of reduced $NAD^+$ (NADH) and $NADP^+$ (NADPH) is important to maximize carbon assimilation, and thus growth rate, of engineered photoautotrophic organisms.

Table 1 lists candidate genes for overexpression in the reducing power module together with information on associated pathways, Enzyme Commission (EC) Numbers, exemplary gene names, source organism, GenBank accession numbers, and homologs from alternate sources.

I. NADH

When NADH levels remain suboptimal, a plurality of methods is employed to increase intracellular NADH concentrations, including overexpression of the following genes.

$NAD^+$-dependent isocitrate dehydrogenase (EC 1.1.1.41) generates 2-oxoglutarate, $CO_2$, and NADH from isocitrate and $NAD^+$. Of note, most bacterial isocitrate dehydrogenases are $NADP^+$-dependent (EC 1.1.1.42). An exemplary $NAD^+$-dependent isocitrate dehydrogenase is the octameric *Saccharomyces cerevisiae* enzyme comprising locus YNL037C, idh1 and locus YOR136W, idh2.

Malate dehydrogenase (EC 1.1.1.37) generates oxaloacetate and NADH from malate and $NAD^+$. Overexpression of NAD-dependent malate dehydrogenase can be employed to increase NADH pools. An exemplary enzyme is encoded by *E. coli* locus JW3205 (mdh).

The NADH:ubiquinone oxidoreductase from *Rhodobacter capsulatus*, is unique in its ability to reverse electron flow between the quinone pool and $NAD^+$ [Dupuis A, Peinnequin A, Darrouzet E, Lunardi J. FEMS Microbiol Lett (1997). "Genetic disruption of the respiratory NADH-ubiquinone reductase of *Rhodobacter capsulatus* leads to an unexpected photosynthesis-negative phenotype." 149:107-114; Dupuis A, Darrouzet E, Duborjal H, Pierrard B, Chevallet M, van Belzen R, Albracht S P J, Lunardi J. Mol. Microbiol. (1998). "Distal genes of the nuo_operon of *Rhodobacter capsulatus* equivalent to the mitochondrial ND subunits are all essential for the biogenesis of the respiratory NADH-ubiquinone oxidoreductase. 28:531-541]. The *Rhodobacter* Nuo operon, encoding the Nuo Complex I, can be reconstituted to generate additional NADH by reverse electron flow.

The *Rhodobacter capsulatus* nuo operon, locus AF029365, consisting of the 14 nuo genes nuoA-N (and 7 ORFs of unknown function) can be expressed to enable reverse electron flow and NADH-generation in photoautotrophic cells. The operon encodes NuoA, accession AAC24985.1; NuoB, accession AAC24986.1; NuoC, accession AAC24987.1; NuoD, accession AAC24988.1; NuoE, accession AAC24989.1; NuoF, accession AAC24991.1; NuoG, accession AAC24995.1; NuoH, accession AAC24997.1; NuoI, accession AAC24999.1; NuoJ, accession AAC25001.1; NuoK, accession AAC25002.1; NuoL, accession AAC25003.1; NuoM, accession AAC25004.1; and NuoN, accession AAC25005.1.

Expression of pyridine nucleotide transhydrogenase (EC 1.6.1.1) generates NADH and $NADP^+$ from NADPH and $NAD^+$. An exemplary enzyme is the *E. coli* soluble pyridine nucleotide transhydrogenase, encoded by sthA (also known as udhA), locus JW551. An alternate exemplary enzyme is the membrane bound *E. coli* pyridine nucleotide transhydrogenase, encoded by the multisubunit of NAD(P) transhydrogenase subunit alpha, encoded by pntA, locus JW1595, and NADP transhydrogenase subunit beta, encoded by pntB, locus JW1594.

Expression of udhA Gene Encoding Pyridine Nucleotide Transhydrogenase for NADH Production The *Escherichia coli* K12 udhA gene (Accession Number: NP_418397) encoding a pyridine nucleotide transhydrogenase (E.C.# 1.6.1.1) was amplified directly from *E. coli* K12 strain genomic DNA using the forward primer 5'-TATGCCA-CATTCCTACGATTACGATGCC-3' (SEQ ID NO: 13) and the reverse primer 5'-AATTCTTAAAACAGGCGGTT-TAAACCGTTTAACGC-3' (SEQ ID NO: 14). PCR amplifications were performed with the high fidelity Phusion DNA Polymerase Master Mix (New England Biolabs, Beverly, Mass.). The forward primer adds an NdeI restriction recognition site, and the reverse Primer adds a stop codon and an EcoRI restriction recognition site.

The amplified udhA PCR gene product was cloned into the pJB5 expression vector ("pJB5-udhA") by digesting the insert and vector individually with NdeI and EcoRI (New England Biolabs) restriction endonucleases with well known laboratory techniques. Both digestions were gel isolated on 1% TAE agarose gel, purified using a Gel Isolation Kit (Qiagen) and ligated with the Quick Ligation Kit (New England Biolabs) with no deviation from the published techniques. The ligated product was transformed into EPI400 chemically competent cells using standard techniques (Epi-Centre), and confirmed by PCR.

pJB5-udhA plasmid stocks were purified using Qiagen miniprep kit for transformation into *Synechococcus* sp. PCC 7002. One to two micrograms of pJB5-udhA plasmid was added to *Synechococcus* sp PCC 7002 cells grown to an optical density of 1 and incubated at 37 C for 4 hours using low intensity orbital shaking and low level light source. Cells were then plated onto $A^+$ solid media plates and placed in a lighted incubator (100-250 µE/m2/s, 37C) for 1 day. Twenty-five micrograms/mL spectinomycin was underplayed on the plates and incubated until colonies grew (~5 days). Integration into target *Synechococcus* host cells is confirmed by PCR of whole cell genomic DNA by a "colony PCR" protocol. Briefly, ~1 mm colonies were resuspended in 50 μl deionized water, and 5 μl were used in 20 μl standard PCR reactions using Phusion DNA Polymerase Master Mix (New England Biolabs, Beverly, Mass.) with the addition of a 2 minute 98 C degree denaturation step at the very start of the standard PCR cycling conditions. The PCR showed correct bands for colonies, and the strain was named JCC1-UdhA (FIG. 10, lane 2 and 3).

II. NADPH

NADPH serves as an electron donor in reductive (especially fatty acid) biosynthesis. Three parallel methods are used, singly or in combination, to maintain sufficient NADPH levels for photoautotrophy. Methods 1 and 2 are described in WO2001/007626, Methods for producing L-amino acids by increasing cellular NADPH. Method 3 is described in U.S. Pub. No. 2005/0196866, Increasing intracellular NADPH availability in *E. coli*.

Expression of the zwf Gene Encoding Glucose-6-Phosphate Dehydrogenase for NADPH

The *Escherichia coli* K12 zwf gene (Accession Number: AAC74922) encoding a glucose-6-phosphate dehydrogenase (E.C. 1.1.1.49) was amplified directly from *E. coli* K12 strain genomic DNA using the forward primer 5'-TCGACATATG-GCGGTAACGCAAACAGCCC-3' (SEQ ID NO: 15) and the reverse primer 5'-TCGAGAATTCTTACTCAAACTCAT-TCCAGGAACGACCATC-3' (SEQ ID NO: 16). PCR amplifications were performed with the high fidelity Phusion DNA Polymerase Master Mix (New England Biolabs, Beverly, Mass.). The forward primer adds an NdeI restriction recognition site, and the reverse Primer adds a stop codon and an EcoRI restriction recognition site.

The amplified zwf gene PCR product was cloned into the pJB5 expression vector ("pJB5-Zwf") by digesting the insert and vector individually with NdeI and EcoRI (New England Biolabs) restriction endonucleases with well known laboratory techniques. Both digestions were gel isolated on 1% TAE agarose gel, purified using a Gel Isolation Kit (Qiagen) and ligated with the Quick Ligation Kit (New England Biolabs) with no deviation from the published techniques. The ligated product was transformed into EPI400 chemically competent cells using standard techniques (EpiCentre), and confirmed by PCR.

pJB5-Zwf plasmid stocks were purified using Qiagen miniprep kit for transformation into *Synechococcus* sp. PCC 7002. One to two micrograms of pJB5-Zwf plasmid was added to *Synechococcus* sp PCC 7002 cells grown to an optical density of 1 and incubated at 37 C for 4 hours using low intensity orbital shaking and low level light source. Cells were then plated onto $A^+$ solid media plates and placed in a lighted incubator (100-250 μE/m2/s, 37C) for 1 day. Twenty-five micrograms/ml spectinomycin was underplayed on the plates and incubated until colonies grew (~5 days). Integration into target *Synechococcus* host cells is confirmed by PCR of whole cell genomic DNA by a "colony PCR" protocol. Briefly, ~1 mm colonies were resuspended in 50 μl deionized water, and 5 μl were used in 20 μl standard PCR reactions using Phusion DNA Polymerase Master Mix (New England Biolabs, Beverly, Mass.) with the addition of a 2 minute 98 C degree denaturation step at the very start of the standard PCR cycling conditions. The PCR showed correct bands for colonies, and the strain was named JCC1-Zwf (FIG. 10, lane 4).

A. Increasing the Flux Through the Pentose Phosphate Pathway

Increasing the flux through the Pentose Phosphate Pathway generates 2 molecules of NADPH per molecule of glucose.

The downregulation or inactivation of the phosphoglucose isomerase, such as pgi from *Synechococcus* sp. PCC 6301 (locus YP_172776), is known to force glucose through the pentose phosphate pathway. This therefore provides one approach for increasing intracellular NADPH pools, as has been previously applied in *E. coli* engineering [Kabir, M M. Shimizu, K. Appl. Microbiol. Biotechnol. (2003):Fermentation characteristics and protein expression patterns in a recombinant *Escherichia coli* mutant lacking phosphoglucose isomerase for poly(3-hydroxybutyrate) production." 62:244-255; Kabir M M, Shimizu K. J. Biotechnol (2003). "Gene expression patterns for metabolic pathway in pgi knockout *Escherichia coli* with and without phb genes based on RT-PCR" 105(1-2):11-13.]

Overexpression of glucose-6-phosphate dehydrogenase (EC 1.1.1.49), which generates NADPH and 6-phospho-gluconolactone from glucose-6-phosphate and $NADP^+$, provides another way to increase NADPH levels. An exemplary enzyme is that encoded by *E. coli* glucose-6-phosphate dehydrogenase, zwf, locus JW1841.

Overexpression of 6-phosphogluconolactonase (EC 3.1.1.31), which generates 6-phosphogluconate from 6-phosphoglucolactone and water, provides another approach for increasing flux through the pentose phosphate pathway. An exemplary enzyme is that encoded by the *E. coli* 6-phosphogluconolactonase, pgl, locus JW0750.

Overexpression of 6-phosphogluconate dehydrogenase (EC 1.1.1.44) generates ribose-5-phosphate, $CO_2$, and NADPH from 6-phosphogluconate and $NADP^+$. This also can be used to increase NADPH levels by increasing flux through the pentose phosphate pathway. An exemplary enzyme is the encoded by *E. coli* 6-phosphogluconate dehydrogenase, gnd, locus JW2011.

B. Expression of $NADP^+$-Dependent Enzymes $NADP^+$-dependent enzymes can be expressed in lieu of or in addition to NAD-dependent enzymes.

Overexpression of isocitrate dehydrogenase (EC 1.1.1.42) generates 2-oxoglutarate, $CO_2$, and NADPH from isocitrate and $NADP^+$. An exemplary enzyme is encoded by the *E. coli* isocitrate dehydrogenase, icd, locus JW1122.

Overexpression of malic enzyme (EC 1.1.1.40) generates pyruvate, $CO_2$, and NADPH from malate and $NADP^+$. An exemplary NADP-dependent enzyme is the *E. coli* malic enzyme, encoded by maeB, locus JW2447.

C. Expression of Pyridine Nucleotide Transhydrogenase

Expression of pyridine nucleotide transhydrogenase (EC 1.6.1.1) generates NADPH and $NAD^+$ from NADH and $NADP^+$. An exemplary enzyme is the *E. coli* soluble pyridine nucleotide transhydrogenase, encoded by sthA (also known as udhA), locus JW551. An alternate exemplary enzyme is the membrane bound *E. coli* pyridine nucleotide transhydrogenase, encoded by the multisubunit of NAD(P) transhydrogenase subunit alpha, encoded by pntA, locus JW1595 and NADP transhydrogenase subunit beta, encoded by pntB, locus JW1594.

Example 4

Improved Thermotolerance

In certain embodiments, photobioreactors are maintained at high operating temperatures. Engineering photoautotrophic organisms to withstand and thrive in high operating temperatures allows for reduced cooling costs and faster kinetics of carbon-based product output. Four significant ways to increase thermotolerance in photoautotrophic organisms include stabilizing the photosynthetic apparatus with accessory proteins, expressing chaperones to stabilize other intracellular proteins in the cell, altering the lipid profiles of cell membranes, and expressing osmoprotectants, such as betaine.

Photosystem II is the most heat sensitive protein in the photosynthetic apparatus [Berry J, Bjorkman O. *Plant Physiol* (1980) "Photosynthetic response and adaptation to temperature in higher plants." 31:491]. The damage to Photosystem II is primarily located within the oxygen-evolving components of the complex, and degradation of and replacement of D1 represents a key step in the repair of damaged Photosystems [Nixon P J, Barker M, Boehm M, de Vries R, Komenda J. "FtsH-mediated repair of the photosystem II complex in response to light stress." J. Exp. Biol (2005). 56(411):357-63]. In one embodiment, three genes—psbO, psbU, and psbV—that are known to protect these oxygen-evolving components in Photosystem II of *Synechocystis* sp. PCC 6803 are overexpressed to aid in thermotolerance [Kimura A, Eaton-Rye J J, Morita E H, Nishiyama Y, Hayashi H. *Plant Cell Physiol*. (2002). "Protection of the Oxygen-Evolving Machinery by the Extrinsic Proteins of Photosystem II is Essential for Development of Cellular Thermotolerance in *Synechocystis* sp. PCC 6803." Plant Cell Physiol. 43(8):932-938]. These three exemplary genes encode amino acid sequences are Photosystem II manganese-stabilizing polypeptide (PsbO), locus NP_441796; PS II complex 12 kDa extrinsic protein (PsbU), locus NP_440167; and Cytochrome c550 (PsbV), locus NP_441834.

A secondary source of thermal toxicity results from general protein instability at high temperatures. Several chaperones specifically confer thermotolerance by assisting protein folding and degradation at high temperatures including as ClpB [Eriksson M, Schelin J, Miskiewicz E, Clarke A K. *J Bacteriol* (2001) "Novel Form of ClpB/HSP100 Protein in the *Cyanobacterium Synechococcus*." 183(24):7392-7396], GroESL [Rajaram H, Ballal A D, Apte S K, Wiegert T, Schumann W. Biochimica et *Biophysica Acta* (2001) "Cloning and characterization of the major groESL operon from a nitrogen-fixing cyanobacterium *Anabaena* sp. strain L-31." 1519(1-2): 143-146], and HspA [Roy S K, Hiyama T, Nakamoto H. *Eur J Biochem* (1999). "Purification and characterization of the 16-kDa heat-shock-responsive protein from the thermophilic cyanobacterium *Synechococcus vulcanus*, which is an alpha-crystallin-related, small heat shock protein." 262(2):406-416]. In the preferred embodiment, the orthologues of these genes from the thermophile *Thermosynechococcus elongatus* BP-1 are overexpressed to confer increased thermotolerance to the photoautotrophic organisms. These exemplary genes encode amino acid sequences are 16.6 kDa small heat shock protein molecular chaperone (HspA), locus NP_681663; 60 kD chaperonin 1 (GroEL-1), locus NP_680976; 60 kD chaperonin 2 (GroEL-2), locus NP_682202; Co-chaperonin (GroES), locus NP_680977; and Endopeptidase (ClpB), locus NP_683242.

As an alternative or in addition, endogenous repressors of proteins involved in thermotolerance are downregulated or deleted. For example, exemplary regulatory genes that can be disrupted include hrcA, such as locus NP_440130 of *Synechocystis* sp. PCC 6803 [Nakamoto H, Suzuki M, Kojima K. "Targeted inactivation of the hrcA repressor gene in cyanobacteria." FEBS Lett (2003). 549(1-3):57-62] and the histidine kinase hik34, such as locus slr1285 of *Synechocystis* sp. PCC 6803, [Suzuki I, Kanesaki Y, Hayashi H, Hall J, Simon W J, Slabas A R, Murata N. "The histidine kinase Hik34 is involved in thermotolerance by regulating the expression of heat shock genes in *Synechocystis*." Plant Physiol (2005). 138(3): 1409-21.]

In addition or as an alternative, the lipid profile of cellular and intracellular membrane can be modified to increase thermotolerance. Of note, most thermotolerant organisms have evolved mechanisms to retain highly saturated fatty acids, frequently with lengthy and/or cyclic fatty acid tails. If natively expressed in the desired photoautotrophic organism, it is useful to downregulate or knock-out fatty acid desaturases (EC 1.14.19) such as delta-12-desaturase, for example the desA gene (locus NP_441489) of *Synechocystis* sp. PCC 6803, delta-15 desaturase, for example the desB, locus NP_441622 of *Synechocystis* sp. PCC 6803, stearoyl-CoA 9-desaturase (EC 1.14.19.1), for example the desC gene, locus NP_442430 of *Synechocystis* sp. PCC 6803, and/or delta-6-desaturase (EC 1.14.19.3), for example the desD gene, locus NP_441824 of *Synechocystis* sp. PCC 6803.

In addition or as an alternative, pathways to enable biosynthesis of the osmoprotectant betaine are engineered to improve thermotolerance of photoautotrophic organisms [Yang X, Wen X, Gong H, Lu Q, Yang Z, Tang Y, Liang Z, Lu C. "Genetic engineering of the biosynthesis of glycinebetaine enhances thermotolerance of photosystem II in tobacco plants." Planta (2007). 225(3):719-33]. In this embodiment, a glycine sarcosine methyltransferase is expressed to convert glycine to sarcosine and sarcosine to dimethylglycine, as well as a dimethylglycine methyltransferase, to catalyze the methylation of dimethylglycine to betaine [Waditee R, Bhuiyan N H, Rai V, Aoki K, Tanaka Y, Hibino T, Suzuki S, Takano J, Jagendorf A T, Takabe T, and Takabe T. "Genes for direct methylation of glycine provide high levels of glycine-betaine and abiotic-stress tolerance in *Synechococcus* and *Arabidopsis*. Proc Natl Acad Sci (2005). 102(5):1318-23]. An exemplary glycine sarcosine methyltransferase gene is encoded by ApGSMT, locus BAC56939, from *Aphanothece halophytica*. An exemplary dimethylglycine methyltransferase is encoded by ApDMT, locus BAC56940 from *Aphanothece halophytica*.

Example 5

Improved pH Tolerance

In certain embodiments, elevated $CO_2$ levels are used to increase bioproductivity. However, elevating $CO_2$ levels in photobioreactors can cause concomitant increases to the acidity of the culture medium that can be toxic to the cell. Engineering cells to be tolerant to higher acidity conditions increases productivity and reduces costs associated with external pH control. In the present invention, one or more mechanisms to confer acid tolerance are engineered into the cell.

Two similar and complementary mechanisms of acid resistance use amino acid based decarboxylation and export to increase intracellular pH [Richard H, Foster J W. *J Bacteriol* (2004) "*Escherichia coli* Glutamate- and Arginine-Dependent Acid Resistance Systems Increase Internal pH and Reverse Transmembrane Potential." 186(18):6032-6041]. The genes required for the glutamate-based acid resistance are the glutamate decarboxylase isozymes GadA and GadB, as well as the glutamate/GABA antiporter GadC. The arginine-based acid resistance requires the arginine decarboxylase AdiA and the arginine/agmatine anti-porter AdiC. In addition, both acid-tolerance mechanisms require at least one of the Cl⁻ channels EriC and MriT [Iyer R, Iverson T M, Accardi A, Miller C. *Nature* (2002) "A biological role for prokaryotic ClC chloride channels." 419(6908):715-718]. In the preferred embodiment, the genes required for one or both of these amino-acid based acid-resistance mechanisms from the enteric bacterium *Escherichia coli* K12 are overexpressed to confer increased acid tolerance. These exemplary genes encode amino acid sequences are glutamate decarboxylase A (GadA), EC 4.1.1.15, locus NP_417974; Glutamate decarboxylase beta (GadB), 4.1.1.15, locus NP_416010; glutamate:gamma-aminobutyric acid antiporter (GadC), locus NP_416009; biodegradative arginine decarboxylase (AdiA), EC 4.1.1.19, locus NP_418541); arginine:agmatin antiporter (AdiC), locus NP_418539); Chloride channel protein (EriC), locus NP_414697; and Chloride channel protein (MriT), locus NP_416109.

In addition, or as an alternative, genes known to be involved in bacterial acid response mechanisms are overexpressed to confer acid tolerance to engineered bacteria. Thirty-two genes have been previously identified to be overexpressed in response to acid stress in response to acid stress [Ohta H, Shibata Y, Haseyama Y, Yoshino Y, Suzuki T, Kagasawa T, Kamei A, Ikeuchi M, Enami I. *Photosynth Res* (2005) "Identification of genes expressed in response to acid stress in *Synechocystis* sp. PCC 6803 using DNA microarrays." 84(1-3):225-230]. In the preferred embodiment, the one or more of the genes expressed in the bacterium *Synechocystis* sp. PCC 6803 are overexpressed to confer increased acid tolerance. These exemplary genes encode amino acid sequences are Chaperone protein dnaK2 (DnaK), locus NP_441989; DNA-directed RNA polymerase, sigma subunit (sll0306), locus NP_441950; Zn-dependent protease (sll0528), locus NP_442805; metal-dependent phosphoesterase (sll0549), locus NP_442414; Acid-stress tolerance protein (sll0846), locus NP_441124; Acid-stress related membrane protein (sll0939), locus NP_440194; Acid-stress tolerance protein (sll1086), locus NP_441667; Acid-stress tolerance protein (sll1483), locus NP_442911; 16.6 kDa small heat shock protein, molecular chaperone (sll1514), locus NP_440316; mannose-1-phosphate guanyltransferase (sll1558), EC 2.7.7.13, locus NP_441699; RNA polymerase sigma factor (sll2012), locus NP_441031; carboxyl-terminal processing protease (slr0008), EC 3.4.21.102, locus NP_442119; molecular chaperone (slr0093), locus NP_442496; Acid-stress tolerance protein (slr0270), locus NP_441273; Geranylgeranyl pyrophosphate synthase (slr0611), locus NP_439899; Acid-stress tolerance protein (slr0967), locus NP_440193; CheY-like receiver (slr1214), locus NP_440716; Signal transduction histidine kinase (slr1285), locus NP_441610; Acid-stress tolerance protein (slr1413), locus NP_440062; superoxide dismutase (slr1516), EC 1.15.1.1, locus NP_441347; Acid-stress tolerance protein (slr1544), locus NP_440790; Acid-stress tolerance protein (slr1573), locus NP_442902; Acid-stress tolerance protein (slr1674), locus NP_441676; hydrogenase expression/formation protein (slr1675), locus NP_441677; Acid-stress tolerance protein (slr1676), locus NP_441678; Acid-stress tolerance protein (slr1687), locus NP_441698; Acid-stress tolerance protein (slr1915), locus NP_440459; Esterase (slr1916), locus NP_440460; Hydrogenase component protein (ssl3044), locus NP_441697; Acid-stress tolerance protein (ssl3769), locus NP_441305; Acid-stress tolerance protein (ssr2016), locus NP_440709; Acid-stress tolerance protein (ssr2595), locus NP_440789).

Example 6

Flue Gas Tolerance

Flue gas typically consists of $N_2$ (80%), $CO_2$ (10-15%), $O_2$ (2-3%), as well as trace amounts of CO (70-110 ppm), $NO_x$ (most typically $NO_2$) (50-70 ppm), $SO_2$ (180-250 ppm). Of the components of flue gas, only $NO_x$ and $SO_2$ are thought to adversely effect the growth of photoautotrophic organisms [Negoro M, Shioji N, Miyamoto K, Miura Y. "Growth of microalgae in high $CO_2$ gas and effects of $SO_x$ and $NO_x$." Appl Biochem Biotechnol (1991). Spring (28-29): 877-86.].

In preferred embodiments, photoautotrophic cells are engineered to exhibit improved tolerance to $NO_x$, including $NO_2$. One exemplary means for improving tolerance to $NO_2$ is via overexpression of the ncgA (NP_841001), ncgB (NP_841000), and ncgC (NP_840999) genes from *Nitrosomonas europaea*, [Beaumont H J, Lens S I, Westerhoff H V, and van Spanning R J. "Novel nirK cluster genes in *Nitrosomonas europaea* are required for NirK-dependent tolerance to nitrite." J. Bacteriol (2005). 187(19):6849-51].

In preferred embodiments, photoautotrophic cells are engineered to exhibit improved tolerance to $SO_x$, including $SO_2$. One exemplary means for improving tolerance to $SO_2$ is via overexpression of cysteine synthase A, cysK, from *Synechococcus* PCC 7942 (YP_398721) [O-acetyl-L-Ser(thiol)-lyase] (EC 4.2.99.8 and 2.5.1.47) [Noji M, Saito, M, Nakamura M, Aono M, Saji H, Saito K. "Cysteine synthase overexpression in tobacco confers tolerance to sulfur-containing environmental pollutants." Plant Physiology (2001). 126:973-980]. In addition or as an alternative, superoxide dismutase is overexpressed, such as the exemplary sodA (NP_441347; EC 1.15.1.1) gene from *Synechocystis* sp. PCC 6803. In preferred embodiments, catalase is also overexpressed, such as the katG (NP_441295; EC 1.11.16) gene from *Synechocystis* sp. PCC 6803 [Tseng M J, Liu C W, Yiu J C. "Enhanced tolerance to sulfur dioxide and stress of transgenic Chinese cabbage plants expressing both superoxide dismutase and catalase in chloroplasts." Plant Physiol. Biochem (2007). 45(10-11):822-33].

Heavy metals such as lead, chromium, copper mercury and the like are byproducts of industrial combustive processes, commonly released through exhaust flue gases and pose a toxic threat to cyanobacteria. Genes have been identified that can be engineered into cyanobacteria to confer resistance to these and other heavy metals pollutants. For example, genes potentially relevant for imparting resistance to heavy metals can be found on natural plasmids pMOL28 (accession number NC_006525) and pMOL30 (accession number NC_006466). These plasmids were originally identified in *Ralstonia metallidurans*, a bacterium colonizing soils in industrial sediments, soils and wastes or in other regions having high levels of heavy metal toxicity. The pMOL28 and pMOL30 plasmids confer heavy metal resistance for cobalt, nickel and chromate (pMOL28) and cobalt, zinc, cadmium, copper, lead and mercury (pMOL30). For example, pMOL28 genes and proteins known to be involved with lead tolerance include pbrT (accession number YP_145624), pbrR (accession number YP_145623), Pb-efflux ATPase (accession number YO_145622) and pbrD (accession number YP_145620). pMOL28 genes involved in nickel and cobalt resistance include cnrC (accession number CAI30229), cnrA (accession number CAI30227), putative nickel and cobalt resistance genes (accession number CAI1305; CAI1304;

CAI1303). Multi-substrate recognition proteins (cobalt-zinc-cadmium) are encoded by genes czcD (accession number YP_145593.1), czcC (accession number YP_145593.1) and czcB (accession number YP_145594.1). pMOL30 genes for copper resistance include copA (accession number YP_145682.1), copK (accession number Q58AD3; 2K0Q_A), copC (accession number YP_145680.1), copD (accession number YP_145679.1) and copper resistance transmembrane protein (accession number YP_14682). pMOL30 genes for chromate resistance genes include chrB (accession number YP_16177) and a gene for chromate transport protein (accession number YP_161712). Other heavy metal resistance genes on pMOL30 can confer tolerance to mercury and include a gene for mercuric transport protein (accession number YP_161729), a gene for periplasmic mercuric ion-binding protein (accession number YP_161728), a gene for putative mercuric reductase (accession number YP_161727) and a gene for putative mercury resistance protein (accession number YP_161725).

Other sources of genes conferring metal resistance are identified in *Sulfolobus solfataricus*, comprising two genes for mercury resistance, merI (accession number ABL96631) and merH (accession number ABL96629) and a gene for mercuric reductase, merA (accession number ABL96630). Alternatively, an operon conferring mercury resistance has been identified in *Streptomyces* sp. CHR28, comprising mercuric reductase merA (accession number AAF64138), organomercurial lyase merB (accession number AAF64140), mercury transport merT (accession number AAF64136), orfIV (accession number AAF64134) and extracellular mercury binding protein merP (accession number AAF64135).

These examples represent only some of the potential genetic sources for conferring heavy metal resistance and are not to be construed as inclusive and limiting. For example, recently a Turkish group reported a plasmid mediated multiple heavy metal resistance from bacteria isolated from a landfill (M N Unaldi-Coral, et al., *Annals Microbio*. (2005) vol. 55(3):175-179). Other sources of metal resistance genes include plants and yeasts (S. Clemens, et al., *EMBO* (1999) vol. 18:3325-3333), *Pseudomonas* species (D. Reneiro, et al., *Gene* (1995) vol. 166:77-82) bacterial species such as *Escherichia coli* subjected to adaptive pressures from toxic environments (KR Brocklehurst and A P Morby, *Microbiology* (2000) vol. 146:2277-2282) and others.

Feasibility studies have shown that bacterial species can successfully be transformed and express genes mediating heavy metal tolerance. For example *Escherichia* species have been altered to confer mercury tolerance from genes found in other bacteria such as *Bacillus* (Y. Wang, et al., *J. Bacteriology* (1987) vol. 169:4848-4851) as well as higher organisms including mice (C C Huang, et al. *Gene* (1999) vol. 239:361-366.

Example 7

Engineered Salt Tolerance

In many geographic locales, available water supplies are affected by high salinity. As a result, in certain embodiments it is advantageous to propagate photoautotrophic organisms in brackish (8-500 mM NaCl) or sea water (~530 mM). When the photoautotrophic cell of interest is unable to thrive under these conditions, it is necessary to overexpress nucleic acids conferring salt tolerance.

In one embodiment, a $Na^+/H^+$ antiporter is overexpressed. An exemplary $Na^+/H^+$ antiporter is the apnhaP gene (locus BAB69459) from the halotolerant cyanobacteria *Aphanothece halophytica* [Waditee R, Hibino T, Nakamura T, Incharoensakdi A, and Takabe T. "Overexpression of a $Na^+/H^+$ antiporter confers salt tolerance on a freshwater cyanobacterium, making it capable of growth in sea water." Proc Natl Acad Sci (2002). 99(6):4109-4114]. In some instances, catalase is also overexpressed, such as the katG (NP_441295; EC 1.11.16) gene from *Synechocystis* sp. PCC 6803 to improve growth rates in sea water.

In addition or as an alternative, the novel salt and cadmium stress related gene, scsr, locus BAE53693 of *Chlamydomonas* sp. W80 is expressed. [Tanaka S, Suda Y, Ikeda K, Ono M, Miyasaka H, Watanabe M, Sasaki K, and Hirata K. "A novel gene with antisalt and anticadmium stress activities from the halotolerant marine green alga *Chlamydomonas* sp. W80." FEMS Microbiol Lett (2007). 271:48-52].

In addition or as an alternative the breast basic conserved gene, bbc1, locus BAA23724 of *Chlamydomonas* sp. W80 is expressed. [Tanaka S, Ikeda K, and Miyasaka H. "Enhanced tolerance against salt-stress and freezing-stress of *Escherichia coli* cells expressing algal bbc1 gene." Curr. Microbiol. (2001). 42:173-177].

In addition or as an alternative, pathways to enable biosynthesis of the osmoprotectant betaine are engineered to improve salt tolerance properties of photoautotrophic organisms. In this embodiment, a glycine sarcosine methyltransferase is expressed to convert glycine to sarcosine and sarcosine to dimethylglycine, as well as a dimethylglycine methyltransferase, to catalyze the methylation of dimethylglycine to betaine [Waditee R, Bhuiyan N H, Rai V, Aoki K, Tanaka Y, Hibino T, Suzuki S, Takano J, Jagendorf A T, Takabe T, and Takabe T. "Genes for direct methylation of glycine provide high levels of glycinebetaine and abiotic-stress tolerance in *Synechococcus* and *Arabidopsis*. Proc Natl Acad Sci (2005). 102(5):1318-23]. An exemplary glycine sarcosine methyltransferase gene is encoded by ApGSMT, locus BAC56839, from *Aphanothece halophytica*. An exemplary dimethylglycine methyltransferase is encoded by ApDMT, locus BAC56940 from *Aphanothece halophytica*.

Improved Salt-Tolerant Transgenic Cyanobacteria

A putative Na/H+ antiporter from *Synechococcus* sp. PCC 7002, which was identified by homology to the Na/H+ antiporter from *Aphanothece halophytica* (Accession Number: BAB69459), was amplified by PCR using the following primers: NaH Forward Primer—TCATCATATGCCTTTGGT-CATGATTGTTTAGCAGAAC (SEQ ID NO: 17), NaH Reverse Primer—ATATCAATTGTTAACTCTGAAT-TGTTTTTTCGGTGGCTTTG (SEQ ID NO: 18). The Forward Primer adds an NdeI restriction endonuclease recognition site, and the Reverse Primer adds an MfeI restriction site.

The PCR product was cloned into pJB263 by digesting the insert and vector individually with NdeI and EcoRI (New England Biolabs). Both digestions were gel isolated on a 1% TAE agarose gel, purified using a Gel Extraction Kit (Qiagen), and ligated using the Quick Ligation Kit (New England Biolabs) using standard techniques. The ligated product was transformed into EPI400 chemically competent *E. coli* cells using standard techniques (EpiCenter), and confirmed by PCR. The resulting plasmid, pJB263-NaH, was confirmed by PCR analysis.

Cells of *Synechocystis* sp. PCC 6803 are transformed with pJB263-NaH using the following procedure. pJB263-NaH plasmid stocks were purified using Qiagen miniprep kit for transformation into *Synechocystis* sp. PCC 6803. One to two micrograms of pJB263-NaH plasmid is added to *Synechocystis* sp PCC 6803 cells grown to an optical density of 1 and incubated at 30 C for 4 hours using low intensity orbital shaking and low level light source. Cells are then plated onto A+ solid media plates and is placed in a lighted incubator (100-250 uE/m2/s, 30C) for 1 day. Twenty-five micrograms/mL spectinomycin is underlayed on the plates and incubated until colonies grew (~5 days). Integration into target *Synechocystis* host cells is confirmed by PCR of whole cell genomic DNA by a "colony PCR" protocol:

Example 8

Nutrient Independence

In addition to CO2 and light, photoautotrophic organisms typically require inorganic nutrient sources and vitamins. Required nutrients are generally supplemented to the growth media during bench-scale propagation of such organisms. However, such nutrients are prohibitively expensive in the context of industrial scale bioprocessing.

Nitrogen is a key constituent of a variety of cellular macromolecules, including amino acids and nucleotides. Engineering photoautotrophs to efficiently utilize inexpensive sources provides significant economic and practical advantages.

In one embodiment, photoautotrophs are engineered to fix $N_2$, which is found present in concentrations of nearly 80% (v/v) in air and flue gas. In this embodiment, genes required for nitrogen fixation are overexpressed, in addition to genes required for synthesis of required cofactors and accessory protein [Herrero A, Muro-Pastor A M, Flores E. *J Bacteriol* (2001) "Nitrogen Control in Cyanobacteria". 183(2): 411-425]. Eighteen such exemplary genes are found in *Nostoc* sp PCC 7120: FeMo cofactor biosynthesis protein (NifB), locus NP_485557; [4Fe-4S] ferredoxin (FdxN), locus BAB77882; L-Cysteine desulfurase (NifS), EC 2.8.1.7, locus NP_485499; Fe cluster accessory protein (NifU), locus NP_485498; Nitrogenase-Fe subunit (NifH), EC 1.18.6.1, locus NP_485497; Nitrogenase-alpha subunit (NifD), EC 1.18.6.1, locus NP_485484; Nitrogenase-beta subunit (NifK), EC 1.18.6.1, locus NP_485483; FeMo cofactor biosynthesis protein (NifE), locus NP_485481; FeMo cofactor biosynthesis protein (NifN), locus NP_485480; FeS cluster accessory protein (Nifx), locus NP_485479; FeMo cofactor accessory protein (NifW), locus NP_485476; FeMo cofactor accessory protein (HesA), locus NP_485475; FeS cofactor accessory protein (HesB), locus NP_485474; Nitrogen-fixation specific ferredoxin (FdxH), locus NP_485473; Pyruvate-flavodoxin oxidoreductase (NifJ), EC 1.2.7.1, locus NP_486843; homocitrate synthase (NifV), EC 2.3.3.14, locus NP_485450; FeMo cofactor accessory protein (NifZ), locus NP_485451; and FeMo cofactor accessory protein (NifT), locus NP_485452). Overexpression of the above genes enables photoautotrophic organisms to grow with $N_2$ gas as the sole source of nitrogen.

In addition or as an alternative, photoautotrophs are engineered to assimilate nitrite, which is a trace component of flue gas. In this embodiment, cells must be engineered to express a nitrite/nitrate transporter and be conveyed with the ability to convert nitrite into ammonia. Exemplary gene sequences encoding active nitrate/nitrate transporters are found *Synechococcus* sp. PCC 6301 [Herrero A, Muro-Pastor A M, Flores E. *J Bacteriol* (2001) "Nitrogen Control in Cyanobacteria". 183(2): 411-425] and are overexpressed in cells to allow import of nitrates and nitrite, for example: ABC-type nitrate/nitrite transport system substrate-binding protein (NrtA), locus YP_171021; ABC-type nitrate/nitrite transport system permease protein (NrtB), locus YP_171022; ABC-type nitrate/nitrite transport system ATP-binding protein (NrtC), locus YP_171023; ABC-type nitrate/nitrite transport system ATP-binding protein (NrtD), locus YP_171024). As an alternative, the single polypeptide Nitrate/Nitrite transporter (NrtP) gene from *Synechococcus* sp. PCC 7002 is overexpressed [Sakamoto T, Inoue-Sakamoto K, Bryant D A. *J Bacteriol* (1999). "A Novel Nitrate/Nitrite Permease in the Marine Cyanobacterium *Synechococcus* sp. Strain PCC 7002." 181(23):7363-7372], Nitrite/Nitrate permease (NrtP), locus AAD45941.

At elevated concentrations, nitrite is toxic to most cells. To alleviate nitrite toxicity, photoautotrophic cells are engineered to overexpress genes within the nitrite tolerance operon found in *Nitrosomonas europaea* ATCC 19718 [Beaumont H J E, Lens S I, Westerhoff H V, van Spanning R J M. "Novel nirK Cluster Genes in *Nitrosomonas europaea* Are Required for NirK-Dependent Tolerance to Nitrite." *J Bacteriol* (2005). 187(19):6849-6851], Multicopper oxidase type 1 (NirK), locus NP_840998; Cytochrome c, class IC (NcgA), locus NP_841001; Cytochrome c, class I (NcgB), locus NP_841000; Cytochrome c, class IC (NcgC), locus NP_840999.

In addition or as an alternative, photoautotrophic cells are engineered to assimilate ammonia. In this embodiment, cells are engineered to overexpress an ammonium permease. An exemplary ammonium permease found in *Synechocystis* sp. PCC 6803 [Montesinos M L, Muro-Pastor A M, Herrero A, Flores E. "Ammonium/Methylammonium Permeases of a Cyanobacterium. Identification and analysis of three nitrogen-regulated amt genes in *Synechocystis* sp. PCC 6803." J Biol Chem (1998). 273(47):31463-31470] is overexpressed High affinity ammonium/methylammonium permease (Amt1), locus NP_442561; Ammonium/methylammonium permease (Amt2), locus NP_440272; Ammonium/methylammonium permease (Amt3), locus NP_442793.

In addition or as an alternative, photoautotrophic cells are engineered to assimilate urea. In this embodiment, cells must be engineered to overexpress a urea transporter to enable efficient uptake of urea into the cell. An exemplary urea transporter found in *Nostoc* sp. PCC 7120 [Valladares A, Montesinos M L, Herrero A, Flores E. "An ABC-type, high-affinity urea permease identified in cyanobacteria." *Molecular Microbiology* (2002). 43(3):703-715] is overexpressed comprising the five gene ABC-type transporter for high affinity urea uptake for example ABC-type, high-affinity urea permease, periplasmic domain (UrtA), locus CAB70948.1; ABC-type, high-affinity urea permease, membrane domain (UrtB), locus CAB70949.1; ABC-type, high-affinity urea permease, membrane domain (UrtC), locus CAB70950.1; ABC-type, high-affinity urea permease, ATP binding domain (UrtD), locus CAB70951.1 and ABC-type, high-affinity urea permease, ATP binding domain (UrtE), locus CAB70952.1.

In addition, urea amidohydrolase (EC 3.5.1.5) ("urease") and its associated accessory proteins are overexpressed, which catalyze conversion of urea to ammonia and carbon dioxide. An exemplary urease found in *Synechococcus* sp. WH 7805 [Collier J, Brahamsha B, Palenik B. "The marine cyanobacterium *Synechococcus* sp. WH7805 requires urease to utilize urea as a nitrogen source: molecular-genetic and biochemical analysis of the enzyme" Microbiology (1999). 145(2):447-459] is overexpressed comprising the ureABC urease genes: Urea amidohydrolase, gamma subunit (UreA), locus AAC61500; Urea amidohydrolase, beta subunit (UreB), locus AAC61501; Urea amidohydrolase, alpha subunit (UreC), locus AAC61502; and the ureDEFG genes encoding the accessory proteins Urease accessory protein (UreD), locus AAC61499; Urease accessory protein (UreE), locus AAC61498; Urease accessory protein (UreF), locus AAC61497; and Urease accessory protein (UreG), locus AAC61496.

Vitamin B12 is a vitamin cofactor that facilitates radical-based reaction catalyzation. Many organisms, including at least half of all microalgae surveyed, such as *Synechococcus* sp. PCC 7002, require external sources of Vitamin B12 for growth, which is prohibitively expensive in large-scale industrial bioprocessing [Croft M T, Warren M J, Smith A G. "Algae Need Their Vitamins", Eukaryotic Cell (2006) 5(8): 1175-1183]. In one embodiment, the need for Vitamin B12 is obviated by engineering photoautotrophic cells to express the Vitamin B12 biosynthesis pathway. An exemplary biosynthesis pathway found in *Salmonella typhimurium* is overexpressed, including but not limited to the following 20 genes: Uroporphyrin-III C-methyltransferase (CysG), EC 2.1.1.107, locus NP_462380; Sirohydrochlorin cobaltochelatase (CbiK), EC 4.99.1.3, locus NP_460970; Precorrin-2 C20-methyltransferase (CbiL), EC 2.1.1.130, locus NP_460969; Precorrin-3B methylase (CbiH), EC 2.1.1.131, locus NP_460972; Bifunctional CbiG/precorrin methyltransferase (CbiG), locus NP_460973; Precorrin-4 C11-methyltransferase (CbiF), EC 2.1.1.133, locus NP_460974; Cobalamin biosynthesis protein (CbiD), locus NP_460977; NADPH-dependent precorrin-6A reductase (CbiJ), EC 1.3.1.54, locus NP_460971; Precorrin-6B C5,15-methyltransferase (CbiE), EC 2.1.1.132, locus NP_460976; Precorrin-6B C12 decarboxylase (CbiT), EC 2.1.1.132, locus NP_460975; Precorrin-8X-methylmutase (CbiC), EC 5.4.1.2, locus NP_460978; Cobyrinic acid A,C-diamide synthase (CbiA), EC 6.3.1.-, locus NP_460980; Cob(I)yrinic acid a,c-diamide adenosyltransferase (BtuR), EC 2.5.1.17, locus NP_460677; Cobyrinic acid synthase (CbiP), EC 6.3.5.10, locus NP_460964; Cobyric acid decarboxylase (CobD), EC 4.1.1.81, locus NP_459636; Adenosylcobinamide-phosphate synthase (CbiB), EC 6.3.1.10, locus NP_460979; Alpha ribazole-5'-P phosphatase (CobC), EC 3.1.3.73, locus NP_459635; Cobalamin(5'-phosphate) synthase (CobS), EC 2.7.8.26, locus NP_460962; Cobinamide phosphate guanylyl transferase (CobU), EC 2.7.7.62, locus NP_460963; and Nicotinate-nucleotide dimethylbenzimidazole-P phosphoribosyl transferase (CobT), EC 2.4.2.21, locus NP_460961).

In addition, to allow for cobalt uptake and incorporation into Vitamin B12, the genes encoding the cobalt transporter are overexpressed. The exemplary cobalt transporter protein found in *Salmonella typhimurium* is overexpressed ABC-type Co2+ transport system, permease component (CbiM), locus NP_460968; ABC-type cobalt transport system, periplasmic component (CbiN), locus NP_460967; and ABC-type cobalt transport system, permease component (CbiQ), locus NP_461989).

In a preferred embodiment, photoautotrophic organisms are engineered to overexpress Vitamin B12-independent enzymes to obviate the need for this cofactor entirely. In most photoautotrophic organisms, only methionine synthase (EC 2.1.1.13) and class II ribonucleotide reductases require Vitamin B12. An exemplary Vitamin B12-independent methionine synthase (EC 2.1.1.14) from *Thermotoga maritima* is therefore overexpressed: 5-methyltetrahydropteroyltriglutamate-homocysteine methyltransferase (MetE), locus NP_229090 (SEQ ID NO: 22). In addition, an exemplary class I ribonucleotide reductase (nrdAB) from *Synechocystis* sp. PCC 6803 is overexpressed: Ribonucleoside-diphosphate reductase, alpha subunit (NrdA), locus NP_441654; Ribonucleoside-diphosphate reductase, beta subunit (NrdB), locus NP_443040.

It is furthermore contemplated that nutrient independence (e.g., Vitamin B12) of host cells of the present invention can be accomplished by expression of various proteins encoding 5-methyltetrahydropteroyltriglutamate-homocysteine methyltransferase (metE), ribonucleoside-diphosphate reductase, alpha subunit (nrdA), and ribonucleoside-diphosphate reductase, beta subunit (nrdB) comprising sequences that are at least 80%, 85%, 90%, 91%, 92%, 93%, 94%, 95%, 96%, 97%, 98%, 99% or 100% identical to metE, nrdA or nrdB.

Strain Construction

The expression plasmid, pJB5, contains two 500 bp regions of DNA homologous to sequences on the natural pAQ1 plasmid of *Synechococcus* sp. PCC 7002. Between the two regions of homology is a promoter and ribosome binding site, sites for DNA sequence insertion, and a resistance cassette, aadA1, that confers resistance to spectinomycin. The metE genes from *E. coli* (NP_418273 (SEQ ID NO: 20)) and *Thermosynechococcus elongatus* BP-1 (NP_681881_ (SEQ ID NO: 21)) were encoded on pJB6 and pJB7 respectively. All the plasmids were digested with NdeI (New England Biolabs) and EcoRI (New England Biolabs), and the ~1 kb fragment from pJB6 and pJB7, and the large fragment from pJB5, were gel isolated and purified using standard techniques (Qiagen). The fragments from pJB6 and pJB7 were ligated and transformed into pJB5 using standard techniques to form pJB5-6 and pJB5-7.

*Synechococcus* sp. PCC 7002 was transformed with pJB5-6 and pJB5-7 as follows. pJB5-6 and pJB5-7 were digested and inactivated with SbfI (New England Biolabs) for 1 hour and heat inactivated. DNA was incubated with fresh cells at OD730 of 1 for 4 hours in a dark incubator at 37° C. in $A^+$. Cells were then allowed diluted in 20 mL fresh $A^+$ media with moderate light and bubbled with air with 1% $CO_2$ for 24 hours. Cells were then diluted 1 in 20 into fresh $A^+$ media containing 10 ug/mL spectinomycin and allowed to grow for 5 days under the same conditions. Cells were again diluted again 1 in 20 in 25 mL $A^+$ media lacking Vitamin B12, and this was repeated a second time after the cells grew to high density. After the second outgrowth cells were plated onto $A^+$ plates lacking Vitamin B12.

FIGS. 3A-D show wild-type *Synechococcus* sp. PCC 7002 and cells transgenically expressing *E. coli* MetE and *Thermosynechococcus elongatus* BP-1 MetE diluted and grown overnight in $A^+$ media lacking Vitamin B12. Cells were diluted, then plated and allowed to grow 1 week at 37° C. in a lighted incubator on both Vitamin B12 sufficient and deficient plates. FIG. 3A illustrates wild-type Synechococcus on B12 sufficient plate whereas FIG. 3B shows B12 deficient plate. FIG. 3C represents a transgenic Synechococcus strain with the *E. coli* MetE on Vitamin B12 deficient plate and FIG. 3D shows a *Thermosynechococcus elongatus* MetE on Vitamin B12 deficient plate. The results show the ability of transgenically expressed methionine synthase to rescue the Vitamin B12 requirements of cyanobacteria.

Example 9

Near Infra Red Absorbance

*Acaryochloris marina* is the only known organism to have chlorophyll (Chl) d as its main Chl constituent. Chl d absorbs far-red/near ir light in the range of 700 nm-750 nm and carries out oxygenic photosynthesis. It also contains Chl a, found in many organisms as the primary constituent. Chl a differs from Chl d only in that it has a vinyl group in place of a formyl group. We reasoned, then, that Chl d is derived from Chl a (or that a precursor of Chl d is derived from the analogous precursor of Chl a) by one or more of the mechanisms shown in FIG. 4.

The *Acaryochloris marina* genome has been sequenced and annotated, making it possible to locate putative oxygenase- and epoxide hydrolase-encoding genes contained within it. FIG. 6 lists those genes explicitly identified in the annotation of the *A. marina* as some form of "oxygenase". Because these identifications were made by homology comparisons with other known oxygenases, a further BLAST search was not conducted. FIG. 7 lists the genes from *A. marina* with the most similarity to the *Anabaena variabilis* gene encoding EC 3.2.2.3 (epoxide hydrolase), determined by Protein BLAST. All genes with an expect value of less than 0.5 are shown. The protein sequence used as the query is shown in FIG. 5.

It is noted in Swingley et al., PNAS 105:2005 (2008) that an alternative method of oxygenation is that which transfers oxygen from water using S-adenosylmethionine (SAM). The genes encoding putative proteins of this type are given in FIG. 8.

The protein corresponding to locus tag AM1_5665 (protein id ABW30612.1) [*Acaryochloris marina* MBIC11017] (FIG. 6B) was noted by Swingley et al., PNAS 105:2005 (2008) as being a likely oxygenase but not having significant homology with known examples. This could mean it is especially significant in Chl d formation.

The protein corresponding to locus tag AM1_2935 (protein id ABW27932.1) [*Acaryochloris marina* MBIC11017], a likely thioredoxin, was found in the GenBank annotation as the only gene explicitly containing "epox" (see FIG. 7).

The protein corresponding to locus tag AM1_5023 (protein id ABW29989.1) [*Acaryochloris marina* MBIC11017] and the protein corresponding to locus tag AM1_5798 (protein id ABW30743.1) [*Acaryochloris marina* MBIC11017] share little homology with other sequenced cyanobacteria, according to Swingley et al., PNAS 105:2005 (2008) and thus may be important in Chl d synthesis.

The *Acaryochloris marina* genes and the encoded protein sequences for photosystem proteins that can use chlorophyll d as a photoreceptor are provided in Japanese Kokai No. 2001-346585, titled "Photosystem proteins that can use chlorophyll d as a photoreceptor and the genes that code them," published Dec. 18, 2001, corresponding to Application number P2000-170696, filed Jun. 7, 200 by Marine Biotechnology Institute Co., Ltd, 1-28-10 Hongo, Bunkyo-ku, Tokyo, the entire disclosure of which is hereby incorporated by reference in its entirety. Amino acid sequences of six photosystem proteins corresponding to *Acaryochloris marina* locus tags AM1_2457, AM1_2458, AM1_2166, AM1_1083, AM1_2026, and AM1_1084 were retrieved from the Japanese Kokai No. 2001-346585 application and used as query sequences in BLASTP searches. The BLASTP searches identified full-length amino acid sequences corresponding to the six photosystem proteins set out in Table 6, which appears in FIG. 9.

The protein corresponding to *Acaryochloris marina* locus tag AM1_2457 (protein id ABW27465.1) [*Acaryochloris marina* MBIC11017] is the photosystem I core protein PsaA. The protein corresponding to *Acaryochloris marina* locus tag AM1_2458 (protein id ABW27466.1) [*Acaryochloris marina* MBIC11017] is photosystem I core protein PsaB. Together, these two subunit proteins assemble to form the photosystem I protein that converts light energy into redox power and reduces $NADP^+$ using electrons supplied by photosystem II.

The protein corresponding to *Acaryochloris marina* locus tag AM1_2166) (protein id ABW27180.1) [*Acaryochloris marina* MBIC11017] is photosystem II D1 protein PsbA. The protein corresponding to *Acaryochloris marina* locus tag AM1_1083) (protein id ABW26122.1) [*Acaryochloris marina* MBIC11017] is photosystem II D2 protein PsbD. Together PsbA and PsbD assemble and form the photosystem II protein. The photosystem II protein converts light energy into redox power, decomposes water and takes up electrons and supplies them to photosystem I.

The protein corresponding to *Acaryochloris marina* locus tag AM1_2026 (protein id ABW27041.1) [*Acaryochloris marina* MBIC11017] is photosystem II CP47 protein PsbB. The protein corresponding to *Acaryochloris marina* locus tag AM1_1084) (protein id ABW26123.1) [*Acaryochloris marina* MBIC11017] is photosystem II CP43 protein PsbC. PsbB and PsbC assemble and form the photosystem II core antenna proteins. Energy absorbed by the antenna to capture light energy used to decompose water is transmitted to the reaction center protein.

According to one embodiment of the invention a photoautotroph is created to absorb far-red/near IR light (i.e., in the neighborhood of 700 nm-750 nm). In this embodiment, genes required for synthesis of chlorophyll d and photosystem proteins I and II capable of binding chlorophyll d and using it as a photoreceptor for transducing light energy into reducing power are overexpressed. Exemplary genes include those encoding any of the *Acaryochloris marina* proteins disclosed herein.

TABLE 7

Informal Sequence Listing (5'→3')
(SEQ ID NOS 1-2 and 5-18)

TTGCTACCTGCAGGGCCACCACAGCCAAATTCATCGTT

GGTTGTGCGGCCGCAGTATTGGCTGTGATGTTGG

TATACATCATATGGGTAAATTATTACTGATATTAGGTAGTGTTATTGC

GCTACAATTGTTAAGCATTAGAAGATTCTTTAACAGCAACATTCC

GAATACATATGACTGACTATGCAGCC

GAATAGAATTCTTACACCTGTGTCACGG

GAATAGTCTCATATGGATAACGTCATCGG

GAATAGAATTCTTAGTACAGCTGGAGTG

GAATACATATGGCACTCGTACCCATG

GAATAGAATTCTATAACCACCACGG

TATGCCACATTCCTACGATTACGATGCC

AATTCTTAAAACAGGCGGTTTAAACCGTTTAACGC

TCGACATATGGCGGTAACGCAAACAGCCC

TCGAGAATTCTTACTCAAACTCATTCCAGGAACGACCATC

TCATCATATGCCTTTGGTCATGATTGTTTTAGCAGAAC

ATATCAATTGTTAACTCTGAATTGTTTTTTCGGTGGCTTTG

All references to publications, including scientific publications, treatises, pre-grant patent publications, and issued patents are hereby incorporated by reference in their entirety for all purposes. The teachings of the specification are intended to exemplify but not limit the invention, the scope of which is determined by the following claims.

We claim:

1. An engineered cyanobacterial cell for fuel production, wherein said cell comprises a recombinant nucleic acid encoding Vitamin $B_{12}$ independent methionine synthase, wherein said Vitamin $B_{12}$ independent methionine synthase is at least 95% identical to *Escherichia coli* K12 MetE of SEQ ID NO: 20, and wherein said cyanobacterial cell lacks an endogenous Vitamin $B_{12}$ independent methionine synthase.

2. The engineered cyanobacterial cell of claim 1, wherein said Vitamin $B_{12}$ independent methionine synthase is *Escherichia coli* K12 MetE of SEQ ID NO: 20.

3. The engineered cyanobacterial cell of claim 1, wherein said cyanobacterial cell is a *Synechococcus* species.

4. The engineered cyanobacterial cell of claim 2, wherein said cyanobacterial cell is a *Synechococcus* species.

5. The engineered cyanobacterial cell of claim 3 or 4, wherein said *Synechococcus* species is *Synechococcus* sp. PCC 7002.

6. A method for conferring Vitamin $B_{12}$ independence to a cyanobacterial cell, comprising transforming said cyanobacterial cell with a nucleic acid encoding a Vitamin $B_{12}$ independent methionine synthase at least 95% identical to *Escherichia coli* K12 MetE of SEQ ID NO: 20, wherein said cyanobacterial cell requires exogenous Vitamin $B_{12}$ for growth prior to said transformation.

7. The method of claim 6, wherein said Vitamin $B_{12}$ independent methionine synthase is *Escherichia coli* K12 MetE of SEQ ID NO: 20.

8. The method of claim 7, wherein said cyanobacterial cell is a *Synechococcus* species.

9. The method of claim 6, wherein said cyanobacterial cell is a *Synechococcus* species.

10. The method of claim 6 or 7, further comprising culturing said transformed cells in media lacking Vitamin $B_{12}$, wherein said media selects for the growth of said transformed cells.

11. The method of claim 8 or 9, wherein said *Synechococcus* species is *Synechococcus* sp. PCC 7002.

12. A method to produce a carbon-based product of interest, comprising
culturing an engineered cyanobacterial cell in the presence of $CO_2$ and light under conditions suitable to produce a carbon-based product of interest, wherein said engineered cyanobacterial cell is Vitamin $B_{12}$ independent, and wherein said engineered cyanobacterial cell comprises a recombinant nucleic acid encoding a Vitamin $B_{12}$ independent methionine synthase, wherein said Vitamin $B_{12}$ independent methionine synthase is at least 95% identical to *Escherichia coli* K12 MetE of SEQ ID NO: 20, and wherein said cyanobacterial cell lacks an endogenous Vitamin $B_{12}$ independent methionine synthase.

13. The method of claim 12, wherein Vitamin $B_{12}$ independent methionine synthase is *Escherichia coli* K12 MetE of SEQ ID NO: 20.

14. The method of claim 12, wherein said cyanobacterial cell is a *Synechococcus* species.

15. The method of claim 13, wherein said cyanobacterial cell is a *Synechococcus* species.

16. The method of claim 14 or 15, wherein said *Synechococcus* species is *Synechococcus* sp. PCC 7002.

* * * * *

SEQUENCE LISTING

<160> NUMBER OF SEQ ID NOS: 22

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ttgctacctg cagggccacc acagccaaat tcatcgtt                          38

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggttgtgcgg ccgcagtatt ggctgtgatg ttgg                              34

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgataaggcg cgccgaaact gcgccaagaa tagc                              34

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtgtatggcc ggccatcgcc tttatggtgc tttatgtg                          38

<210> SEQ ID NO 5
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tatacatcat atgggtaaat tattactgat attaggtagt gttattgc               48

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
gctacaattg ttaagcatta gaagattctt taacagcaac attcc            45

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaatacatat gactgactat gcagcc                                 26

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gaatagaatt cttacacctg tgtcacgg                               28

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gaatagtctc atatggataa cgtcatcgg                              29

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gaatagaatt cttagtacag ctggagtg                               28

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gaatacatat ggcactcgta cccatg                                 26

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
```

-continued gaatagaatt ctataaccac cacgg                                         25

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tatgccacat tcctacgatt acgatgcc                                      28

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aattcttaaa acaggcggtt taaaccgttt aacgc                              35

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tcgacatatg gcggtaacgc aaacagccc                                     29

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tcgagaattc ttactcaaac tcattccagg aacgaccatc                         40

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tcatcatatg cctttggtca tgattgtttt agcagaac                           38

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atatcaattg ttaactctga attgtttttt cggtggcttt g                       41

<210> SEQ ID NO 19
<211> LENGTH: 295
<212> TYPE: PRT
<213> ORGANISM: Anabaena variabilis

<400> SEQUENCE: 19

```
Met Phe Pro Ser Phe Leu Pro Ala Ala Val Gly Gln Leu Thr Glu Ser
1               5                   10                  15

Glu Ser Ile Ala Leu Ala Lys Thr Ile Gln Thr Gln Ala Ile Ala Thr
            20                  25                  30

Pro Leu Ser Asn Gln Pro Ile Thr Thr Ala Tyr Val Arg Gln Gly Ser
        35                  40                  45

Gly Gly Thr Pro Ile Leu Leu Ile His Gly Phe Asp Ser Ser Val Leu
    50                  55                  60

Glu Phe Arg Arg Leu Leu Pro Leu Leu Gly Lys Glu Asn Glu Thr Trp
65                  70                  75                  80

Ala Val Asp Leu Leu Gly Phe Gly Phe Thr Gln Arg Leu Ala Gly Ile
                85                  90                  95

Lys Phe Ser Pro Val Ala Ile Arg Thr His Leu Tyr Ser Phe Trp Lys
            100                 105                 110

Thr Leu Ile Asn Gln Pro Val Ile Leu Val Gly Ala Ser Met Gly Gly
        115                 120                 125

Ala Ala Ala Ile Asp Phe Thr Leu Thr Tyr Pro Glu Ala Val Gln Lys
    130                 135                 140

Leu Val Leu Ile Asp Ser Ala Gly Leu Arg Gly Gly Ser Pro Leu Ser
145                 150                 155                 160

Lys Phe Met Phe Pro Pro Leu Asp Tyr Leu Ala Ala Gln Phe Leu Arg
                165                 170                 175

Ser Pro Lys Val Arg Asp Arg Val Ser Arg Ala Ala Tyr Lys Asn Pro
            180                 185                 190

Asn Leu Ala Thr Val Asp Ala Leu Cys Cys Gly Ala Leu His Leu Glu
        195                 200                 205

Met Pro Ser Trp Pro Glu Ala Leu Ile Ala Phe Thr Lys Ser Gly Gly
    210                 215                 220

Tyr Thr Ala Phe Arg Phe Lys Gln Leu Ala Glu Ile Ile Ser Pro Thr
225                 230                 235                 240

Leu Ile Leu Trp Gly Asp Ala Asp Arg Ile Leu Gly Thr Glu Asp Gly
                245                 250                 255

Lys Arg Phe Lys Arg Ala Ile Pro His Ser Gln Leu Ile Trp Ile Gln
            260                 265                 270

Asp Cys Gly His Ile Pro His Leu Glu Gln Pro Gly Ile Thr Ala Gln
        275                 280                 285

His Ile Leu Ser Phe Cys Ser
    290                 295
```

<210> SEQ ID NO 20
<211> LENGTH: 753
<212> TYPE: PRT
<213> ORGANISM: Escherichia coli

<400> SEQUENCE: 20

```
Met Thr Ile Leu Asn His Thr Leu Gly Phe Pro Arg Val Gly Leu Arg
1               5                   10                  15

Arg Glu Leu Lys Lys Ala Gln Glu Ser Tyr Trp Ala Gly Asn Ser Thr
            20                  25                  30
```

```
Arg Glu Glu Leu Leu Ala Val Gly Arg Glu Leu Arg Ala Arg His Trp
        35                  40                  45

Asp Gln Gln Lys Gln Ala Gly Ile Asp Leu Leu Pro Val Gly Asp Phe
        50                  55                  60

Ala Trp Tyr Asp His Val Leu Thr Thr Ser Leu Leu Gly Asn Val
65              70                  75                  80

Pro Ala Arg His Gln Asn Lys Asp Gly Ser Val Asp Ile Asp Thr Leu
                85                  90                  95

Phe Arg Ile Gly Arg Gly Arg Ala Pro Thr Gly Glu Pro Ala Ala Ala
            100                 105                 110

Ala Glu Met Thr Lys Trp Phe Asn Thr Asn Tyr His Tyr Met Val Pro
            115                 120                 125

Glu Phe Val Lys Gly Gln Gln Phe Lys Leu Thr Trp Thr Gln Leu Leu
            130                 135                 140

Asp Glu Val Asp Glu Ala Leu Ala Leu Gly His Lys Val Lys Pro Val
145                 150                 155                 160

Leu Leu Gly Pro Val Thr Trp Leu Trp Leu Gly Lys Val Lys Gly Glu
                165                 170                 175

Gln Phe Asp Arg Leu Ser Leu Leu Asn Asp Ile Leu Pro Val Tyr Gln
                180                 185                 190

Gln Val Leu Ala Glu Leu Ala Lys Arg Gly Ile Glu Trp Val Gln Ile
        195                 200                 205

Asp Glu Pro Ala Leu Val Leu Glu Leu Pro Gln Ala Trp Leu Asp Ala
        210                 215                 220

Tyr Lys Pro Ala Tyr Asp Ala Leu Gln Gly Gln Val Lys Leu Leu Leu
225                 230                 235                 240

Thr Thr Tyr Phe Glu Gly Val Thr Pro Asn Leu Asp Thr Ile Thr Ala
                245                 250                 255

Leu Pro Val Gln Gly Leu His Val Asp Leu Val His Gly Lys Asp Asp
                260                 265                 270

Val Ala Glu Leu His Lys Arg Leu Pro Ser Asp Trp Leu Leu Ser Ala
        275                 280                 285

Gly Leu Ile Asn Gly Arg Asn Val Trp Arg Ala Asp Leu Thr Glu Lys
        290                 295                 300

Tyr Ala Gln Ile Lys Asp Ile Val Gly Lys Arg Asp Leu Trp Val Ala
305                 310                 315                 320

Ser Ser Cys Ser Leu Leu His Ser Pro Ile Asp Leu Ser Val Glu Thr
                325                 330                 335

Arg Leu Asp Ala Glu Val Lys Ser Trp Phe Ala Phe Ala Leu Gln Lys
            340                 345                 350

Cys His Glu Leu Ala Leu Leu Arg Asp Ala Leu Asn Ser Gly Asp Thr
            355                 360                 365

Ala Ala Leu Ala Glu Trp Ser Ala Pro Ile Gln Ala Arg Arg His Ser
            370                 375                 380

Thr Arg Val His Asn Pro Ala Val Glu Lys Arg Leu Ala Ala Ile Thr
385                 390                 395                 400

Ala Gln Asp Ser Gln Arg Ala Asn Val Tyr Glu Val Arg Ala Glu Ala
                405                 410                 415

Gln Arg Ala Arg Phe Lys Leu Pro Ala Trp Pro Thr Thr Thr Ile Gly
            420                 425                 430

Ser Phe Pro Gln Thr Thr Glu Ile Arg Thr Leu Arg Leu Asp Phe Lys
            435                 440                 445
```

Lys Gly Asn Leu Asp Ala Asn Asn Tyr Arg Thr Gly Ile Ala Glu His
        450                 455                 460

Ile Lys Gln Ala Ile Val Glu Gln Glu Arg Leu Gly Leu Asp Val Leu
465                 470                 475                 480

Val His Gly Glu Ala Glu Arg Asn Asp Met Val Glu Tyr Phe Gly Glu
                485                 490                 495

His Leu Asp Gly Phe Val Phe Thr Gln Asn Gly Trp Val Gln Ser Tyr
            500                 505                 510

Gly Ser Arg Cys Val Lys Pro Pro Val Ile Gly Asp Ile Ser Arg
        515                 520                 525

Pro Ala Pro Ile Thr Val Glu Trp Ala Lys Tyr Ala Gln Ser Leu Thr
530                 535                 540

Asp Lys Pro Val Lys Gly Met Leu Thr Gly Pro Val Thr Ile Leu Cys
545                 550                 555                 560

Trp Ser Phe Pro Arg Glu Asp Val Ser Arg Glu Thr Ile Ala Lys Gln
                565                 570                 575

Ile Ala Leu Ala Leu Arg Asp Glu Val Ala Asp Leu Glu Ala Ala Gly
            580                 585                 590

Ile Gly Ile Ile Gln Ile Asp Glu Pro Ala Leu Arg Glu Gly Leu Pro
        595                 600                 605

Leu Arg Arg Ser Asp Trp Asp Ala Tyr Leu Gln Trp Gly Val Glu Ala
610                 615                 620

Phe Arg Ile Asn Ala Ala Val Ala Lys Asp Asp Thr Gln Ile His Thr
625                 630                 635                 640

His Met Cys Tyr Cys Glu Phe Asn Asp Ile Met Asp Ser Ile Ala Ala
                645                 650                 655

Leu Asp Ala Asp Val Ile Thr Ile Glu Thr Ser Arg Ser Asp Met Glu
            660                 665                 670

Leu Leu Glu Ser Phe Glu Glu Phe Asp Tyr Pro Asn Glu Ile Gly Pro
        675                 680                 685

Gly Val Tyr Asp Ile His Ser Pro Asn Val Pro Ser Val Glu Trp Ile
690                 695                 700

Glu Ala Leu Leu Lys Lys Ala Ala Lys Arg Ile Pro Ala Glu Arg Leu
705                 710                 715                 720

Trp Val Asn Pro Asp Cys Gly Leu Lys Thr Arg Gly Trp Pro Glu Thr
                725                 730                 735

Arg Ala Ala Leu Ala Asn Met Val Gln Ala Ala Gln Asn Leu Arg Arg
            740                 745                 750

Gly

<210> SEQ ID NO 21
<211> LENGTH: 758
<212> TYPE: PRT
<213> ORGANISM: Thermosynechococcus elongatus

<400> SEQUENCE: 21

Met Thr Ile Gln Thr Ala Thr Leu Gly Tyr Pro Arg Ile Gly Lys Asn
1               5                   10                  15

Arg Glu Leu Lys Lys Ala Leu Glu Ala Phe Trp Ser Asn Gln Leu Asp
                20                  25                  30

Ala Glu Ala Leu Leu Lys Thr Ala Gln Asp Ile Glu Leu Gln Asn Trp
            35                  40                  45

Gln Lys Gln Leu Glu Val Gly Ile Asp Arg Ile Gly Ile Gly Asp Leu
        50                  55                  60

-continued

```
Ser Leu Tyr Asp Ser Val Leu Asp Trp Ser Ile Arg Phe Gly Ile Ile
 65                  70                  75                  80

Pro Glu Arg Tyr Arg Ser Phe Thr Gly Leu Glu Gln Tyr Phe Ala Met
                 85                  90                  95

Ala Arg Gly Lys Asp Gly Ile Pro Ala Leu Glu Met Thr Lys Trp Phe
            100                 105                 110

Asp Thr Asn Tyr His Tyr Leu Val Pro Glu Ile Ser Glu Ala Phe Gln
        115                 120                 125

Pro Thr Asp Phe Ser Asp Phe Leu Glu Thr Val Arg Arg Ala Gln Thr
    130                 135                 140

Leu Leu Gly Asp Arg Ala Val Pro Ile Val Leu Gly Pro Leu Thr Leu
145                 150                 155                 160

Leu Arg Leu Ser Arg Leu Glu Thr Asn Leu Glu Gln Ala Val Ser Tyr
                165                 170                 175

Leu Arg Asp Arg Tyr Leu Ile Leu Leu Arg Glu Leu Lys Asn Leu Gly
            180                 185                 190

Val Val Glu Val Gln Ile His Glu Pro Ala Leu Val Leu Glu Glu Ala
        195                 200                 205

Asp Ser Phe Lys Ser Phe Tyr Gln Ser Thr Phe Asp Thr Leu Arg Gln
    210                 215                 220

Ala Asn Leu Pro Leu His Leu Val Thr Tyr Phe Asp Asp Leu Gly Ala
225                 230                 235                 240

Ala Trp Pro Trp Val Met Glu Leu Pro Val Thr Cys Ile Ser Leu Asp
                245                 250                 255

Phe Thr Arg Gly His Asn Leu Ala Leu Leu Lys Glu Tyr Gly Phe Pro
            260                 265                 270

Ala Asp Lys Gln Leu Gly Val Gly Ile Asp Gly Arg Asn Ile Trp
        275                 280                 285

Lys Ile Arg Pro Glu Ser Val Leu Ser Thr Leu Glu Thr Ile Gln Ser
    290                 295                 300

Ile Thr Ala Asn Ile Arg Leu His Pro Ser Ser Leu Gln Phe Val
305                 310                 315                 320

Pro Tyr Asp Ala Lys Arg Glu Val Lys Leu Pro Glu Pro Leu Arg Asp
                325                 330                 335

Val Leu Ser Phe Ala Glu Gln Lys Leu Asp Glu Val Val Leu Leu Ala
            340                 345                 350

Arg Val Leu Asn Ser Asn Asp Gly Thr Asn Arg Glu Ile Leu Met Lys
        355                 360                 365

Asn Pro Glu Leu Thr Ala Ile Gln Ala Gln Trp Lys Ala Phe Glu Gln
    370                 375                 380

Phe Ser Pro Val Asn Pro Thr Val Gln Ala Arg Leu Arg Asn Leu Ser
385                 390                 395                 400

Val Arg Asp Leu Glu Arg Pro Leu Pro Tyr Glu Gln Arg Arg Thr Leu
                405                 410                 415

Gln Pro Thr Leu Pro Pro Leu Pro Thr Thr Ile Gly Ser Phe Pro
            420                 425                 430

Gln Thr Ala Glu Val Arg Gln Leu Arg Val Lys Leu Lys Arg His Glu
        435                 440                 445

Ile Thr Gln Ala Glu Tyr Glu Ala Ala Ile Asp Glu Ile Ala Lys
    450                 455                 460

Cys Val Arg Leu Gln Glu Glu Val Gly Leu Asp Val Leu Val His Gly
465                 470                 475                 480

Glu Phe Glu Arg Ser Asp Met Val Glu Phe Phe Gly Gln Gln Leu Ser
```

```
                    485                 490                 495
Gly Phe Ala Phe Thr Glu His Gly Trp Val Gln Ser Tyr Gly Ser Arg
                500                 505                 510

Cys Val Arg Pro Pro Ile Ile Tyr Gly Asp Ile Ala Arg Pro Gln Pro
            515                 520                 525

Met Thr Val Arg Glu Phe Lys Val Ala Gln Ser Leu Thr Asp Lys Ile
        530                 535                 540

Val Lys Ala Met Leu Thr Gly Pro Val Thr Met Ile Asn Trp Ser Phe
545                 550                 555                 560

Thr Arg Thr Asp Ile Pro Arg Ser Glu Gln Ala Met Gln Ile Ala Leu
                565                 570                 575

Ala Leu Arg Asp Glu Val Ala Asp Leu Glu Ala Gly Ala Lys Met
                580                 585                 590

Ile Gln Ile Asp Glu Pro Ala Leu Arg Glu Gly Leu Pro Leu Lys Ala
            595                 600                 605

Glu Arg Trp Asn Glu Tyr Leu Ser Trp Ala Val Asp Ala Phe Arg Leu
        610                 615                 620

Ala Ala Gly Val Ala Lys Pro Glu Thr Gln Ile His Thr His Met Cys
625                 630                 635                 640

Tyr Ser Glu Phe Gly Asp Ile Ile Glu His Ile Glu Arg Leu Asp Ala
                645                 650                 655

Asp Val Leu Ser Ile Glu Asn Ser Arg Ser Asn Asn Glu Thr Leu Phe
                660                 665                 670

Gln Ile Thr Asp Ala Gly Tyr Arg His Gln Val Gly Val Gly Val Tyr
            675                 680                 685

Asp Val His Ser Pro Ala Val Pro Ser Val Glu Gln Leu Val Gln Gln
        690                 695                 700

Leu Arg Thr Ser Val Ala Asn Leu Ala Pro Glu Gln Ile Trp Val Asn
705                 710                 715                 720

Pro Asp Cys Gly Leu Lys Thr Arg His Trp Glu Val Ile Pro Ser
                725                 730                 735

Leu Lys Asn Met Val Glu Ala Thr Lys Thr Ile Arg Gln Glu Val Met
                740                 745                 750

Gln Ser Lys Asn Asn Ala
        755

<210> SEQ ID NO 22
<211> LENGTH: 734
<212> TYPE: PRT
<213> ORGANISM: Thermotoga maritima

<400> SEQUENCE: 22

Met Lys Ala Tyr Ala Phe Gly Phe Pro Lys Ile Gly Glu Lys Arg Glu
1               5                   10                  15

Phe Lys Lys Ala Leu Glu Asp Phe Trp Lys Gly Lys Ile Thr Glu Glu
                20                  25                  30

Gln Phe Glu Glu Glu Met Asn Lys Leu Arg Met Tyr Met Val Glu Asn
            35                  40                  45

Tyr Arg Lys Asn Val Asp Val Ile Pro Ser Asn Glu Leu Ser Tyr Tyr
        50                  55                  60

Asp Phe Val Leu Asp Thr Ala Val Met Val Gly Ala Val Pro Glu Arg
65                  70                  75                  80

Phe Gly Glu Tyr Arg Gly Leu Ser Thr Tyr Phe Asp Met Ala Arg Gly
                85                  90                  95
```

```
Gly Lys Ala Leu Glu Met Thr Lys Phe Phe Asn Thr Asn Tyr His Tyr
            100                 105                 110
Leu Val Pro Glu Ile Glu Thr Glu Glu Phe Tyr Leu Leu Glu Asn Lys
        115                 120                 125
Pro Leu Glu Asp Tyr Leu Phe Phe Lys Ser Lys Gly Ile Glu Thr Ala
        130                 135                 140
Pro Trp Val Ile Gly Pro Phe Thr Phe Leu Tyr Leu Ser Lys Arg Asn
145                 150                 155                 160
Gly Glu Trp Ile Arg Arg Pro Asn Gln Met Glu Lys Leu Leu Glu Ser
                165                 170                 175
Leu Val Ser Val Tyr Lys Glu Val Phe Glu Lys Leu Val Glu Asn Gly
                180                 185                 190
Cys Lys Glu Ile Leu Val Asn Glu Pro Ala Phe Val Cys Asp Leu Glu
        195                 200                 205
Lys Ala His Trp Asp Leu Ile Leu Asn Val Tyr Arg Glu Leu Ser Glu
        210                 215                 220
Phe Pro Leu Thr Val Phe Thr Tyr Tyr Asp Ser Val Ser Asp Tyr Glu
225                 230                 235                 240
Ala Cys Val Ser Leu Pro Val Lys Arg Leu His Phe Asp Phe Val Ser
                245                 250                 255
Asn Glu Glu Asn Leu Lys Asn Leu Glu Lys His Gly Phe Pro Glu Asp
                260                 265                 270
Lys Lys Leu Val Ala Gly Val Ile Asn Gly Arg Gln Pro Trp Lys Val
        275                 280                 285
Asp Leu Arg Lys Val Ala Ser Leu Val Glu Lys Leu Gly Ala Ser Ala
        290                 295                 300
Ile Ser Asn Ser Cys Pro Leu Phe His Leu Pro Val Thr Leu Glu Leu
305                 310                 315                 320
Glu Asn Asn Leu Pro Gly Gly Leu Lys Glu Lys Leu Ala Phe Ala Lys
                325                 330                 335
Glu Lys Leu Glu Glu Leu Lys Met Leu Lys Asp Phe Leu Glu Gly Lys
                340                 345                 350
Thr Phe Asp Leu Pro Asn Val Ser Phe Glu Asp Phe Ala Val Asp Leu
        355                 360                 365
Gln Ala Val Glu Arg Val Arg Asn Leu Pro Glu Asp Ser Phe Arg Arg
        370                 375                 380
Glu Lys Glu Tyr Thr Glu Arg Asp Arg Ile Gln Arg Glu Arg Leu Asn
385                 390                 395                 400
Leu Pro Leu Phe Pro Thr Thr Ile Gly Ser Phe Pro Gln Thr Pro
                405                 410                 415
Glu Val Arg Lys Met Arg Ser Lys Tyr Arg Lys Gly Glu Ile Ser Lys
                420                 425                 430
Glu Glu Tyr Glu Ala Phe Ile Lys Glu Gln Ile Lys Lys Ala Ile Glu
        435                 440                 445
Leu Gln Glu Glu Ile Gly Leu Asp Val Leu His Gly Glu Phe Glu
        450                 455                 460
Arg Thr Asp Met Val Glu Phe Phe Ala Glu Lys Leu Asn Gly Ile Ala
465                 470                 475                 480
Thr Thr Gln Asn Gly Trp Val Leu Ser Tyr Gly Ser Arg Cys Tyr Arg
                485                 490                 495
Pro Pro Ile Ile Tyr Gly Thr Val Thr Arg Pro Glu Pro Met Thr Leu
                500                 505                 510
Lys Glu Ile Thr Tyr Ala Gln Ser Leu Thr Glu Lys Pro Val Lys Gly
```

-continued

```
            515                 520                 525
Met Leu Thr Gly Pro Val Thr Ile Met Ser Trp Ser Tyr Tyr Arg Glu
    530                 535                 540

Asp Ile Pro Glu Arg Glu Ile Ala Tyr Gln Ile Ala Leu Ala Ile Asn
545                 550                 555                 560

Glu Glu Val Lys Asp Leu Glu Glu Ala Gly Ile Lys Ile Val Gln Ile
                565                 570                 575

Asp Glu Pro Ala Phe Arg Glu Lys Ala Pro Ile Lys Lys Ser Lys Trp
                580                 585                 590

Pro Glu Tyr Phe Glu Trp Ala Ile Asn Ala Phe Asn Leu Ala Ala Asn
    595                 600                 605

Ala Arg Pro Glu Thr Gln Ile His Ala His Met Cys Tyr Ser Asp Phe
    610                 615                 620

Asn Glu Ile Ile Glu Tyr Ile His Gln Leu Glu Phe Asp Val Ile Ser
625                 630                 635                 640

Ile Glu Ala Ser Arg Ser Lys Gly Glu Ile Ile Ser Ala Phe Glu Asn
                645                 650                 655

Phe Lys Gly Trp Ile Lys Gln Ile Gly Val Gly Val Trp Asp Ile His
                660                 665                 670

Ser Pro Ala Val Pro Ser Ile Asn Glu Met Arg Glu Ile Val Glu Arg
    675                 680                 685

Val Leu Arg Val Leu Pro Lys Glu Leu Ile Trp Ile Asn Pro Asp Cys
    690                 695                 700

Gly Leu Lys Thr Arg Asn Trp Asp Glu Val Ile Pro Ser Leu Arg Asn
705                 710                 715                 720

Met Val Ala Leu Ala Lys Glu Met Arg Glu Lys Phe Glu Ser
                725                 730
```